(12) United States Patent
Davis et al.

(10) Patent No.: US 6,174,676 B1
(45) Date of Patent: Jan. 16, 2001

(54) CYTOKINE-STRESS- AND ONCOPROTEIN-ACTIVATED HUMAN PROTEIN KINASE KINASES

(75) Inventors: Roger J. Davis, Princeton, MA (US); Joel Raingeaud, Palaiseau; Benoit Derijard, Nice, both of (FR)

(73) Assignee: University of Massachusetts, Worcester, MA (US)

( * ) Notice: Under 35 U.S.C. 154(b), the term of this patent shall be extended for 0 days.

(21) Appl. No.: 09/149,879

(22) Filed: Sep. 8, 1998

Related U.S. Application Data

(63) Continuation of application No. 09/057,009, filed on Apr. 7, 1998, which is a continuation-in-part of application No. 08/539,950, filed on Sep. 19, 1995, now Pat. No. 5,736,381, which is a continuation-in-part of application No. 08/446,083, filed on May 19, 1995, now Pat. No. 5,804,427.

(51) Int. Cl.[7] .............................. C12Q 1/68; C12N 9/12; G01N 33/566; C07K 16/00; C07H 21/04

(52) U.S. Cl. ............................. 435/6; 436/501; 436/94; 435/810; 435/194; 435/975; 530/387.1; 536/23.1; 536/24.3; 536/24.33; 536/25.3

(58) Field of Search ....................... 514/2, 44; 435/254.1, 435/194, 6, 7.1, 91.1, 810, 975, 183; 436/501, 94; 530/387.1; 536/23.1, 24.3, 24.33, 25.3; 204/456

(56) References Cited

U.S. PATENT DOCUMENTS 5,981,265 * 11/1999 Johnson ............................ 435/254.1

FOREIGN PATENT DOCUMENTS

WO 94/24159  10/1994  (WO).
WO 95/28421  10/1995  (WO).

OTHER PUBLICATIONS

L'Allemain, Gilles "Decphering the MAP Kinase Pathway" Progress in Growth Factor Research, vol. 5, pp. 291–334 1994.*

Dérijard et al., *Science*, 267:682–685, (1995).
Freshney et al., *Cell*, 78:1039–1049, (1994).
Galcheva–Gargova et al., *Science*, 265:806–808, (1994).
Gupta et al., *Science*, 267:389–393, (1995).
Han et al., *J. Biol. Chem.*, 271:2886–2891, (1996).
Hillier et al., EMBL Database entry HS78336; Accession No. T66783; Apr. 8, 1995; The WashU–Merck EST Project, XP002058577 (abstract).
Lin et al., *Science*, 268:286–290, (1995).
Minden et al., *Science*, 266:1719–1723, (1994).
Raingeaud et al., *The Journal of Biological Chemistry*, 270:7420–7426, (1995).
Rouse et al., *Cell*, 78:1027–1037, (1994).
Sanchez et al., *Nature*, 372:794–798, (1994).
Seger et al., *J. Biological Chemistry*, 267:25628–25631 (1992).
Whitmarsh et al., Science, 269:403–407, (1995).
Wu et al., *Molecular and Cellular Biology*, 13:4539–4548, (1993).
Xia et al., *Science*, 270:1326–1331, (1995).
Yan et al., *Nature*, 372:798–800, (1994).
Yashar et al., *Molecular and Cellular Biology*, 13:5738–5748, (1993).

* cited by examiner

*Primary Examiner*—Bradley L. Sisson
(74) *Attorney, Agent, or Firm*—Fish & Richardson, P.C.

(57) ABSTRACT

Disclosed are human mitogen-activated (MAP) kinase kinase isoforms (MKKs). MKKs mediate unique signal transduction pathways that activate human-MAP kinases p38 and JNK, which result in activation of other factors, including activating transcription factor-2 (ATF2) and c-Jun. The pathways are activated by a number of factors, including cytokines and environmental stress. Methods are provided for identifying reagents that modulate MKK function or activity and for the use of such reagents in the treatment of MKK-mediated disorders.

29 Claims, 28 Drawing Sheets

```
                                                                                        71
          MSKPP----------APNPTPPRN-----------LDSRTFITIG------DRNFEVEADD
MKK3  MQGKRRALKLNFAN..FKSTARFTLN...GVQ.PHIERLRTHSIE.SGKLK.SP----EQHWDFT.E.
MKK4  MPKKKP--TPIQLN.A-PDGSAVNGTSSAETNLEALQKKLEELE..EQQRKRLEAFLTQKQKVG.LKD..
MEK1  MLARRKPVLPALTIN.TIAEGPSPTSEGASEANLVDLQKKLEELE..EQQKKRLEAFLTQKAKVG.LKD..
MEK2  <GTTPRTGNSNNS-NSGSSGGGLFANFSKYVDIKSGSLNFAGKLSL.SKG.DFSN------GSSSRITL.E
PBS2
Consensus I                        II                    III              IV  142
MKK3  LVTISELGRGAYGVVEKVRHAQSGTIMAVKRIRATVNSQEQKRLLMDLDINMRTVDCFYTVTFYGALFREG
MKK4  .KDLG.I......S.N.MV.KP..Q........S..DEK..Q......VV..SS..P.I.Q.........
MEK1  FEK.....A.NG...F.VS.KP..LV..R.L.HLEIKPAIRNQIIRE.QV-LHECNSP.I.G.....FYSD.
MEK2  FER.....A.NG...T.VQ.RP..L....R.L.HLEIKPAIRNQIIRE.QV-LHECNSP.I.G.....FYSD.
PBS2  .EFLD..H.N..N.S.VL.KPTNV...T.EV.LELDEAKFRQI..E.EV-LHKCNSP.I.D....F.I..
Consensus        E G G  G V K H      MA K                         Y V FYGA    G 143          V                   VI                                            213
MKK3  DVWICMELMD-TSLDKFYR---KVLDKNMTIPEDILGEIAVSIVRALEHLHSKLSVIHRDVKPSNVL-INK
MKK4  .C......S--.F...Q-----.KYVYS...D--V...E...K.TLAT.K..N..KEN.KI.....I....I.-LDR
MEK1  EIS....H..GG...Q--------.K.AGR....Q...KVSIAVIKG.TY.RE.HKIM..........I.-V.S
MEK2  EIS....H..GG...Q-----..KEAKR....E...KVSIAVL.G.AY.RE.HQIM..........I.-V.S
PBS2  A.YM..Y..GG....IYDESSEIG-----.D.PQ.AF..NAVIHG.KE.KEQHNI.......T.I.CSAN
Consensus        CME M   S D         I E  L              L L    L     HRD KP N  L 214                VII       *   *       VIII                    IX                         284
MKK3  EGHVKMCDFGISGYLVDSVAKTMDAGCKPYMAPERINP-ELNQKGYNVKSDVWSLGITMIEMAILRFPY---
MKK4  S.NI.L......Q......I...R....R......D.-SASRQ..D.R.........LY.L.TG...---
MEK1  R.EI.L.....V..Q.I..M.NSF-V.TRS..S...LQGTH------.S.Q...I..M.LSLV...VG.Y.IPP
MEK2  R.EI.L.....V..Q.I..M.NSF-V.TRS......LQGTH------.S.Q...I..M.LSLV.L.VG.Y.IPP
PBS2  Q.T..L...V..N..A.L....NI..QS......KSLNPDRAT.T.Q.I.....LSIL....LG.Y..PP
Consensus  G  K CDFG SG L  S A         G   YM PER           Y V SD WS G    E A R P X                                             355
MKK3  -------------------------------TPFQQLKQVVEEPSPQLPAD---R
MKK4  ESWG-----------------------------SV.D..T...KGDP...SNSEERE
MEK1  PDAKELELMFGCQV-----EGDAAETPPRPRTPGRPLSSYGMDSRPPMAI.EL.DYI.N..P.K..SGV---
MEK2  PDAKELEAIFGRPVVDGEEGEPHSISPRPRPGRPVSGHGMDSRPAMAI.EL.DYI.N..P.K..NGV---
PBS2  .TYD------------------------------NI.S..SAI.DG.P.R..S.---K
Consensus                                                        F  L V   P L 356                                                                               426
MKK3  FSPEFVDFTAQCLRKNPAERMSYLELMEHPFFTLHKTKKTDIAAFVK-------KILGEDS
MKK4  ..S.IN.VNL..T.DESK.PK.K..LK...ILMYEERAVEV.CY.C------..DQMPATPSSPMYVD
MEK1  ..L..Q..VNK..I......ADLKQ..V.A.IKRSDAEEV.F.GWLCSTIGLNQPSTPTHAAGV
MEK2  .T.D.QE.VNK..I......ADLKM.TN.T.IKRSEVEEV.F.GWLCKTLRLNQPGTPTRTA
PBS2  ..SDAQD.VSL..Q.I.ER.PT.AA.T..PWLVKYRNQDVHMSEYITERLERRN...R.RGENGLSKNVP>
Consensus  F      F   CL K    R        L  H
```

FIG. 1

```
  5         10         15         20         25         30         35         40         45         50         55         60
  *                    *                     *                     *                     *                     *
TGGCTGGCAA TGGCCTTGCT GACCTCGAGC CGGGCCCACG TGGGGACCTT TGGAGCACAG
ACCGACCGTT ACCGGAACGA CTGGAGCTCG GCCCGGGTGC ACCCCTGGAA ACCTCGTGTC 65         70         75         80         85         90         95        100        105        110        115        120
  *                    *                     *                     *                     *                     *
CCTACGATCC TGGTGCAAGG CCGGTGGATG CAGAGGCCAG TCCATATACC ACCCAGGCCT
GGATGCTAGG ACCACGTTCC GGCCACCTAC GTCTCCGGTC AGGTATATGG TGGGTCCGGA 125        130        135        140        145        150        155        160        165        170        175        180
  *                    *                     *                     *                     *                     *
GCGAGGAGCG TGGTCCCCAC CCATCCAGCC CATATGTGCA AGTGCCCTTG ACAGAGAGGC
CGCTCCTCGC ACCAGGGGTG GGTAGGTCGG GTATACACGT TCACGGGAAC TGTCTCTCCG 185        190        195        200        205        210        215        220        225        230        235        240
  *                    *                     *                     *                     *                     *
TGGTCATATC CATGGTGACC ATTTATGGGC CACAACAGGT CCCCATCTGC GCAGTGAACC
ACCAGTATAG GTACCACTGG TAAATACCCG GTGTTGTCCA GGGGTAGACG CGTCACTTGG 245        250        255        260        265        270        275        280        285        290        295        300
  *                    *                     *                     *                     *                     *
CTGTGCTGAG CACCTTGCAG ACGTGATCTT GCTTCGTCCT GCAGCACTGT GCGGGGCAGG
GACACGACTC GTGGAACGTC TGCACTAGAA CGAAGCAGGA CGTCGTGACA CGCCCCGTCC 305        310        315        320        325        330        335        340        345        350        355
  *                    *                     *                     *                     *
AAAATCCAAG AGGAAGAAGG ATCTACGGAT ATCCTGC ATG TCC AAG CCA CCC GCA
TTTTAGGTTC TCCTTCTTCC TAGATGCCTA TAGGACG TAC AGG TTC GGT GGG CGT
                                          Met Ser Lys Pro Pro Ala>

360        365        370        375        380        385        390        395        400
      *                    *                     *                     *                     *
CCC AAC CCC ACA CCC CCC CGG AAC CTG GAC TCC CGG ACC TTC ATC ACC
GGG TTG GGG TGT GGG GGG GCC TTG GAC CTG AGG GCC TGG AAG TAG TGG
Pro Asn Pro Thr Pro Pro Arg Asn Leu Asp Ser Arg Thr Phe Ile Thr>

405        410        415        420        425        430        435        440        445        450
  *                    *                     *                     *                     *
ATT GGA GAC AGA AAC TTT GAG GTG GAG GCT GAT GAC TTG GTG ACC ATC
TAA CCT CTG TCT TTG AAA CTC CAC CTC CGA CTA CTG AAC CAC TGG TAG
Ile Gly Asp Arg Asn Phe Glu Val Glu Ala Asp Asp Leu Val Thr Ile>

455        460        465        470        475        480        485        490        495
      *                    *                     *                     *
TCA GAA CTG GGC CGT GGA GCC TAT GGG GTG GTA GAG AAG GTG CGG CAC
AGT CTT GAC CCG GCA CCT CGG ATA CCC CAC CAT CTC TTC CAC GCC GTG
Ser Glu Leu Gly Arg Gly Ala Tyr Gly Val Val Glu Lys Val Arg His>

500        505        510        515        520        525        530        535        540        545
  *                    *                     *                     *                     *
GCC CAG AGC GGC ACC ATC ATG GCC GTG AAG CGG ATC CGG GCC ACC GTG
CGG GTC TCG CCG TGG TAG TAC CGG CAC TTC GCC TAG GCC CGG TGG CAC
Ala Gln Ser Gly Thr Ile Met Ala Val Lys Arg Ile Arg Ala Thr Val>

550        555        560        565        570        575        580        585        590        595
  *                    *                     *                     *                     *
AAC TCA CAG GAG CAG AAG CGG CTG CTC ATG GAC CTG GAC ATC AAC ATG
TTG AGT GTC CTC GTC TTC GCC GAC GAG TAC CTG GAC CTG TAG TTG TAC
Asn Ser Gln Glu Gln Lys Arg Leu Leu Met Asp Leu Asp Ile Asn Met>
```

FIG. 4A

```
      600       605       610       615       620       625       630       635       640
       *                   *                   *                   *                   *
      CGC ACG GTC GAC TGT TTC TAC ACT GTC ACC TTC TAC GGG GCA CTA TTC
      GCG TGC CAG CTG ACA AAG ATG TGA CAG TGG AAG ATG CCC CGT GAT AAG
      Arg Thr Val Asp Cys Phe Tyr Thr Val Thr Phe Tyr Gly Ala Leu Phe>

645       650       655       660       665       670       675       680       685       690
       *                   *                   *                   *                   *
      AGA GAG GGA GAC GTG TGG ATC TGC ATG GAG CTC ATG GAC ACA TCC TTG
      TCT CTC CCT CTG CAC ACC TAG ACG TAC CTC GAG TAC CTG TGT AGG AAC
      Arg Glu Gly Asp Val Trp Ile Cys Met Glu Leu Met Asp Thr Ser Leu>

695       700       705       710       715       720       725       730       735
       *                   *                   *                   *                   *
      GAC AAG TTC TAC CGG AAG GTG CTG GAT AAA AAC ATG ACA ATT CCA GAG
      CTG TTC AAG ATG GCC TTC CAC GAC CTA TTT TTG TAC TGT TAA GGT CTC
      Asp Lys Phe Tyr Arg Lys Val Leu Asp Lys Asn Met Thr Ile Pro Glu>

740       745       750       755       760       765       770       775       780       785
       *                   *                   *                   *                   *
      GAC ATC CTT GGG GAG ATT GCT GTG TCT ATC GTG CGG GCC CTG GAG CAT
      CTG TAG GAA CCC CTC TAA CGA CAC AGA TAG CAC GCC CGG GAC CTC GTA
      Asp Ile Leu Gly Glu Ile Ala Val Ser Ile Val Arg Ala Leu Glu His>

790       795       800       805       810       815       820       825       830       835
       *                   *                   *                   *                   *
      CTG CAC AGC AAG CTG TCG GTG ATC CAC AGA GAT GTG AAG CCC TCC AAT
      GAC GTG TCG TTC GAC AGC CAC TAG GTG TCT CTA CAC TTC GGG AGG TTA
      Leu His Ser Lys Leu Ser Val Ile His Arg Asp Val Lys Pro Ser Asn>

840       845       850       855       860       865       870       875       880
       *                   *                   *                   *                   *
      GTC CTT ATC AAC AAG GAG GGC CAT GTG AAG ATG TGT GAC TTT GGC ATC
      CAG GAA TAG TTG TTC CTC CCG GTA CAC TTC TAC ACA CTG AAA CCG TAG
      Val Leu Ile Asn Lys Glu Gly His Val Lys Met Cys Asp Phe Gly Ile>

885       890       895       900       905       910       915       920       925       930
       *                   *                   *                   *                   *
      AGT GGC TAC TTG GTG GAC TCT GTG GCC AAG ACG ATG GAT GCC GGC TGC
      TCA CCG ATG AAC CAC CTG AGA CAC CGG TTC TGC TAC CTA CGG CCG ACG
      Ser Gly Tyr Leu Val Asp Ser Val Ala Lys Thr Met Asp Ala Gly Cys>

935       940       945       950       955       960       965       970       975
       *                   *                   *                   *                   *
      AAG CCC TAC ATG GCC CCT GAG AGG ATC AAC CCA GAG CTG AAC CAG AAG
      TTC GGG ATG TAC CGG GGA CTC TCC TAG TTG GGT CTC GAC TTG GTC TTC
      Lys Pro Tyr Met Ala Pro Glu Arg Ile Asn Pro Glu Leu Asn Gln Lys>

980       985       990       995      1000      1005      1010      1015      1020      1025
       *                   *                   *                   *                   *
      GGC TAC AAT GTC AAG TCC GAC GTC TGG AGC CTG GGC ATC ACC ATG ATT
      CCG ATG TTA CAG TTC AGG CTG CAG ACC TCG GAC CCG TAG TGG TAC TAA
      Gly Tyr Asn Val Lys Ser Asp Val Trp Ser Leu Gly Ile Thr Met Ile>

1030      1035      1040      1045      1050      1055      1060      1065      1070      1075
       *                   *                   *                   *                   *
      GAG ATG GCC ATC CTG CGG TTC CCT TAC GAG TCC TGG GGG ACC CCG TTC
      CTC TAC CGG TAG GAC GCC AAG GGA ATG CTC AGG ACC CCC TGG GGC AAG
      Glu Met Ala Ile Leu Arg Phe Pro Tyr Glu Ser Trp Gly Thr Pro Phe>

```
      *              *              *              *              *
   CAG CAG CTG AAG CAG GTG GTG GAG GAG CCG TCC CCC CAG CTC CCA GCC
   GTC GTC GAC TTC GTC CAC CAC CTC CTC GGC AGG GGG GTC GAG GGT CGG
   Gln Gln Leu Lys Gln Val Val Glu Glu Pro Ser Pro Gln Leu Pro Ala>

1125      1130      1135      1140      1145      1150      1155      1160      1165      1170
    *                   *                             *                                      *
   GAC CGT TTC TCC CCC GAG TTT GTG GAC TTC ACT GCT CAG TGC CTG AGG
   CTG GCA AAG AGG GGG CTC AAA CAC CTG AAG TGA CGA GTC ACG GAC TCC
   Asp Arg Phe Ser Pro Glu Phe Val Asp Phe Thr Ala Gln Cys Leu Arg>

1175      1180      1185      1190      1195      1200      1205      1210      1215
       *              *              *              *              *
   AAG AAC CCC GCA GAG CGT ATG AGC TAC CTG GAG CTG ATG GAG CAC CCC
   TTC TTG GGG CGT CTC GCA TAC TCG ATG GAC CTC GAC TAC CTC GTG GGG
   Lys Asn Pro Ala Glu Arg Met Ser Tyr Leu Glu Leu Met Glu His Pro>

1220 1225      1230      1235      1240      1245      1250      1255      1260      1265
           *              *              *              *              *
   TTC TTC ACC TTG CAC AAA ACC AAG AAG ACG GAC ATT GCT GCC TTC GTG
   AAG AAG TGG AAC GTG TTT TGG TTC TTC TGC CTG TAA CGA CGG AAG CAC
   Phe Phe Thr Leu His Lys Thr Lys Lys Thr Asp Ile Ala Ala Phe Val>

1270      1275      1280 1285      1290      1295 1300      1305 1310      1315 1320
    *                   *                   *                   *                   *
   AAG AAG ATC CTG GGA GAA GAC TCA TAGGGGCTG GGCCTCGGAC CCCACTCCGG
   TTC TTC TAG GAC CCT CTT CTG AGT ATCCCCGAC CCGGAGCCTG GGGTGAGGCC
   Lys Lys Ile Leu Gly Glu Asp Ser>  (SEQ ID NO:2)

1325 1330      1335 1340      1345 1350      1355 1360      1365 1370      1375 1380
              *                   *                   *                   *                   *
   CCCTCCAGAG  CCCCACAGCC  CCATCTGCGG  GGGCAGTGCT  CACCCACACC  ATAAGCTACT
   GGGAGGTCTC  GGGGTGTCGG  GGTAGACGCC  CCCGTCACGA  GTGGGTGTGG  TATTCGATGA 1385 1390      1395 1400      1405 1410      1415 1420      1425 1430      1435 1440
              *                   *                   *                   *                   *
   GCCATCCTGG  CCCAGGGCAT  CTGGGAGGAA  CCGAGGGGGC  TGCTCCCACC  TGGCTCTGTG
   CGGTAGGACC  GGGTCCCGTA  GACCCTCCTT  GGCTCCCCCG  ACGAGGGTGG  ACCGAGACAC 1445 1450      1455 1460      1465 1470      1475 1480      1485 1490      1495 1500
              *                   *                   *                   *                   *
   GCGAGCCATT  TGTCCCAAGT  GCCAAAGAAG  CAGACCATTG  GGGCTCCCAG  CCAGGCCCTT
   CGCTCGGTAA  ACAGGGTTCA  CGGTTTCTTC  GTCTGGTAAC  CCCGAGGGTC  GGTCCGGGAA 1505 1510      1515 1520      1525 1530      1535 1540      1545 1550      1555 1560
              *                   *                   *                   *                   *
   GTCGGCCCCA  CCAGTGCCTC  TCCCTGCTGC  TCCTAGGACC  CGTCTCCAGC  TGCTGAGATC
   CAGCCGGGGT  GGTCACGGAG  AGGGACGACG  AGGATCCTGG  GCAGAGGTCG  ACGACTCTAG 1565 1570      1575 1580      1585 1590      1595 1600      1605 1610      1615 1620
              *                   *                   *                   *                   *
   CTGGACTGAG  GGGGCCTGGA  TGCCCCCTGT  GGATGCTGCT  GCCCCTGCAC  AGCAGGCTGC
   GACCTGACTC  CCCCGGACCT  ACGGGGGACA  CCTACGACGA  CGGGGACGTG  TCGTCCGACG 1625 1630      1635 1640      1645 1650      1655 1660      1665 1670      1675 1680
              *                   *                   *                   *                   *
   CAGTGCCTGG  GTGGATGGGC  CACCGCCTTG  CCCAGCCTGG  ATGCCATCCA  AGTTGTATAT
   GTCACGGACC  CACCTACCCG  GTGGCGGAAC  GGGTCGGACC  TACGGTAGGT  TCAACATATA 1685 1690      1695 1700      1705 1710      1715 1720      1725 1730      1735 1740
              *                   *                   *                   *                   *
   TTTTTTAATC  TCTCGACTGA  ATGGACTTTG  CACACTTTGG  CCCAGGGTGG  CCACACCTCT
```

FIG. 4C

```
AAAAAATTAG AGAGCTGACT TACCTGAAAC GTGTGAAACC GGGTCCCACC GGTGTGGAGA 1745 1750  1755 1760  1765 1770  1775 1780  1785 1790  1795 1800
     *          *          *          *          *          *
ATCCCGGCTT TGGTGCGGGG TACACAAGAG GGGATGAGTT GTGTGAATAC CCCAAGACTC
TAGGGCCGAA ACCACGCCCC ATGTGTTCTC CCCTACTCAA CACACTTATG GGGTTCTGAG 1805 1810  1815 1820  1825 1830  1835 1840  1845 1850  1855 1860
     *          *          *          *          *          *
CCATGAGGGA GATGCCATGA GCCGCCCAAG GCCTTCCCCT GGCACTGGCA AACAGGGCCT
GGTACTCCCT CTACGGTACT CGGCGGGTTC CGGAAGGGGA CCGTGACCGT TTGTCCCGGA 1865 1870  1875 1880  1885 1890  1895 1900  1905 1910  1915 1920
     *          *          *          *          *          *
CTGCGGAGCA CACTGGCTCA CCCAGTCCTG CCCGCCACCG TTATCGGTGT CATTCACCTT
GACGCCTCGT GTGACCGAGT GGGTCAGGAC GGGCGGTGGC AATAGCCACA GTAAGTGGAA 1925 1930  1935 1940  1945 1950  1955 1960  1965 1970  1975 1980
     *          *          *          *          *          *
TCGTGTTTTT TTTAATTTAT CCTCTGTTGA TTTTTTCTTT TGCTTTATGG GTTTGGCTTG
AGCACAAAAA AAATTAAATA GGAGACAACT AAAAAAGAAA ACGAAATACC CAAACCGAAC 1985 1990  1995 2000  2005 2010  2015 2020  2025 2030
     *          *          *          *          *
TTTTTCTTGC ATGGTTTGGA GCTGATCGCT TCTCCCCCAC CCCCTAGGGG    (SEQ ID NO: 1)
AAAAAGAACG TACCAAACCT CGACTAGCGA AGAGGGGGTG GGGGATCCCC
```

FIG. 4D

```
        5         10        15        20        25        30        35        40        45        50        55        60
        *                   *                   *                   *                   *                   *
TAGCTGCAGC ACAGCCTTCC CTAACGTTGC AACTGGGGGA AAAATCACTT TCCAGTCTGT
ATCGACGTCG TGTCGGAAGG GATTGCAACG TTGACCCCCT TTTTAGTGAA AGGTCAGACA 65        70        75        80        85        90        95       100       105       110       115       120
        *                   *                   *                   *                   *                   *
TTTGCAAGGT GTGCATTTCC ATCTTGATTC CCTGAAAGTC CATCTGCTGC ATCGGTCAAG
AAACGTTCCA CACGTAAAGG TAGAACTAAG GGACTTTCAG GTAGACGACG TAGCCAGTTC 125       130       135       140       145       150       155       160       165       170       175       180
        *                   *                   *                   *                   *                   *
AGAAACTCCA CTTGCATGAA GATTGCACGC CTGCAGCTTG CATCTTTGTT GCAAAACTAG
TCTTTGAGGT GAACGTACTT CTAACGTGCG GACGTCGAAC GTAGAAACAA CGTTTTGATC 185       190       195       200       205       210       215       220       225       230       235       240
        *                   *                   *                   *                   *                   *
CTACAGAAGA GAAGCAAGGC AAAGTCTTTT GTGCTCCCCT CCCCCATCAA AGGAAAGGGG
GATGTCTTCT CTTCGTTCCG TTTCAGAAAA CACGAGGGGA GGGGGTAGTT TCCTTTCCCC 245         250         255         260         265         270         275         280         285
                    *                       *                       *                       *
AAA ATG TCT CAG TCG AAA GGC AAG AAG CGA AAC CCT GGC CTT AAA ATT
TTT TAC AGA GTC AGC TTT CCG TTC TTC GCT TTG GGA CCG GAA TTT TAA
    Met Ser Gln Ser Lys Gly Lys Lys Arg Asn Pro Gly Leu Lys Ile>

290         295         300         305         310         315         320         325         330         335
             *                       *                       *                       *                       *
CCA AAA GAA GCA TTT GAA CAA CCT CAG ACC AGT TCC ACA CCA CCT AGA
GGT TTT CTT CGT AAA CTT GTT GGA GTC TGG TCA AGG TGT GGT GGA TCT
Pro Lys Glu Ala Phe Glu Gln Pro Gln Thr Ser Ser Thr Pro Pro Arg>

340         345         350         355         360         365         370         375         380
             *                       *                       *                       *
GAT TTA GAC TCC AAG GCT TGC ATT TCT ATT GGA AAT CAG AAC TTT GAG
CTA AAT CTG AGG TTC CGA ACG TAA AGA TAA CCT TTA GTC TTG AAA CTC
Asp Leu Asp Ser Lys Ala Cys Ile Ser Ile Gly Asn Gln Asn Phe Glu>

385         390         395         400         405         410         415         420         425         430
             *                       *                       *                       *                       *
GTG AAG GCA GAT GAC CTG GAG CCT ATA ATG GAA CTG GGA CGA GGT GCG
CAC TTC CGT CTA CTG GAC CTC GGA TAT TAC CTT GAC CCT GCT CCA CGC
Val Lys Ala Asp Asp Leu Glu Pro Ile Met Glu Leu Gly Arg Gly Ala>

435         440         445         450         455         460         465         470         475         480
                   *                       *                       *                       *                       *
TAC GGG GTG GTG GAG AAG ATG CGG CAC GTG CCC AGC GGG CAG ATC ATG
ATG CCC CAC CAC CTC TTC TAC GCC GTG CAC GGG TCG CCC GTC TAG TAC
Tyr Gly Val Val Glu Lys Met Arg His Val Pro Ser Gly Gln Ile Met>

485         490         495         500         505         510         515         520         525
                   *                       *                       *                       *
GCA GTG AAG CGG ATC CGA GCC ACA GTA AAT AGC CAG GAA CAG AAA CGG
CGT CAC TTC GCC TAG GCT CGG TGT CAT TTA TCG GTC CTT GTC TTT GCC
Ala Val Lys Arg Ile Arg Ala Thr Val Asn Ser Gln Glu Gln Lys Arg>

530         535         540         545         550         555         560         565         570         575
                   *                       *                       *                       *                       *
CTA CTG ATG GAT TTG GAT ATT TCC ATG AGG ACG GTG GAC TGT CCA TTC
GAT GAC TAC CTA AAC CTA TAA AGG TAC TCC TGC CAC CTG ACA GGT AAG
```

FIG. 5A

```
            Leu Leu Met Asp Leu Asp Ile Ser Met Arg Thr Val Asp Cys Pro Phe>

580     585     590     595     600     605     610     615     620
               *               *               *               *               *
            ACT GTC ACC TTT TAT GGC GCA CTG TTT CGG GAG GGT GAT GTG TGG ATC
            TGA CAG TGG AAA ATA CCG CGT GAC AAA GCC CTC CCA CTA CAC ACC TAG
            Thr Val Thr Phe Tyr Gly Ala Leu Phe Arg Glu Gly Asp Val Trp Ile>

625     630     635     640     645     650     655     660     665     670
         *               *               *               *               *
        TGC ATG GAG CTC ATG GAT ACA TCA CTA GAT AAA TTC TAC AAA CAA GTT
        ACG TAC CTC GAG TAC CTA TGT AGT GAT CTA TTT AAG ATG TTT GTT CAA
        Cys Met Glu Leu Met Asp Thr Ser Leu Asp Lys Phe Tyr Lys Gln Val>

675     680     685     690     695     700     705     710     715     720
           *               *               *               *               *
        ATT GAT AAA GGC CAG ACA ATT CCA GAG GAC ATC TTA GGG AAA ATA GCA
        TAA CTA TTT CCG GTC TGT TAA GGT CTC CTG TAG AAT CCC TTT TAT CGT
        Ile Asp Lys Gly Gln Thr Ile Pro Glu Asp Ile Leu Gly Lys Ile Ala>

725     730     735     740     745     750     755     760     765
             *               *               *               *
        GTT TCT ATT GTA AAA GCA TTA GAA CAT TTA CAT AGT AAG CTG TCT GTC
        CAA AGA TAA CAT TTT CGT AAT CTT GTA AAT GTA TCA TTC GAC AGA CAG
        Val Ser Ile Val Lys Ala Leu Glu His Leu His Ser Lys Leu Ser Val>

770     775     780     785     790     795     800     805     810     815
         *               *               *               *               *
        ATT CAC AGA GAC GTC AAG CCT TCT AAT GTA CTC ATC AAT GCT CTC GGT
        TAA GTG TCT CTG CAG TTC GGA AGA TTA CAT GAG TAG TTA CGA GAG CCA
        Ile His Arg Asp Val Lys Pro Ser Asn Val Leu Ile Asn Ala Leu Gly>

820     825     830     835     840     845     850     855     860
             *               *               *               *               *
        CAA GTG AAG ATG TGC GAT TTT GGA ATC AGT GGC TAC TTG GTG GAC TCT
        GTT CAC TTC TAC ACG CTA AAA CCT TAG TCA CCG ATG AAC CAC CTG AGA
        Gln Val Lys Met Cys Asp Phe Gly Ile Ser Gly Tyr Leu Val Asp Ser>

865     870     875     880     885     890     895     900     905     910
         *               *               *               *               *
        GTT GCT AAA ACA ATT GAT GCA GGT TGC AAA CCA TAC ATG GCC CCT GAA
        CAA CGA TTT TGT TAA CTA CGT CCA ACG TTT GGT ATG TAC CGG GGA CTT
        Val Ala Lys Thr Ile Asp Ala Gly Cys Lys Pro Tyr Met Ala Pro Glu>

915     920     925     930     935     940     945     950     955     960
         *               *               *               *               *
        AGA ATA AAC CCA GAG CTC AAC CAG AAG GGA TAC AGT GTG AAG TCT GAC
        TCT TAT TTG GGT CTC GAG TTG GTC TTC CCT ATG TCA CAC TTC AGA CTG
        Arg Ile Asn Pro Glu Leu Asn Gln Lys Gly Tyr Ser Val Lys Ser Asp>

965     970     975     980     985     990     995    1000    1005
             *               *               *               *
        ATT TGG AGT CTG GGC ATC ACG ATG ATT GAG TTG GCC ATC CTT CGA TTT
        TAA ACC TCA GAC CCG TAG TGC TAC TAA CTC AAC CGG TAG GAA GCT AAA
        Ile Trp Ser Leu Gly Ile Thr Met Ile Glu Leu Ala Ile Leu Arg Phe>

1010    1015    1020    1025    1030    1035    1040    1045    1050    1055
         *               *               *               *               *
        CCC TAT GAT TCA TGG GGA ACT CCA TTT CAG CAG CTC AAA CAG GTG GTA
        GGG ATA CTA AGT ACC CCT TGA GGT AAA GTC GTC GAG TTT GTC CAC CAT
        Pro Tyr Asp Ser Trp Gly Thr Pro Phe Gln Gln Leu Lys Gln Val Val>
```

FIG. 5B

```
     1060      1065      1070      1075      1080      1085      1090      1095      1100
       *                   *                   *                   *                   *
GAG GAG CCA TCG CCA CAA CTC CCA GCA GAC AAG TTC TCT GCA GAG TTT
CTC CTC GGT AGC GGT GTT GAG GGT CGT CTG TTC AAG AGA CGT CTC AAA
Glu Glu Pro Ser Pro Gln Leu Pro Ala Asp Lys Phe Ser Ala Glu Phe>

1105  1110     1115     1120     1125     1130     1135     1140     1145     1150
            *              *              *              *              *
GTT GAC TTT ACC TCA CAG TGC TTA AAG AAG AAT TCC AAA GAA CGG CCT
CAA CTG AAA TGG AGT GTC ACG AAT TTC TTC TTA AGG TTT CTT GCC GGA
Val Asp Phe Thr Ser Gln Cys Leu Lys Lys Asn Ser Lys Glu Arg Pro>

1155     1160     1165     1170     1175     1180     1185     1190     1195     1200
        *              *              *              *              *
ACA TAC CCA GAG CTA ATG CAA CAT CCA TTT TTC ACC CTA CAT GAA TCC
TGT ATG GGT CTC GAT TAC GTT GTA GGT AAA AAG TGG GAT GTA CTT AGG
Thr Tyr Pro Glu Leu Met Gln His Pro Phe Phe Thr Leu His Glu Ser>

1205     1210     1215     1220     1225     1230     1235     1240     1245     1250
           *              *              *              *              *
AAA GGA ACA GAT GTG GCA TCT TTT GTA AAA CTG ATT CTT GGA GAC TAAAA
TTT CCT TGT CTA CAC CGT AGA AAA CAT TTT GAC TAA GAA CCT CTG ATTTT
Lys Gly Thr Asp Val Ala Ser Phe Val Lys Leu Ile Leu Gly Asp> (SEQ ID NO:4)

1255 1260    1265 1270    1275 1280    1285 1290    1295 1300    1305 1310
             *              *              *              *              *
AGCAGTGGAC  TTAATCGGTT  GACCCTACTG  TGGATTGGTG  GGTTTCGGGG  TGAAGCAAGT
TCGTCACCTG  AATTAGCCAA  CTGGGATGAC  ACCTAACCAC  CCAAAGCCCC  ACTTCGTTCA 1315 1320    1325 1330    1335 1340    1345 1350    1355 1360    1365 1370
             *              *              *              *              *
TCACTACAGC  ATCAATAGAA  AGTCATCTTT  GAGATAATTT  AACCCTGCCT  CTCAGAGGGT
AGTGATGTCG  TAGTTATCTT  TCAGTAGAAA  CTCTATTAAA  TTGGGACGGA  GAGTCTCCCA 1375 1380    1385 1390    1395 1400    1405 1410    1415 1420    1425 1430
             *              *              *              *              *
TTTCTCTCCC  AATTTTCTTT  TTACTCCCCC  TCTTAAGGGG  GCCTTGGAAT  CTATAGTATA
AAAGAGAGGG  TTAAAAGAAA  AATGAGGGGG  AGAATTCCCC  CGGAACCTTA  GATATCATAT 1435 1440    1445 1450    1455 1460    1465 1470    1475 1480    1485 1490
             *              *              *              *              *
GAATGAACTG  TCTAGATGGA  TGAATTATGA  TAAAGGCTTA  GGACTTCAAA  AGGTGATTAA
CTTACTTGAC  AGATCTACCT  ACTTAATACT  ATTTCCGAAT  CCTGAAGTTT  TCCACTAATT 1495 1500    1505 1510    1515 1520    1525 1530    1535 1540    1545 1550
             *              *              *              *              *
ATATTTAATG  ATGTGTCATA  TGAGTCCTCA  AAAAAAAAAA  AAAAAAAAAA  AAAAAAAAAA
TATAAATTAC  TACACAGTAT  ACTCAGGAGT  TTTTTTTTTT  TTTTTTTTTT  TTTTTTTTTT 1555 1560    1565 1570    1575 1580    1585 1590    1595 1600
             *              *              *              *
AAAAAAAAAA  AAAAAAAAAA  AAAAAAAAAA  AAAAAAAAAA  AAAAAAAAAA  AA  (SEQ ID NO:3)
TTTTTTTTTT  TTTTTTTTTT  TTTTTTTTTT  TTTTTTTTTT  TTTTTTTTTT  TT
```

FIG. 5C

```
         5         10        15        20        25        30        35        40        45        50    55
         *                   *                   *                   *                   *
CTAGGGTCCC CGGCGCCAGG CCACCCGGCC GTCAGCAGC ATG CAG GGT AAA CGC AAA
GATCCCAGGG GCCGCGGTCC GGTGGGCCGG CAGTCGTCG TAC GTC CCA TTT GCG TTT
                                          Met Gln Gly Lys Arg Lys>

60        65        70        75        80        85        90        95        100       105
   *                   *                   *                   *                   *
GCA CTG AAG TTG AAT TTT GCA AAT CCA CCT TTC AAA TCT ACA GCA AGG
CGT GAC TTC AAC TTA AAA CGT TTA GGT GGA AAG TTT AGA TGT CGT TCC
Ala Leu Lys Leu Asn Phe Ala Asn Pro Pro Phe Lys Ser Thr Ala Arg>

110       115       120       125       130       135       140       145       150
        *                   *                   *                   *                   *
TTT ACT CTG AAT CCC AAT CCT ACA GGA GTT CAA AAC CCA CAC ATA GAG
AAA TGA GAC TTA GGG TTA GGA TGT CCT CAA GTT TTG GGT GTG TAT CTC
Phe Thr Leu Asn Pro Asn Pro Thr Gly Val Gln Asn Pro His Ile Glu>

155       160       165       170       175       180       185       190       195       200
                *                   *                   *                   *                   *
AGA CTG AGA ACA CAC AGC ATT GAG TCA TCA GGA AAA CTG AAG ATC TCC
TCT GAC TCT TGT GTG TCG TAA CTC AGT AGT CCT TTT GAC TTC TAG AGG
Arg Leu Arg Thr His Ser Ile Glu Ser Ser Gly Lys Leu Lys Ile Ser>

205       210       215       220       225       230       235       240       245
                *                   *                   *                   *
CCT GAA CAA CAC TGG GAT TTC ACT GCA GAG GAC TTG AAA GAC CTT GGA
GGA CTT GTT GTG ACC CTA AAG TGA CGT CTC CTG AAC TTT CTG GAA CCT
Pro Glu Gln His Trp Asp Phe Thr Ala Glu Asp Leu Lys Asp Leu Gly>

250       255       260       265       270       275       280       285       290       295
*                   *                   *                   *                   *
GAA ATT GGA CGA GGA GCT TAT GGT TCT GTC AAC AAA ATG GTC CAC AAA
CTT TAA CCT GCT CCT CGA ATA CCA AGA CAG TTG TTT TAC CAG GTG TTT
Glu Ile Gly Arg Gly Ala Tyr Gly Ser Val Asn Lys Met Val His Lys>

300       305       310       315       320       325       330       335       340       345
                *                   *                   *                   *                   *
CCA AGT GGG CAA ATA ATG GCA GTT AAA AGA ATT CGG TCA ACA GTG GAT
GGT TCA CCC GTT TAT TAC CGT CAA TTT TCT TAA GCC AGT TGT CAC CTA
Pro Ser Gly Gln Ile Met Ala Val Lys Arg Ile Arg Ser Thr Val Asp>

350       355       360       365       370       375       380       385       390
        *                   *                   *                   *
GAA AAA GAA CAA AAA CAA CTT CTT ATG GAT TTG GAT GTA GTA ATG CGG
CTT TTT CTT GTT TTT GTT GAA GAA TAC CTA AAC CTA CAT CAT TAC GCC
Glu Lys Glu Gln Lys Gln Leu Leu Met Asp Leu Asp Val Val Met Arg>

395       400       405       410       415       420       425       430       435       440
    *                   *                   *                   *                   *
AGT AGT GAT TGC CCA TAC ATT GTT CAG TTT TAT GGT GCA CTC TTC AGA
TCA TCA CTA ACG GGT ATG TAA CAA GTC AAA ATA CCA CGT GAG AAG TCT
Ser Ser Asp Cys Pro Tyr Ile Val Gln Phe Tyr Gly Ala Leu Phe Arg>

445       450       455       460       465       470       475       480       485
                *                   *                   *                   *
GAG GGT GAC TGT TGG ATC TGT ATG GAA CTC ATG TCT ACC TCG TTT GAT
CTC CCA CTG ACA ACC TAG ACA TAC CTT GAG TAC AGA TGG AGC AAA CTA
Glu Gly Asp Cys Trp Ile Cys Met Glu Leu Met Ser Thr Ser Phe Asp>
```

FIG. 6A

```
     490      495       500       505       510       515       520       525       530       535
      *                  *                   *                   *                   *
     AAG  TTT  TAC  AAA  TAT  GTA  TAT  AGT  GTA  TTA  GAT  GAT  GTT  ATT  CCA  GAA
     TTC  AAA  ATG  TTT  ATA  CAT  ATA  TCA  CAT  AAT  CTA  CTA  CAA  TAA  GGT  CTT
     Lys  Phe  Tyr  Lys  Tyr  Val  Tyr  Ser  Val  Leu  Asp  Asp  Val  Ile  Pro  Glu>

540      545       550       555       560       565       570       575       580       585
      *                  *                   *                   *                   *
     GAA  ATT  TTA  GGC  AAA  ATC  ACT  TTA  GCA  ACT  GTG  AAA  GCA  CTA  AAC  CAC
     CTT  TAA  AAT  CCG  TTT  TAG  TGA  AAT  CGT  TGA  CAC  TTT  CGT  GAT  TTG  GTG
     Glu  Ile  Leu  Gly  Lys  Ile  Thr  Leu  Ala  Thr  Val  Lys  Ala  Leu  Asn  His>

590      595       600       605       610       615       620       625       630
          *                  *                   *                   *                   *
         TTA  AAA  GAA  AAC  TTG  AAA  ATT  ATT  CAC  AGA  GAT  ATC  AAA  CCT  TCC  AAT
         AAT  TTT  CTT  TTG  AAC  TTT  TAA  TAA  GTG  TCT  CTA  TAG  TTT  GGA  AGG  TTA
         Leu  Lys  Glu  Asn  Leu  Lys  Ile  Ile  His  Arg  Asp  Ile  Lys  Pro  Ser  Asn>

635      640       645       650       655       660       665       670       675       680
      *                  *                   *                   *                   *
     ATT  CTT  CTG  GAC  AGA  AGT  GGA  AAT  ATT  AAG  CTC  TGT  GAC  TTC  GGC  ATC
     TAA  GAA  GAC  CTG  TCT  TCA  CCT  TTA  TAA  TTC  GAG  ACA  CTG  AAG  CCG  TAG
     Ile  Leu  Leu  Asp  Arg  Ser  Gly  Asn  Ile  Lys  Leu  Cys  Asp  Phe  Gly  Ile>

685      690       695       700       705       710       715       720       725
      *                  *                   *                   *                   *
     AGT  GGA  CAG  CTT  GTG  GAC  TCT  ATT  GCC  AAG  ACA  AGA  GAT  GCT  GGC  TGT
     TCA  CCT  GTC  GAA  CAC  CTG  AGA  TAA  CGG  TTC  TGT  TCT  CTA  CGA  CCG  ACA
     Ser  Gly  Gln  Leu  Val  Asp  Ser  Ile  Ala  Lys  Thr  Arg  Asp  Ala  Gly  Cys>

730      735       740       745       750       755       760       765       770       775
      *                  *                   *                   *                   *
     AGG  CCA  TAC  ATG  GCA  CCT  GAA  AGA  ATA  GAC  CCA  AGC  GCA  TCA  CGA  CAA
     TCC  GGT  ATG  TAC  CGT  GGA  CTT  TCT  TAT  CTG  GGT  TCG  CGT  AGT  GCT  GTT
     Arg  Pro  Tyr  Met  Ala  Pro  Glu  Arg  Ile  Asp  Pro  Ser  Ala  Ser  Arg  Gln>

780      785       790       795       800       805       810       815       820       825
      *                  *                   *                   *                   *
     GGA  TAT  GAT  GTC  CGC  TCT  GAT  GTC  TGG  AGT  TTG  GGG  ATC  ACA  TTG  TAT
     CCT  ATA  CTA  CAG  GCG  AGA  CTA  CAG  ACC  TCA  AAC  CCC  TAG  TGT  AAC  ATA
     Gly  Tyr  Asp  Val  Arg  Ser  Asp  Val  Trp  Ser  Leu  Gly  Ile  Thr  Leu  Tyr>

830      835       840       845       850       855       860       865       870
          *                  *                   *                   *                   *
         GAG  TTG  GCC  ACA  GGC  CGA  TTT  CCT  TAT  CCA  AAG  TGG  AAT  AGT  GTA  TTT
         CTC  AAC  CGG  TGT  CCG  GCT  AAA  GGA  ATA  GGT  TTC  ACC  TTA  TCA  CAT  AAA
         Glu  Leu  Ala  Thr  Gly  Arg  Phe  Pro  Tyr  Pro  Lys  Trp  Asn  Ser  Val  Phe>

875      880       885       890       895       900       905       910       915       920
      *                  *                   *                   *                   *
     GAT  CAA  CTA  ACA  CAA  GTC  GTG  AAA  GGA  GAT  CCT  CCG  CAG  CTG  AGT  AAT
     CTA  GTT  GAT  TGT  GTT  CAG  CAC  TTT  CCT  CTA  GGA  GGC  GTC  GAC  TCA  TTA
     Asp  Gln  Leu  Thr  Gln  Val  Val  Lys  Gly  Asp  Pro  Pro  Gln  Leu  Ser  Asn>

925      930       935       940       945       950       955       960       965
      *                  *                   *                   *                   *
     TCT  GAG  GAA  AGG  GAA  TTC  TCC  CCG  AGT  TTC  ATC  AAC  TTT  GTC  AAC  TTG
     AGA  CTC  CTT  TCC  CTT  AAG  AGG  GGC  TCA  AAG  TAG  TTG  AAA  CAG  TTG  AAC
     Ser  Glu  Glu  Arg  Glu  Phe  Ser  Pro  Ser  Phe  Ile  Asn  Phe  Val  Asn  Leu>

```
TGC CTT ACG AAG GAT GAA TCC AAA AGG CCA AAG TAT AAA GAG CTT CTG
ACG GAA TGC TTC CTA CTT AGG TTT TCC GGT TTC ATA TTT CTC GAA GAC
Cys Leu Thr Lys Asp Glu Ser Lys Arg Pro Lys Tyr Lys Glu Leu Leu>

1020   1025   1030   1035   1040   1045  1050   1055   1060  1065
  *             *             *             *             *

AAA CAT CCC TTT ATT TTG ATG TAT GAA GAA CGT GCC GTT GAG GTC GCA
TTT GTA GGG AAA TAA AAC TAC ATA CTT CTT GCA CGG CAA CTC CAG CGT
Lys His Pro Phe Ile Leu Met Tyr Glu Glu Arg Ala Val Glu Val Ala>

1070   1075  1080   1085   1090  1095   1100   1105  1110
    *             *             *             *

TGC TAT GTT TGT AAA ATC CTG GAT CAA ATG CCA GCT ACT CCC AGC TCT
ACG ATA CAA ACA TTT TAG GAC CTA GTT TAC GGT CGA TGA GGG TCG AGA
Cys Tyr Val Cys Lys Ile Leu Asp Gln Met Pro Ala Thr Pro Ser Ser>

1115   1120  :125   1130   1135 1140  1145 1150   1155  1160   1165 1170
  *             *             *             *             *             *

CCC ATG TAT GTC GAT TG ATATCGYTGC TACATCAGAC TCTAGAAAAA AGGGCTGAGA
GGG TAC ATA CAG CTA AC TATAGCRACG ATGTAGTCTG AGATCTTTTT TCCCGACTCT
Pro Met Tyr Val Asp>  (SEQ ID NO:6)

1175 1180   1185 1190   1195 1200   1205 1210   1215 1220   1225 1230
        *             *             *             *             *             *

GGAAGCAAGA CGTAAAGAAT TTTCATCCCG TATCACAGTG TTTTTATTGC TCGCCCAGAC
CCTTCGTTCT GCATTTCTTA AAAGTAGGGC ATAGTGTCAC AAAAATAACG AGCGGGTCTG 1235 1240   1245 1250   1255 1260   1265 1270   1275 1280   1285 1290
        *             *             *             *             *             *

ACCATGTGCA ATAAGATTGG TGTTCGTTTC CATCATGTCT GTATACTCCT GTCACCTAGA
TGGTACACGT TATTCTAACC ACAAGCAAAG GTAGTACAGA CATATGAGGA CAGTGGATCT 1295 1300   1305 1310   1315 1320   1325 1330   1335 1340   1345 1350
        *             *             *             *             *             *

ACGTGCATCC TTGTAATACC TGATTGATCA CACAGTGTTA GTGCTGGTCA GAGAGACCTC
TGCACGTAGG AACATTATGG ACTAACTAGT GTGTCACAAT CACGACCAGT CTCTCTGGAG 1355 1360   1365 1370   1375 1380   1385 1390   1395 1400   1405 1410
        *             *             *             *             *             *

ATCCTGCTCT TTTGTGATGA ACATATTCAT GAAATGTGGA AGTCAGTACG ATCAAGTTGT
TAGGACGAGA AAACACTACT TGTATAAGTA CTTTACACCT TCAGTCATGC TAGTTCAACA 1415 1420   1425 1430   1435 1440   1445 1450   1455 1460   1465 1470
        *             *             *             *             *             *

TGACTGTGAT TAGATCACAT CTTAAATTCA TTTCTAGACT CAAAACCTGG AGATGCAGCT
ACTGACACTA ATCTAGTGTA GAATTTAAGT AAAGATCTGA GTTTTGGACC TCTACGTCGA 1475 1480   1485 1490   1495 1500   1505 1510   1515 1520   1525 1530
        *             *             *             *             *             *

ACTGGAATGG TGTTTTGTCA GACTTCCAAA TCCTGGAAGG ACACAGTGAT GAATGTACTA
TGACCTTACC ACAAAACAGT CTGAAGGTTT AGGACCTTCC TGTGTCACTA CTTACATGAT 1535 1540   1545 1550   1555 1560   1565 1570   1575 1580   1585 1590
        *             *             *             *             *             *

TATCTGAACA TAGAAACTCG GGCTTGAGTG AGAAGAGCTT GCACAGCCAA CGAGACACAT
ATAGACTTGT ATCTTTGAGC CCGAACTCAC TCTTCTCGAA CGTGTCGGTT GCTCTGTGTA 1595 1600   1605 1610   1615 1620   1625 1630   1635 1640   1645 1650
        *             *             *             *             *             *

TGCCTTCTGG AGCTGGGAGA CAAAGGAGGA ATTTACTTTC TTCACCAAGT GCAATAGATT
ACGGAAGACC TCGACCCTCT GTTTCCTCCT TAAATGAAAG AAGTGGTTCA CGTTATCTAA
```

FIG. 6C

```
1655 1660  1665 1670  1675 1680  1685 1690  1695 1700  1705 1710
         *          *          *          *          *          *
ACTGATGTGA TATTCTGTTG CTTTACAGTT ACAGTTGATG TTTGGGGATC GATGTGCTCA
TGACTACACT ATAAGACAAC GAAATGTCAA TGTCAACTAC AAACCCCTAG CTACACGAGT 1715 1720  1725 1730  1735 1740  1745 1750  1755 1760  1765 1770
         *          *          *          *          *          *
GCCAAATTTC CTGTTTGAAA TATCATGTTA AATTAGAATG AATTTATCTT TACCAAAAAC
CGGTTTAAAG GACAAACTTT ATAGTACAAT TTAATCTTAC TTAAATAGAA ATGGTTTTTG 1775 1780  1785 1790  1795 1800  1805 1810  1815 1820  1825 1830
         *          *          *          *          *          *
CATGTTGCGT TCAAAGAGGT GAACATTAAA ATATAGAGAC AGGACAGAAT GTGTTCTTTT
GTACAACGCA AGTTTCTCCA CTTGTAATTT TATATCTCTG TCCTGTCTTA CACAAGAAAA 1835 1840  1845 1850  1855 1860  1865 1870  1875 1880  1885 1890
         *          *          *          *          *          *
CTCCTCTACC AGTCCTATTT TTCAATGGGA AGACTCAGGA GTCTGCCACT TGTCAAAGAA
GAGGAGATGG TCAGGATAAA AAGTTACCCT TCTGAGTCCT CAGACGGTGA ACAGTTTCTT 1895 1900  1905 1910  1915 1920  1925 1930  1935 1940  1945 1950
         *          *          *          *          *          *
GGTGCTGATC CTAAGAATTT TTCATTCTCA GAATTCGGTG TGCTGCCAAC TTGATGTTCC
CCACGACTAG GATTCTTAAA AAGTAAGAGT CTTAAGCCAC ACGACGGTTG AACTACAAGG 1955 1960  1965 1970  1975 1980  1985 1990  1995 2000  2005 2010
         *          *          *          *          *          *
ACCTGCCACA AACCACCAGG ACTGAAAGAA GAAAACAGTA CAGAAGGCAA AGTTTACAGA
TGGACGGTGT TTGGTGGTCC TGACTTTCTT CTTTTGTCAT GTCTTCCGTT TCAAATGTCT 2015 2020  2025 2030  2035 2040  2045 2050  2055 2060  2065 2070
         *          *          *          *          *          *
TGTTTTTAAT TCTAGTATTT TATCTGGAAC AACTTGTAGC AGCTATATAT TTCCCCTTGG
ACAAAAATTA AGATCATAAA ATAGACCTTG TTGAACATCG TCGATATATA AAGGGGAACC 2075 2080  2085 2090  2095 2100  2105 2110  2115 2120  2125 2130
         *          *          *          *          *          *
TCCCAAGCCT GATACTTTAG CCATCATAAC TCACTAACAG GGAGAAGTAG CTAGTAGCAA
AGGGTTCGGA CTATGAAATC GGTAGTATTG AGTGATTGTC CCTCTTCATC GATCATCGTT 2135 2140  2145 2150  2155 2160  2165 2170  2175 2180  2185 2190
         *          *          *          *          *          *
TGTGCCTTGA TTGATTAGAT AAAGATTTCT AGTAGGCAGC AAAAGACCAA ATCTCAGTTG
ACACGGAACT AACTAATCTA TTTCTAAAGA TCATCCGTCG TTTTCTGGTT TAGAGTCAAC 2195 2200  2205 2210  2215 2220  2225 2230  2235 2240  2245 2250
         *          *          *          *          *          *
TTTGCTTCTT GCCATCACTG GTCCAGGTCT TCAGTTTCCG AATCTCTTTC CCTTCCCCTG
AAACGAAGAA CGGTAGTGAC CAGGTCCAGA AGTCAAAGGC TTAGAGAAAG GGAAGGGGAC 2255 2260  2265 2270  2275 2280  2285 2290  2295 2300  2305 2310
         *          *          *          *          *          *
TGGTCTATTG TCGCTATGTG ACTTGCGCTT AATCCAATAT TTTGCCTTTT TTCTATATCA
ACCAGATAAC AGCGATACAC TGAACGCGAA TTAGGTTATA AAACGGAAAA AAGATATAGT 2315 2320  2325 2330  2335 2340  2345 2350  2355 2360  2365 2370
         *          *          *          *          *          *
AAAAACCTTT ACAGTTAGCA GGGATGTTCC TTACCGAGGA TTTTTAACCC CCAATCTCTC
TTTTTGGAAA TGTCAATCGT CCCTACAAGG AATGGCTCCT AAAAATTGGG GGTTAGAGAG 2375 2380  2385 2390  2395 2400  2405 2410  2415 2420  2425 2430
         *          *          *          *          *          *
```

FIG. 6D

```
ATAATCGCTA GTGTTTAAAA GGCTAAGAAT AGTGGGGCCC AACCGATGTG GTAGGTGATA
TATTAGCGAT CACAAATTTT CCGATTCTTA TCACCCCGGG TTGGCTACAC CATCCACTAT 2435 2440  2445 2450  2455 2460  2465 2470  2475 2480  2485 2490
        *           *          *          *          *          *
AAGAGGCATC TTTTCTAGAG ACACATTGGA CCAGATGAGG ATCCGAAACG GCAGCCTTTA
TTCTCCGTAG AAAAGATCTC TGTGTAACCT GGTCTACTCC TAGGCTTTGC CGTCGGAAAT 2495 2500  2505 2510  2515 2520  2525 2530  2535 2540  2545 2550
        *           *          *          *          *          *
CGTTCATCAC CTGCTAGAAC CTCTCGTAGT CCATCACCAT TTCTTGGCAT TGGAATTCTA
GCAAGTAGTG GACGATCTTG GAGAGCATCA GGTAGTGGTA AAGAACCGTA ACCTTAAGAT 2555 2560  2565 2570  2575 2580  2585 2590  2595 2600  2605 2610
        *           *          *          *          *          *
CTGGAAAAAA ATACAAAAAG CAAAACAAAA CCCTCAGCAC TGTTACAAGA GGCCATTTAA
GACCTTTTTT TATGTTTTTC GTTTTGTTTT GGGAGTCGTG ACAATGTTCT CCGGTAAATT 2615 2620  2625 2630  2635 2640  2645 2650  2655 2660  2665 2670
        *           *          *          *          *          *
GTATCTTGTG CTTCTTCACT TACCCATTAG CCAGGTTCTC ATTAGGTTTT GCTTGGGCCT
CATAGAACAC GAAGAAGTGA ATGGGTAATC GGTCCAAGAG TAATCCAAAA CGAACCCGGA 2675 2680  2685 2690  2695 2700  2705 2710  2715 2720  2725 2730
        *           *          *          *          *          *
CCCTGGCACT GAACCTTAGG CTTTGTATGA CAGTGAAGCA GCACTGTGAG TGGTTCAAGC
GGGACCGTGA CTTGGAATCC GAAACATACT GTCACTTCGT CGTGACACTC ACCAAGTTCG 2735 2740  2745 2750  2755 2760  2765 2770  2775 2780  2785 2790
        *           *          *          *          *          *
ACACTGGAAT ATAAAACAGT CATGGCCTGA GATGCAGGTG ATGCCATTAC AGAACCAAAT
TGTGACCTTA TATTTTGTCA GTACCGGACT CTACGTCCAC TACGGTAATG TCTTGGTTTA 2795 2800  2805 2810  2815 2820  2825 2830  2835 2840  2845 2850
        *           *          *          *          *          *
CGTGGCACGT ATTGCTGTGT CTCCTCTCAG AGTGACAGTC ATAAATACTG TCAAACAATA
GCACCGTGCA TAACGACACA GAGGAGAGTC TCACTGTCAG TATTTATGAC AGTTTGTTAT 2855 2860  2865 2870  2875 2880  2885 2890  2895 2900  2905 2910
        *           *          *          *          *          *
AAGGGAGAAT GGTGCTGTTT AAAGTCACAT CCCTGTAAAT TGCAGAATTC AAAAGTGATT
TTCCCTCTTA CCACGACAAA TTTCAGTGTA GGGACATTTA ACGTCTTAAG TTTTCACTAA 2915 2920  2925 2930  2935 2940  2945 2950  2955 2960  2965 2970
        *           *          *          *          *          *
ATCTCTTTGA TCTACTTGCC TCATTTCCCT ATCTTCTCCC CCACGGTATC CTAAACTTTA
TAGAGAAACT AGATGAACGG AGTAAAGGGA TAGAAGAGGG GGTGCCATAG GATTTGAAAT 2975 2980  2985 2990  2995 3000  3005 3010  3015 3020  3025 3030
        *           *          *          *          *          *
GACTTCCCAC TGTTCTGAAA GGAGACATTG CTCTATGTCT GCCTTCGACC ACAGCAAGCC
CTGAAGGGTG ACAAGACTTT CCTCTGTAAC GAGATACAGA CGGAAGCTGG TGTCGTTCGG 3035 3040  3045 3050  3055 3060  3065 3070  3075 3080  3085 3090
        *           *          *          *          *          *
ATCATCCTCC ATTGCTCCCG GGGACTCAAG AGGAATCTGT TTCTCTGCTG TCAACTTCCC
TAGTAGGAGG TAACGAGGGC CCCTGAGTTC TCCTTAGACA AAGAGACGAC AGTTGAAGGG 3095 3100  3105 3110  3115 3120  3125 3130  3135 3140  3145 3150
        *           *          *          *          *          *
ATCTGGCTCA GCATAGGGTC ACTTTGCCAT TATGCAAATG GAGATAAAAG CAATTCTGGC
TAGACCGAGT CGTATCCCAG TGAAACGGTA ATACGTTTAC CTCTATTTTC GTTAAGACCG
```

FIG. 6E

```
              3155 3160    3165 3170    3175 3180    3185 3190    3195 3200    3205 3210
                  *            *            *            *            *            *
              TGTCCAGGAG   CTAATCTGAC   CGTTCTATTG   TGTGGATGAC   CACATAAGAA   GGCAATTTTA
              ACAGGTCCTC   GATTAGACTG   GCAAGATAAC   ACACCTACTG   GTGTATTCTT   CCGTTAAAAT 3215 3220    3225 3230    3235 3240    3245 3250    3255 3260    3265 3270
                  *            *            *            *            *            *
              GTGTATTAAT   CATAGATTAT   TATAAACTAT   AAACTTAAGG   GCAAGGAGTT   TATTACAATG
              CACATAATTA   GTATCTAATA   ATATTTGATA   TTTGAATTCC   CGTTCCTCAA   ATAATGTTAC 3275 3280    3285 3290    3295 3300    3305 3310    3315 3320    3325 3330
                  *            *            *            *            *            *
              TATCTTTATT   AAAACAAAAG   GGTGTATAGT   GTTCACAAAC   TGTGAAAATA   GTGTAAGAAC
              ATAGAAATAA   TTTTGTTTTC   CCACATATCA   CAAGTGTTTG   ACACTTTTAT   CACATTCTTG 3335 3340    3345 3350    3355 3360    3365 3370    3375 3380    3385 3390
                  *            *            *            *            *            *
              TGTACATTGT   GAGCTCTGGT   TATTTTTCTC   TTGTACCATA   GAAAAATGTA   TAAAAATTAT
              ACATGTAACA   CTCGAGACCA   ATAAAAAGAG   AACATGGTAT   CTTTTTACAT   ATTTTTAATA 3395 3400    3405 3410    3415 3420    3425 3430    3435 3440    3445 3450
                  *            *            *            *            *            *
              CAAAAAGCTA   ATGTGCAGGG   ATATTGCCTT   ATTTGTCTGT   AAAAAATGGA   GCTCAGTAAC
              GTTTTTCGAT   TACACGTCCC   TATAACGGAA   TAAACAGACA   TTTTTTACCT   CGAGTCATTG 3455 3460    3465 3470    3475 3480    3485 3490    3495
                  *            *            *            *
              ATAACTGCTT   CTTGGAGCTT   TGGAATATTT   TATCCTGTAT   TCTTGTTT    (SEQ ID NO:5)
              TATTGACGAA   GAACCTCGAA   ACCTTATAAA   ATAGGACATA   AGAACAAA
```

FIG. 6F

```
       5        10        15        20        25        30        35        40        45       50
                                    *                            *                            *
     CAACA ATG GCG GCT CCG AGC CCG AGC GGT GGC GGC GGC AGC GGC ACC CCC
     GTTGT TAC CGC CGA GGC TCG GGC TCG CCA CCG CCG CCG TCG CCG TGG GGG
           Met Ala Ala Pro Ser Pro Ser Gly Gly Gly Gly Ser Gly Thr Pro>

55        60        65        70        75        80        85        90        95
                    *                            *                            *
     GGC CCC GTA GGG TCC CCG GCG CCA GGC CAC CCG GCC GTC AGC AGC ATG
     CCG GGG CAT CCC AGG GGC CGC GGT CCG GTG GGC CGG CAG TCG TCG TAC
     Gly Pro Val Gly Ser Pro Ala Pro Gly His Pro Ala Val Ser Ser Met>

100       105       110       115       120       125       130       135       140      145
      *                            *                            *
     CAG GGT AAA CGC AAA GCA CTG AAG TTG AAT TTT GCA AAT CCA CCT TTC
     GTC CCA TTT GCG TTT CGT GAC TTC AAC TTA AAA CGT TTA GGT GGA AAG
     Gln Gly Lys Arg Lys Ala Leu Lys Leu Asn Phe Ala Asn Pro Pro Phe>

150       155       160       165       170       175       180       185       190
          *                            *                            *                    *
     AAA TCT ACA GCA AGG TTT ACT CTG AAT CCC AAT CCT ACA GGA GTT CAA
     TTT AGA TGT CGT TCC AAA TGA GAC TTA GGG TTA GGA TGT CCT CAA GTT
     Lys Ser Thr Ala Arg Phe Thr Leu Asn Pro Asn Pro Thr Gly Val Gln>

195       200       205       210       215       220       225       230       235      240
      *                            *                            *                            *
     AAC CCA CAC ATA GAG AGA CTG AGA ACA CAC AGC ATT GAG TCA TCA GGA
     TTG GGT GTG TAT CTC TCT GAC TCT TGT GTG TCG TAA CTC AGT AGT CCT
     Asn Pro His Ile Glu Arg Leu Arg Thr His Ser Ile Glu Ser Ser Gly>

245       250       255       260       265       270       275       280       285      290
      *                  *                            *                            *        *
     AAA CTG AAG ATC TCC CCT GAA CAA CAC TGG GAT TTC ACT GCA GAG GAC
     TTT GAC TTC TAG AGG GGA CTT GTT GTG ACC CTA AAG TGA CGT CTC CTG
     Lys Leu Lys Ile Ser Pro Glu Gln His Trp Asp Phe Thr Ala Glu Asp>

295       300       305       310       315       320       325       330       335
                      *                            *                            *
     TTG AAA GAC CTT GGA GAA ATT GGA CGA GGA GCT TAT GGT TCT GTC AAC
     AAC TTT CTG GAA CCT CTT TAA CCT GCT CCT CGA ATA CCA AGA CAG TTG
     Leu Lys Asp Leu Gly Glu Ile Gly Arg Gly Ala Tyr Gly Ser Val Asn>

340       345       350       355       360       365       370       375       380      385
      *                  *                            *                            *        *
     AAA ATG GTC CAC AAA CCA AGT GGG CAA ATA ATG GCA GTT AAA AGA ATT
     TTT TAC CAG GTG TTT GGT TCA CCC GTT TAT TAC CGT CAA TTT TCT TAA
     Lys Met Val His Lys Pro Ser Gly Gln Ile Met Ala Val Lys Arg Ile>

390       395       400       405       410       415       420       425       430
                      *                            *                            *            *
     CGG TCA ACA GTG GAT GAA AAA GAA CAA AAA CAA CTT CTT ATG GAT TTG
     GCC AGT TGT CAC CTA CTT TTT CTT GTT TTT GTT GAA GAA TAC CTA AAC
     Arg Ser Thr Val Asp Glu Lys Glu Gln Lys Gln Leu Leu Met Asp Leu>

435       440       445       450       455       460       465       470       475      480
      *                            *                            *                            *
     GAT GTA GTA ATG CGG AGT AGT GAT TGC CCA TAC ATT GTT CAG TTT TAT
     CTA CAT CAT TAC GCC TCA TCA CTA ACG GGT ATG TAA CAA GTC AAA ATA
     Asp Val Val Met Arg Ser Ser Asp Cys Pro Tyr Ile Val Gln Phe Tyr>
```

FIG. 7A

```
      485       490       495       500       505       510       515       520       525       530
       *                   *                   *                   *                   *
GGT GCA CTC TTC AGA GAG GGT GAC TGT TGG ATC TGT ATG GAA CTC ATG
CCA CGT GAG AAG TCT CTC CCA CTG ACA ACC TAG ACA TAC CTT GAG TAC
Gly Ala Leu Phe Arg Glu Gly Asp Cys Trp Ile Cys Met Glu Leu Met>

535       540       545       550       555       560       565       570       575
            *                   *                   *                   *
   TCT ACC TCG TTT GAT AAG TTT TAC AAA TAT GTA TAT AGT GTA TTA GAT
   AGA TGG AGC AAA CTA TTC AAA ATG TTT ATA CAT ATA TCA CAT AAT CTA
   Ser Thr Ser Phe Asp Lys Phe Tyr Lys Tyr Val Tyr Ser Val Leu Asp>

580       585       590       595       600       605       610       615       620       625
   *                   *                   *                   *                   *
GAT GTT ATT CCA GAA GAA ATT TTA GGC AAA ATC ACT TTA GCA ACT GTG
CTA CAA TAA GGT CTT CTT TAA AAT CCG TTT TAG TGA AAT CGT TGA CAC
Asp Val Ile Pro Glu Glu Ile Leu Gly Lys Ile Thr Leu Ala Thr Val>

630       635       640       645       650       655       660       665       670
        *                   *                   *                   *
   AAA GCA CTA AAC CAC TTA AAA GAA AAC TTG AAA ATT ATT CAC AGA GAT
   TTT CGT GAT TTG GTG AAT TTT CTT TTG AAC TTT TAA TAA GTG TCT CTA
   Lys Ala Leu Asn His Leu Lys Glu Asn Leu Lys Ile Ile His Arg Asp>

675       680       685       690       695       700       705       710       715       720
 *                   *                   *                   *                   *
ATC AAA CCT TCC AAT ATT CTT CTG GAC AGA AGT GGA AAT ATT AAG CTC
TAG TTT GGA AGG TTA TAA GAA GAC CTG TCT TCA CCT TTA TAA TTC GAG
Ile Lys Pro Ser Asn Ile Leu Leu Asp Arg Ser Gly Asn Ile Lys Leu>

725       730       735       740       745       750       755       760       765       770
    *                   *                   *                   *                   *
TGT GAC TTC GGC ATC AGT GGA CAG CTT GTG GAC TCT ATT GCC AAG ACA
ACA CTG AAG CCG TAG TCA CCT GTC GAA CAC CTG AGA TAA CGG TTC TGT
Cys Asp Phe Gly Ile Ser Gly Gln Leu Val Asp Ser Ile Ala Lys Thr>

775       780       785       790       795       800       805       810       815
             *                   *                   *                   *
   AGA GAT GCT GGC TGT AGG CCA TAC ATG GCA CCT GAA AGA ATA GAC CCA
   TCT CTA CGA CCG ACA TCC GGT ATG TAC CGT GGA CTT TCT TAT CTG GGT
   Arg Asp Ala Gly Cys Arg Pro Tyr Met Ala Pro Glu Arg Ile Asp Pro>

820       825       830       835       840       845       850       855       860       865
 *                   *                   *                   *                   *
AGC GCA TCA CGA CAA GGA TAT GAT GTC CGC TCT GAT GTC TGG AGT TTG
TCG CGT AGT GCT GTT CCT ATA CTA CAG GCG AGA CTA CAG ACC TCA AAC
Ser Ala Ser Arg Gln Gly Tyr Asp Val Arg Ser Asp Val Trp Ser Leu>

870       875       880       885       890       895       900       905       910
        *                   *                   *                   *                   *
   GGG ATC ACA TTG TAT GAG TTG GCC ACA GGC CGA TTT CCT TAT CCA AAG
   CCC TAG TGT AAC ATA CTC AAC CGG TGT CCG GCT AAA GGA ATA GGT TTC
   Gly Ile Thr Leu Tyr Glu Leu Ala Thr Gly Arg Phe Pro Tyr Pro Lys>

915       920       925       930       935       940       945       950       955       960
 *                   *                   *                   *                   *
TGG AAT AGT GTA TTT GAT CAA CTA ACA CAA GTC GTG AAA GGA GAT CCT
ACC TTA TCA CAT AAA CTA GTT GAT TGT GTT CAG CAC TTT CCT CTA GGA
Trp Asn Ser Val Phe Asp Gln Leu Thr Gln Val Val Lys Gly Asp Pro>

```
CCG CAG CTG AGT AAT TCT GAG GAA AGG GAA TTC TCC CCG AGT TTC ATC
GGC GTC GAC TCA TTA AGA CTC CTT TCC CTT AAG AGG GGC TCA AAG TAG
Pro Gln Leu Ser Asn Ser Glu Glu Arg Glu Phe Ser Pro Ser Phe Ile>
     1015     1020  1025     1030     1035  1040     1045     1050  1055
       *               *               *               *
AAC TTT GTC AAC TTG TGC CTT ACG AAG GAT GAA TCC AAA AGG CCA AAG
TTG AAA CAG TTG AAC ACG GAA TGC TTC CTA CTT AGG TTT TCC GGT TTC
Asn Phe Val Asn Leu Cys Leu Thr Lys Asp Glu Ser Lys Arg Pro Lys>
1060     1065  1070     1075     1080  1085     1090     1095  1100     1105
  *               *               *               *               *
TAT AAA GAG CTT CTG AAA CAT CCC TTT ATT TTG ATG TAT GAA GAA CGT
ATA TTT CTC GAA GAC TTT GTA GGG AAA TAA AAC TAC ATA CTT CTT GCA
Tyr Lys Glu Leu Leu Lys His Pro Phe Ile Leu Met Tyr Glu Glu Arg>
    1110  1115     1120     1125  1130     1135     1140  1145     1150
             *               *               *               *               *
GCC GTT GAG GTC GCA TGC TAT GTT TGT AAA ATC CTG GAT CAA ATG CCA
CGG CAA CTC CAG CGT ACG ATA CAA ACA TTT TAG GAC CTA GTT TAC GGT
Ala Val Glu Val Ala Cys Tyr Val Cys Lys Ile Leu Asp Gln Met Pro>
1155     1160     1165     1170     1175     1180     1185 1190     1195 1200
  *               *               *               *               *
GCT ACT CCC AGC TCT CCC ATG TAT GTC GAT TGATAT CGYTGCTACA
CGA TGA GGG TCG AGA GGG TAC ATA CAG CTA ACTATA GCRACGATGT
Ala Thr Pro Ser Ser Pro Met Tyr Val Asp> (SEQ ID NO:8)

1205 1210  1215 1220  1225 1230  1235 1240  1245 1250  1255 1260
       *         *         *         *         *         *
TCAGACTCTA GAAAAAAGGG CTGAGAGGAA GCAAGACGTA AAGAATTTTC ATCCCGTATC
AGTCTGAGAT CTTTTTTCCC GACTCTCCTT CGTTCTGCAT TTCTTAAAAG TAGGGCATAG 1265 1270  1275 1280  1285 1290  1295 1300  1305 1310  1315 1320
       *         *         *         *         *         *
ACAGTGTTTT TATTGCTCGC CCAGACACCA TGTGCAATAA GATTGGTGTT CGTTTCCATC
TGTCACAAAA ATAACGAGCG GGTCTGTGGT ACACGTTATT CTAACCACAA GCAAAGGTAG 1325 1330  1335 1340  1345 1350  1355 1360  1365 1370  1375 1380
       *         *         *         *         *         *
ATGTCTGTAT ACTCCTGTCA CCTAGAACGT GCATCCTTGT AATACCTGAT TGATCACACA
TACAGACATA TGAGGACAGT GGATCTTGCA CGTAGGAACA TTATGGACTA ACTAGTGTGT 1385 1390  1395 1400  1405 1410  1415 1420  1425 1430  1435 1440
       *         *         *         *         *         *
GTGTTAGTGC TGGTCAGAGA GACCTCATCC TGCTCTTTTG TGATGAACAT ATTCATGAAA
CACAATCACG ACCAGTCTCT CTGGAGTAGG ACGAGAAAAC ACTACTTGTA TAAGTACTTT 1445 1450  1455 1460  1465 1470  1475 1480  1485 1490  1495 1500
       *         *         *         *         *         *
TGTGGAAGTC AGTACGATCA AGTTGTTGAC TGTGATTAGA TCACATCTTA AATTCATTTC
ACACCTTCAG TCATGCTAGT TCAACAACTG ACACTAATCT AGTGTAGAAT TTAAGTAAAG 1505 1510  1515 1520  1525 1530  1535 1540  1545 1550  1555 1560
       *         *         *         *         *         *
TAGACTCAAA ACCTGGAGAT GCAGCTACTG GAATGGTGTT TTGTCAGACT TCCAAATCCT
ATCTGAGTTT TGGACCTCTA CGTCGATGAC CTTACCACAA AACAGTCTGA AGGTTTAGGA 1565 1570  1575 1580  1585 1590  1595 1600  1605 1610  1615 1620
       *         *         *         *         *         *
GGAAGGACAC AGTGATGAAT GTACTATATC TGAACATAGA AACTCGGGCT TGAGTGAGAA
CCTTCCTGTG TCACTACTTA CATGATATAG ACTTGTATCT TTGAGCCCGA ACTCACTCTT
```

FIG. 7C

```
         1625 1630    1635 1640    1645 1650    1655 1660    1665 1670    1675 1680
                  *            *            *            *            *            *
         GAGCTTGCAC   AGCCAACGAG   ACACATTGCC   TTCTGGAGCT   GGGAGACAAA   GGAGGAATTT
         CTCGAACGTG   TCGGTTGCTC   TGTGTAACGG   AAGACCTCGA   CCCTCTGTTT   CCTCCTTAAA 1685 1690    1695 1700    1705 1710    1715 1720    1725 1730    1735 1740
                  *            *            *            *            *            *
         ACTTTCTTCA   CCAAGTGCAA   TAGATTACTG   ATGTGATATT   CTGTTGCTTT   ACAGTTACAG
         TGAAAGAAGT   GGTTCACGTT   ATCTAATGAC   TACACTATAA   GACAACGAAA   TGTCAATGTC 1745 1750    1755 1760    1765 1770    1775 1780    1785 1790    1795 1800
                  *            *            *            *            *            *
         TTGATGTTTG   GGGATCGATG   TGCTCAGCCA   AATTTCCTGT   TTGAAATATC   ATGTTAAATT
         AACTACAAAC   CCCTAGCTAC   ACGAGTCGGT   TTAAAGGACA   AACTTTATAG   TACAATTTAA 1805 1810    1815 1820    1825 1830    1835 1840    1845 1850    1855 1860
                  *            *            *            *            *            *
         AGAATGAATT   TATCTTTACC   AAAAACCATG   TTGCGTTCAA   AGAGGTGAAC   ATTAAAATAT
         TCTTACTTAA   ATAGAAATGG   TTTTTGGTAC   AACGCAAGTT   TCTCCACTTG   TAATTTTATA 1865 1870    1875 1880    1885 1890    1895 1900    1905 1910    1915 1920
                  *            *            *            *            *            *
         AGAGACAGGA   CAGAATGTGT   TCTTTTCTCC   TCTACCAGTC   CTATTTTTCA   ATGGGAAGAC
         TCTCTGTCCT   GTCTTACACA   AGAAAAGAGG   AGATGGTCAG   GATAAAAAGT   TACCCTTCTG 1925 1930    1935 1940    1945 1950    1955 1960    1965 1970    1975 1980
                  *            *            *            *            *            *
         TCAGGAGTCT   GCCACTTGTC   AAAGAAGGTG   CTGATCCTAA   GAATTTTTCA   TTCTCAGAAT
         AGTCCTCAGA   CGGTGAACAG   TTTCTTCCAC   GACTAGGATT   CTTAAAAAGT   AAGAGTCTTA 1985 1990    1995 2000    2005 2010    2015 2020    2025 2030    2035 2040
                  *            *            *            *            *            *
         TCGGTGTGCT   GCCAACTTGA   TGTTCCACCT   GCCACAAACC   ACCAGGACTG   AAAGAAGAAA
         AGCCACACGA   CGGTTGAACT   ACAAGGTGGA   CGGTGTTTGG   TGGTCCTGAC   TTTCTTCTTT 2045 2050    2055 2060    2065 2070    2075 2080    2085 2090    2095 2100
                  *            *            *            *            *            *
         ACAGTACAGA   AGGCAAAGTT   TACAGATGTT   TTTAATTCTA   GTATTTTATC   TGGAACAACT
         TGTCATGTCT   TCCGTTTCAA   ATGTCTACAA   AAATTAAGAT   CATAAAATAG   ACCTTGTTGA 2105 2110    2115 2120    2125 2130    2135 2140    2145 2150    2155 2160
                  *            *            *            *            *            *
         TGTAGCAGCT   ATATATTTCC   CCTTGGTCCC   AAGCCTGATA   CTTTAGCCAT   CATAACTCAC
         ACATCGTCGA   TATATAAAGG   GGAACCAGGG   TTCGGACTAT   GAAATCGGTA   GTATTGAGTG 2165 2170    2175 2180    2185 2190    2195 2200    2205 2210    2215 2220
                  *            *            *            *            *            *
         TAACAGGGAG   AAGTAGCTAG   TAGCAATGTG   CCTTGATTGA   TTAGATAAAG   ATTTCTAGTA
         ATTGTCCCTC   TTCATCGATC   ATCGTTACAC   GGAACTAACT   AATCTATTTC   TAAAGATCAT 2225 2230    2235 2240    2245 2250    2255 2260    2265 2270    2275 2280
                  *            *            *            *            *            *
         GGCAGCAAAA   GACCAAATCT   CAGTTGTTTG   CTTCTTGCCA   TCACTGGTCC   AGGTCTTCAG
         CCGTCGTTTT   CTGGTTTAGA   GTCAACAAAC   GAAGAACGGT   AGTGACCAGG   TCCAGAAGTC 2285 2290    2295 2300    2305 2310    2315 2320    2325 2330    2335 2340
                  *            *            *            *            *            *
         TTTCCGAATC   TCTTTCCCTT   CCCCTGTGGT   CTATTGTCGC   TATGTGACTT   GCGCTTAATC
         AAAGGCTTAG   AGAAAGGGAA   GGGGACACCA   GATAACAGCG   ATACACTGAA   CGCGAATTAG 2345 2350    2355 2360    2365 2370    2375 2380    2385 2390    2395 2400
```

FIG. 7D

```
            *          *          *          *          *          *
CAATATTTTG CCTTTTTTCT ATATCAAAAA ACCTTTACAG TTAGCAGGGA TGTTCCTTAC
GTTATAAAAC GGAAAAAAGA TATAGTTTTT TGGAAATGTC AATCGTCCCT ACAAGGAATG
   2405 2410   2415 2420   2425 2430   2435 2440   2445 2450   2455 2460
            *          *          *          *          *          *
CGAGGATTTT TAACCCCCAA TCTCTCATAA TCGCTAGTGT TTAAAAGGCT AAGAATAGTG
GCTCCTAAAA ATTGGGGGTT AGAGAGTATT AGCGATCACA AATTTTCCGA TTCTTATCAC
   2465 2470   2475 2480   2485 2490   2495 2500   2505 2510   2515 2520
            *          *          *          *          *          *
GGGCCCAACC GATGTGGTAG GTGATAAAGA GGCATCTTTT CTAGAGACAC ATTGGACCAG
CCCGGGTTGG CTACACCATC CACTATTTCT CCGTAGAAAA GATCTCTGTG TAACCTGGTC
   2525 2530   2535 2540   2545 2550   2555 2560   2565 2570   2575 2580
            *          *          *          *          *          *
ATGAGGATCC GAAACGGCAG CCTTTACGTT CATCACCTGC TAGAACCTCT CGTAGTCCAT
TACTCCTAGG CTTTGCCGTC GGAAATGCAA GTAGTGGACG ATCTTGGAGA GCATCAGGTA
   2585 2590   2595 2600   2605 2610   2615 2620   2625 2630   2635 2640
            *          *          *          *          *          *
CACCATTTCT TGGCATTGGA ATTCTACTGG AAAAAAATAC AAAAAGCAAA ACAAAACCCT
GTGGTAAAGA ACCGTAACCT TAAGATGACC TTTTTTTATG TTTTTCGTTT TGTTTTGGGA
   2645 2650   2655 2660   2665 2670   2675 2680   2685 2690   2695 2700
            *          *          *          *          *          *
CAGCACTGTT ACAAGAGGCC ATTTAAGTAT CTTGTGCTTC TTCACTTACC CATTAGCCAG
GTCGTGACAA TGTTCTCCGG TAAATTCATA GAACACGAAG AAGTGAATGG GTAATCGGTC
   2705 2710   2715 2720   2725 2730   2735 2740   2745 2750   2755 2760
            *          *          *          *          *          *
GTTCTCATTA GGTTTTGCTT GGGCCTCCCT GGCACTGAAC CTTAGGCTTT GTATGACAGT
CAAGAGTAAT CCAAAACGAA CCCGGAGGGA CCGTGACTTG GAATCCGAAA CATACTGTCA
   2765 2770   2775 2780   2785 2790   2795 2800   2805 2810   2815 2820
            *          *          *          *          *          *
GAAGCAGCAC TGTGAGTGGT TCAAGCACAC TGGAATATAA AACAGTCATG GCCTGAGATG
CTTCGTCGTG ACACTCACCA AGTTCGTGTG ACCTTATATT TTGTCAGTAC CGGACTCTAC
   2825 2830   2835 2840   2845 2850   2855 2860   2865 2870   2875 2880
            *          *          *          *          *          *
CAGGTGATGC CATTACAGAA CCAAATCGTG GCACGTATTG CTGTGTCTCC TCTCAGAGTG
GTCCACTACG GTAATGTCTT GGTTTAGCAC CGTGCATAAC GACACAGAGG AGAGTCTCAC
   2885 2890   2895 2900   2905 2910   2915 2920   2925 2930   2935 2940
            *          *          *          *          *          *
ACAGTCATAA ATACTGTCAA ACAATAAAGG GAGAATGGTG CTGTTTAAAG TCACATCCCT
TGTCAGTATT TATGACAGTT TGTTATTTCC CTCTTACCAC GACAAATTTC AGTGTAGGGA
   2945 2950   2955 2960   2965 2970   2975 2980   2985 2990   2995 3000
            *          *          *          *          *          *
GTAAATTGCA GAATTCAAAA GTGATTATCT CTTTGATCTA CTTGCCTCAT TTCCCTATCT
CATTTAACGT CTTAAGTTTT CACTAATAGA GAAACTAGAT GAACGGAGTA AAGGGATAGA
   3005 3010   3015 3020   3025 3030   3035 3040   3045 3050   3055 3060
            *          *          *          *          *          *
TCTCCCCCAC GGTATCCTAA ACTTTAGACT TCCCACTGTT CTGAAAGGAG ACATTGCTCT
AGAGGGGGTG CCATAGGATT TGAAATCTGA AGGGTGACAA GACTTTCCTC TGTAACGAGA
   3065 3070   3075 3080   3085 3090   3095 3100   3105 3110   3115 3120
            *          *          *          *          *          *
ATGTCTGCCT TCGACCACAG CAAGCCATCA TCCTCCATTG CTCCCGGGGA CTCAAGAGGA
```

FIG. 7E

```
                TACAGACGGA AGCTGGTGTC GTTCGGTAGT AGGAGGTAAC GAGGGCCCCT GAGTTCTCCT 3125 3130  3135 3140  3145 3150  3155 3160  3165 3170  3175 3180
                   *          *          *          *          *          *
                ATCTGTTTCT CTGCTGTCAA CTTCCCATCT GGCTCAGCAT AGGGTCACTT TGCCATTATG
                TAGACAAAGA GACGACAGTT GAAGGGTAGA CCGAGTCGTA TCCCAGTGAA ACGGTAATAC 3185 3190  3195 3200  3205 3210  3215 3220  3225 3230  3235 3240
                   *          *          *          *          *          *
                CAAATGGAGA TAAAAGCAAT TCTGGCTGTC CAGGAGCTAA TCTGACCGTT CTATTGTGTG
                GTTTACCTCT ATTTTCGTTA AGACCGACAG GTCCTCGATT AGACTGGCAA GATAACACAC 3245 3250  3255 3260  3265 3270  3275 3280  3285 3290  3295 3300
                   *          *          *          *          *          *
                GATGACCACA TAAGAAGGCA ATTTTAGTGT ATTAATCATA GATTATTATA AACTATAAAC
                CTACTGGTGT ATTCTTCCGT TAAAATCACA TAATTAGTAT CTAATAATAT TTGATATTTG 3305 3310  3315 3320  3325 3330  3335 3340  3345 3350  3355 3360
                   *          *          *          *          *          *
                TTAAGGGCAA GGAGTTTATT ACAATGTATC TTTATTAAAA CAAAAGGGTG TATAGTGTTC
                AATTCCCGTT CCTCAAATAA TGTTACATAG AAATAATTTT GTTTTCCCAC ATATCACAAG 3365 3370  3375 3380  3385 3390  3395 3400  3405 3410  3415 3420
                   *          *          *          *          *          *
                ACAAACTGTG AAAATAGTGT AAGAACTGTA CATTGTGAGC TCTGGTTATT TTTCTCTTGT
                TGTTTGACAC TTTTATCACA TTCTTGACAT GTAACACTCG AGACCAATAA AAAGAGAACA 3425 3430  3435 3440  3445 3450  3455 3460  3465 3470  3475 3480
                   *          *          *          *          *          *
                ACCATAGAAA AATGTATAAA AATTATCAAA AAGCTAATGT GCAGGGATAT TGCCTTATTT
                TGGTATCTTT TTACATATTT TTAATAGTTT TTCGATTACA CGTCCCTATA ACGGAATAAA 3485 3490  3495 3500  3505 3510  3515 3520  3525 3530  3535 3540
                   *          *          *          *          *          *
                GTCTGTAAAA AATGGAGCTC AGTAACATAA CTGCTTCTTG GAGCTTTGGA ATATTTTATC
                CAGACATTTT TTACCTCGAG TCATTGTATT GACGAAGAAC CTCGAAACCT TATAAAATAG 3545 3550
                   *
                CTGTATTCTT GTTT   (SEQ ID NO:7)
                GACATAAGAA CAAA
```

FIG. 7F

```
              5        10       15       20       25       30       35       40       45       50
                                          *                          *                          *
        CTCCCAACA ATG GCG GCT CCG AGC CCG AGC GGC GGC GGC GGC TCC GGG GGC
        GAGGGTTGT TAC CGC CGA GGC TCG GGC TCG CCG CCG CCG CCG AGG CCC CCG
                  Met Ala Ala Pro Ser Pro Ser Gly Gly Gly Gly Ser Gly Gly>

55       60       65       70       75       80       85       90       95
          *                          *                          *                 *
        GGC AGC GGC AGC GGC ACC CCC GGC CCC GTA GGG TCC CCG GCG CCA GGC
        CCG TCG CCG TCG CCG TGG GGG CCG GGG CAT CCC AGG GGC CGC GGT CCG
        Gly Ser Gly Ser Gly Thr Pro Gly Pro Val Gly Ser Pro Ala Pro Gly>

100      105      110      115      120      125      130      135      140      145
          *                          *                          *                          *
        CAC CCG GCC GTC AGC AGC ATG CAG GGT AAA CGC AAA GCA CTG AAG TTG
        GTG GGC CGG CAG TCG TCG TAC GTC CCA TTT GCG TTT CGT GAC TTC AAC
        His Pro Ala Val Ser Ser Met Gln Gly Lys Arg Lys Ala Leu Lys Leu>

150      155      160      165      170      175      180      185      190      195
          *                          *                          *                          *
        AAT TTT GCA AAT CCA CCT TTC AAA TCT ACA GCA AGG TTT ACT CTG AAT
        TTA AAA CGT TTA GGT GGA AAG TTT AGA TGT CGT TCC AAA TGA GAC TTA
        Asn Phe Ala Asn Pro Pro Phe Lys Ser Thr Ala Arg Phe Thr Leu Asn>

200      205      210      215      220      225      230      235      240
                   *                          *                          *                 *
        CCC AAT CCT ACA GGA GTT CAA AAC CCA CAC ATA GAG AGA CTG AGA ACA
        GGG TTA GGA TGT CCT CAA GTT TTG GGT GTG TAT CTC TCT GAC TCT TGT
        Pro Asn Pro Thr Gly Val Gln Asn Pro His Ile Glu Arg Leu Arg Thr>

245      250      255      260      265      270      275      280      285      290
          *                          *                          *                          *
        CAC AGC ATT GAG TCA TCA GGA AAA CTG AAG ATC TCC CCT GAA CAA CAC
        GTG TCG TAA CTC AGT AGT CCT TTT GAC TTC TAG AGG GGA CTT GTT GTG
        His Ser Ile Glu Ser Ser Gly Lys Leu Lys Ile Ser Pro Glu Gln His>

295      300      305      310      315      320      325      330      335
                   *                          *                          *                 *
        TGG GAT TTC ACT GCA GAG GAC TTG AAA GAC CTT GGA GAA ATT GGA CGA
        ACC CTA AAG TGA CGT CTC CTG AAC TTT CTG GAA CCT CTT TAA CCT GCT
        Trp Asp Phe Thr Ala Glu Asp Leu Lys Asp Leu Gly Glu Ile Gly Arg>

340      345      350      355      360      365      370      375      380      385
          *                          *                          *                          *
        GGA GCT TAT GGT TCT GTC AAC AAA ATG GTC CAC AAA CCA AGT GGG CAA
        CCT CGA ATA CCA AGA CAG TTG TTT TAC CAG GTG TTT GGT TCA CCC GTT
        Gly Ala Tyr Gly Ser Val Asn Lys Met Val His Lys Pro Ser Gly Gln>

390      395      400      405      410      415      420      425      430      435
          *                          *                          *                          *
        ATA ATG GCA GTT AAA AGA ATT CGG TCA ACA GTG GAT GAA AAA GAA CAA
        TAT TAC CGT CAA TTT TCT TAA GCC AGT TGT CAC CTA CTT TTT CTT GTT
        Ile Met Ala Val Lys Arg Ile Arg Ser Thr Val Asp Glu Lys Glu Gln>

440      445      450      455      460      465      470      475      480
                   *                          *                          *                 *
        AAA CAA CTT CTT ATG GAT TTG GAT GTA GTA ATG CGG AGT AGT GAT TGC
        TTT GTT GAA GAA TAC CTA AAC CTA CAT CAT TAC GCC TCA TCA CTA ACG
        Lys Gln Leu Leu Met Asp Leu Asp Val Val Met Arg Ser Ser Asp Cys>
```

FIG. 8A

```
        485       490       495       500       505       510       515       520       525       530
                   *                   *                   *                   *                   *
         CCA TAC ATT GTT CAG TTT TAT GGT GCA CTC TTC AGA GAG GGT GAC TGT
         GGT ATG TAA CAA GTC AAA ATA CCA CGT GAG AAG TCT CTC CCA CTG ACA
         Pro Tyr Ile Val Gln Phe Tyr Gly Ala Leu Phe Arg Glu Gly Asp Cys>

535       540       545       550       555       560       565       570       575
                       *                   *                   *                   *
             TGG ATC TGT ATG GAA CTC ATG TCT ACC TCG TTT GAT AAG TTT TAC AAA
             ACC TAG ACA TAC CTT GAG TAC AGA TGG AGC AAA CTA TTC AAA ATG TTT
             Trp Ile Cys Met Glu Leu Met Ser Thr Ser Phe Asp Lys Phe Tyr Lys>

580       585       590       595       600       605       610       615       620       625
         *                   *                   *                   *                   *
         TAT GTA TAT AGT GTA TTA GAT GAT GTT ATT CCA GAA GAA ATT TTA GGC
         ATA CAT ATA TCA CAT AAT CTA CTA CAA TAA GGT CTT CTT TAA AAT CCG
         Tyr Val Tyr Ser Val Leu Asp Asp Val Ile Pro Glu Glu Ile Leu Gly>

630       635       640       645       650       655       660       665       670       675
             *                   *                   *                   *                   *
             AAA ATC ACT TTA GCA ACT GTG AAA GCA CTA AAC CAC TTA AAA GAA AAC
             TTT TAG TGA AAT CGT TGA CAC TTT CGT GAT TTG GTG AAT TTT CTT TTG
             Lys Ile Thr Leu Ala Thr Val Lys Ala Leu Asn His Leu Lys Glu Asn>

680       685       690       695       700       705       710       715       720
                   *                   *                   *                   *                   *
                 TTG AAA ATT ATT CAC AGA GAT ATC AAA CCT TCC AAT ATT CTT CTG GAC
                 AAC TTT TAA TAA GTG TCT CTA TAG TTT GGA AGG TTA TAA GAA GAC CTG
                 Leu Lys Ile Ile His Arg Asp Ile Lys Pro Ser Asn Ile Leu Leu Asp>

725       730       735       740       745       750       755       760       765       770
           *                   *                   *                   *                   *
         AGA AGT GGA AAT ATT AAG CTC TGT GAC TTC GGC ATC AGT GGA CAG CTT
         TCT TCA CCT TTA TAA TTC GAG ACA CTG AAG CCG TAG TCA CCT GTC GAA
         Arg Ser Gly Asn Ile Lys Leu Cys Asp Phe Gly Ile Ser Gly Gln Leu>

775       780       785       790       795       800       805       810       815
                       *                   *                   *                   *
             GTG GAC TCT ATT GCC AAG ACA AGA GAT GCT GGC TGT AGG CCA TAC ATG
             CAC CTG AGA TAA CGG TTC TGT TCT CTA CGA CCG ACA TCC GGT ATG TAC
             Val Asp Ser Ile Ala Lys Thr Arg Asp Ala Gly Cys Arg Pro Tyr Met>

820       825       830       835       840       845       850       855       860       865
                   *                   *                   *                   *
         GCA CCT GAA AGA ATA GAC CCA AGC GCA TCA CGA CAA GGA TAT GAT GTC
         CGT GGA CTT TCT TAT CTG GGT TCG CGT AGT GCT GTT CCT ATA CTA CAG
         Ala Pro Glu Arg Ile Asp Pro Ser Ala Ser Arg Gln Gly Tyr Asp Val>

870       875       880       885       890       895       900       905       910       915
                       *                   *                   *                   *
             CGC TCT GAT GTC TGG AGT TTG GGG ATC ACA TTG TAT GAG TTG GCC ACA
             GCG AGA CTA CAG ACC TCA AAC CCC TAG TGT AAC ATA CTC AAC CGG TGT
             Arg Ser Asp Val Trp Ser Leu Gly Ile Thr Leu Tyr Glu Leu Ala Thr>

920       925       930       935       940       945       950       955       960
                       *                   *                   *                   *
                 GGC CGA TTT CCT TAT CCA AAG TGG AAT AGT GTA TTT GAT CAA CTA ACA
                 CCG GCT AAA GGA ATA GGT TTC ACC TTA TCA CAT AAA CTA GTT GAT TGT
                 Gly Arg Phe Pro Tyr Pro Lys Trp Asn Ser Val Phe Asp Gln Leu Thr>

```
     CAA GTC GTG AAA GGA GAT CCT CCG CAG CTG AGT AAT TCT GAG GAA AGG
     GTT CAG CAC TTT CCT CTA GGA GGC GTC GAC TCA TTA AGA CTC CTT TCC
     Gln Val Val Lys Gly Asp Pro Pro Gln Leu Ser Asn Ser Glu Glu Arg>

1015  1020   1025  1030  1035   1040  1045   1050   1055
                       *           *            *            *
     GAA TTC TCC CCG AGT TTC ATC AAC TTT GTC AAC TTG TGC CTT ACG AAG
     CTT AAG AGG GGC TCA AAG TAG TTG AAA CAG TTG AAC ACG GAA TGC TTC
     Glu Phe Ser Pro Ser Phe Ile Asn Phe Val Asn Leu Cys Leu Thr Lys>

1060  1065   1070   1075  1080   1085  1090  1095   1100    1105
       *             *             *           *              *
     GAT GAA TCC AAA AGG CCA AAG TAT AAA GAG CTT CTG AAA CAT CCC TTT
     CTA CTT AGG TTT TCC GGT TTC ATA TTT CTC GAA GAC TTT GTA GGG AAA
     Asp Glu Ser Lys Arg Pro Lys Tyr Lys Glu Leu Leu Lys His Pro Phe>

1110    1115    1120   1125   1130    1135   1140    1145   1150    1155
    *               *              *             *              *
     ATT TTG ATG TAT GAA GAA CGT GCC GTT GAG GTC GCA TGC TAT GTT TGT
     TAA AAC TAC ATA CTT CTT GCA CGG CAA CTC CAG CGT ACG ATA CAA ACA
     Ile Leu Met Tyr Glu Glu Arg Ala Val Glu Val Ala Cys Tyr Val Cys>

1160   1165   1170    1175   1180   1185    1190   1195    1200
                        *              *              *              *
     AAA ATC CTG GAT CAA ATG CCA GCT ACT CCC AGC TCT CCC ATG TAT GTC
     TTT TAG GAC CTA GTT TAC GGT CGA TGA GGG TCG AGA GGG TAC ATA CAG
     Lys Ile Leu Asp Gln Met Pro Ala Thr Pro Ser Ser Pro Met Tyr Val>

1205   1210   1215  1220    1225  1230    1235  1240    1245  1250    1255 1260
    *             *              *            *              *              *
    GAT TGAT ATCGCTGCTA CATCAGACTC TAGAAAAAAG GCTGAGAGG AAGCAAGACG
    CTA ACTA TAGCGACGAT GTAGTCTGAG ATCTTTTTTC CCGACTCTCC TTCGTTCTGC
    Asp>        (SEQ ID NO:10)

1265  1270    1275  1280    1285  1290    1295  1300    1305  1310    1315  1320
                 *              *             *              *             *              *
     TAAAGAATTT TCATCCCGTA TCACAGTGTT TTTATTGCTC GCCCAGACAC CATGTGCAAT
     ATTTCTTAAA AGTAGGGCAT AGTGTCACAA AAATAACGAG CGGGTCTGTG GTACACGTTA 1325  1330    1335  1340    1345  1350    1355  1360    1365  1370    1375  1380
                 *              *             *              *             *              *
     AAGATTGGTG TTCGTTTCCA TCATGTCTGT ATACTCCTGT CACCTAGAAC GTGCATCCTT
     TTCTAACCAC AAGCAAAGGT AGTACAGACA TATGAGGACA GTGGATCTTG CACGTAGGAA 1385 1390    1395  1400    1405  1410    1415  1420    1425  1430    1435  1440
                 *              *             *              *             *              *
     GTAATACCTG ATTGATCACA CAGTGTTAGT GCTGGTCAGA GAGACCTCAT CCTGCTCTTT
     CATTATGGAC TAACTAGTGT GTCACAATCA CGACCAGTCT CTCTGGAGTA GGACGAGAAA 1445 1450    1455  1460    1465  1470    1475  1480    1485  1490    1495  1500
                 *              *             *              *             *              *
     TGTGATGAAC ATATTCATGA AATGTGGAAG TCAGTACGAT CAAGTTGTTG ACTGTGATTA
     ACACTACTTG TATAAGTACT TTACACCTTC AGTCATGCTA GTTCAACAAC TGACACTAAT 1505 1510    1515  1520    1525  1530    1535  1540    1545  1550    1555  1560
                 *              *             *              *             *              *
     GATCACATCT TAAATTCATT TCTAGACTCA AAACCTGGAG ATGCAGCTAC TGGAATGGTG
     CTAGTGTAGA ATTTAAGTAA AGATCTGAGT TTTGGACCTC TACGTCGATG ACCTTACCAC 1565 1570    1575  1580    1585  1590    1595  1600    1605  1610    1615  1620
                 *              *             *              *             *              *
     TTTTGTCAGA CTTCCAAATC CTGGAAGGAC ACAGTGATGA ATGTACTATA TCTGAACATA
```

FIG. 8C

```
AAAACAGTCT GAAGGTTTAG GACCTTCCTG TGTCACTACT TACATGATAT AGACTTGTAT
1625 1630  1635 1640  1645 1650  1655 1660  1665 1670  1675 1680
         *          *          *          *          *          *
GAAACTCGGG CTTGAGTGAG AAGAGCTTGC ACAGCCAACG AGACACATTG CCTTCTGGAG
CTTTGAGCCC GAACTCACTC TTCTCGAACG TGTCGGTTGC TCTGTGTAAC GGAAGACCTC
1685 1690  1695 1700  1705 1710  1715 1720  1725 1730  1735 1740
         *          *          *          *          *          *
CTGGGAGACA AAGGAGGAAT TTACTTTCTT CACCAAGTGC AATAGATTAC TGATGTGATA
GACCCTCTGT TTCCTCCTTA AATGAAAGAA GTGGTTCACG TTATCTAATG ACTACACTAT
1745 1750  1755 1760  1765 1770  1775 1780  1785 1790  1795 1800
         *          *          *          *          *          *
TTCTGTTGCT TTACAGTTAC AGTTGATGTT TGGGGATCGA TGTGCTCAGC CAAATTTCCT
AAGACAACGA AATGTCAATG TCAACTACAA ACCCCTAGCT ACACGAGTCG GTTTAAAGGA
1805 1810  1815 1820  1825 1830  1835 1840  1845 1850  1855 1860
         *          *          *          *          *          *
GTTTGAAATA TCATGTTAAA TTAGAATGAA TTTATCTTTA CCAAAAACCA TGTTGCGTTC
CAAACTTTAT AGTACAATTT AATCTTACTT AAATAGAAAT GGTTTTTGGT ACAACGCAAG
1865 1870  1875 1880  1885 1890  1895 1900  1905 1910  1915 1920
         *          *          *          *          *          *
AAAGAGGTGA ACATTAAAAT ATAGAGACAG GACAGAATGT GTTCTTTTCT CCTCTACCAG
TTTCTCCACT TGTAATTTTA TATCTCTGTC CTGTCTTACA CAAGAAAAGA GGAGATGGTC
1925 1930  1935 1940  1945 1950  1955 1960  1965 1970  1975 1980
         *          *          *          *          *          *
TCCTATTTTT CAATGGGAAG ACTCAGGAGT CTGCCACTTG TCAAAGAAGG TGCTGATCCT
AGGATAAAAA GTTACCCTTC TGAGTCCTCA GACGGTGAAC AGTTTCTTCC ACGACTAGGA
1985 1990  1995 2000  2005 2010  2015 2020  2025 2030  2035 2040
         *          *          *          *          *          *
AAGAATTTTT CATTCTCAGA ATTCGGTGTG CTGCCAACTT GATGTTCCAC CTGCCACAAA
TTCTTAAAAA GTAAGAGTCT TAAGCCACAC GACGGTTGAA CTACAAGGTG GACGGTGTTT
2045 2050  2055 2060  2065 2070  2075 2080  2085 2090  2095 2100
         *          *          *          *          *          *
CCACCAGGAC TGAAAGAAGA AAACAGTACA GAAGGCAAAG TTTACAGATG TTTTTAATTC
GGTGGTCCTG ACTTTCTTCT TTTGTCATGT CTTCCGTTTC AAATGTCTAC AAAAATTAAG
2105 2110  2115 2120  2125 2130  2135 2140  2145 2150  2155 2160
         *          *          *          *          *          *
TAGTATTTTA TCTGGAACAA CTTGTAGCAG CTATATATTT CCCCTTGGTC CCAAGCCTGA
ATCATAAAAT AGACCTTGTT GAACATCGTC GATATATAAA GGGGAACCAG GGTTCGGACT
2165 2170  2175 2180  2185 2190  2195 2200  2205 2210  2215 2220
         *          *          *          *          *          *
TACTTTAGCC ATCATAACTC ACTAACAGGG AGAAGTAGCT AGTAGCAATG TGCCTTGATT
ATGAAATCGG TAGTATTGAG TGATTGTCCC TCTTCATCGA TCATCGTTAC ACGGAACTAA
2225 2230  2235 2240  2245 2250  2255 2260  2265 2270  2275 2280
         *          *          *          *          *          *
GATTAGATAA AGATTTCTAG TAGGCAGCAA AAGACCAAAT CTCAGTTGTT TGCTTCTTGC
CTAATCTATT TCTAAAGATC ATCCGTCGTT TTCTGGTTTA GAGTCAACAA ACGAAGAACG
2285 2290  2295 2300  2305 2310  2315 2320  2325 2330  2335 2340
         *          *          *          *          *          *
CATCACTGGT CCAGGTCTTC AGTTTCCGAA TCTCTTTCCC TTCCCCTGTG GTCTATTGTC
GTAGTGACCA GGTCCAGAAG TCAAAGGCTT AGAGAAAGGG AAGGGGACAC CAGATAACAG
```

FIG. 8D

```
          2345 2350  2355 2360  2365 2370  2375 2380  2385 2390  2395 2400
               *         *          *          *          *          *
          GCTATGTGAC TTGCGCTTAA TCCAATATTT TGCCTTTTTT CTATATCAAA AAACCTTTAC
          CGATACACTG AACGCGAATT AGGTTATAAA ACGGAAAAAA GATATAGTTT TTTGGAAATG 2405 2410  2415 2420  2425 2430  2435 2440  2445 2450  2455 2460
               *         *          *          *          *          *
          AGTTAGCAGG GATGTTCCTT ACCGAGGATT TTTAACCCCC AATCTCTCAT AATCGCTAGT
          TCAATCGTCC CTACAAGGAA TGGCTCCTAA AAATTGGGGG TTAGAGAGTA TTAGCGATCA 2465 2470  2475 2480  2485 2490  2495 2500  2505 2510  2515 2520
               *         *          *          *          *          *
          GTTTAAAAGG CTAAGAATAG TGGGGCCCAA CCGATGTGGT AGGTGATAAA GAGGCATCTT
          CAAATTTTCC GATTCTTATC ACCCCGGGTT GGCTACACCA TCCACTATTT CTCCGTAGAA 2525 2530  2535 2540  2545 2550  2555 2560  2565 2570  2575 2580
               *         *          *          *          *          *
          TTCTAGAGAC ACATTGGACC AGATGAGGAT CCGAAACGGC AGCCTTTACG TTCATCACCT
          AAGATCTCTG TGTAACCTGG TCTACTCCTA GGCTTTGCCG TCGGAAATGC AAGTAGTGGA 2585 2590  2595 2600  2605 2610  2615 2620  2625 2630  2635 2640
               *         *          *          *          *          *
          GCTAGAACCT CTCGTAGTCC ATCACCATTT CTTGGCATTG GAATTCTACT GGAAAAAAAT
          CGATCTTGGA GAGCATCAGG TAGTGGTAAA GAACCGTAAC CTTAAGATGA CCTTTTTTTA 2645 2650  2655 2660  2665 2670  2675 2680  2685 2690  2695 2700
               *         *          *          *          *          *
          ACAAAAAGCA AAACAAAACC CTCAGCACTG TTACAAGAGG CCATTTAAGT ATCTTGTGCT
          TGTTTTTCGT TTTGTTTTGG GAGTCGTGAC AATGTTCTCC GGTAAATTCA TAGAACACGA 2705 2710  2715 2720  2725 2730  2735 2740  2745 2750  2755 2760
               *         *          *          *          *          *
          TCTTCACTTA CCCATTAGCC AGGTTCTCAT TAGGTTTTGC TTGGGCCTCC CTGGCACTGA
          AGAAGTGAAT GGGTAATCGG TCCAAGAGTA ATCCAAAACG AACCCGGAGG GACCGTGACT 2765 2770  2775 2780  2785 2790  2795 2800  2805 2810  2815 2820
               *         *          *          *          *          *
          ACCTTAGGCT TTGTATGACA GTGAAGCAGC ACTGTGAGTG GTTCAAGCAC ACTGGAATAT
          TGGAATCCGA AACATACTGT CACTTCGTCG TGACACTCAC CAAGTTCGTG TGACCTTATA 2825 2830  2835 2840  2845 2850  2855 2860  2865 2870  2875 2880
               *         *          *          *          *          *
          AAAACAGTCA TGGCCTGAGA TGCAGGTGAT GCCATTACAG AACCAAATCG TGGCACGTAT
          TTTTGTCAGT ACCGGACTCT ACGTCCACTA CGGTAATGTC TTGGTTTAGC ACCGTGCATA 2885 2890  2895 2900  2905 2910  2915 2920  2925 2930  2935 2940
               *         *          *          *          *          *
          TGCTGTGTCT CCTCTCAGAG TGACAGTCAT AAATACTGTC AAACAATAAA GGGAGAATGG
          ACGACACAGA GGAGAGTCTC ACTGTCAGTA TTTATGACAG TTTGTTATTT CCCTCTTACC 2945 2950  2955 2960  2965 2970  2975 2980  2985 2990  2995 3000
               *         *          *          *          *          *
          TGCTGTTTAA AGTCACATCC CTGTAAATTG CAGAATTCAA AAGTGATTAT CTCTTTGATC
          ACGACAAATT TCAGTGTAGG GACATTTAAC GTCTTAAGTT TTCACTAATA GAGAAACTAG 3005 3010  3015 3020  3025 3030  3035 3040  3045 3050  3055 3060
               *         *          *          *          *          *
          TACTTGCCTC ATTTCCCTAT CTTCTCCCCC ACGGTATCCT AAACTTTAGA CTTCCCACTG
          ATGAACGGAG TAAAGGGATA GAAGAGGGGG TGCCATAGGA TTTGAAATCT GAAGGGTGAC 3065 3070  3075 3080  3085 3090  3095 3100  3105 3110  3115 3120
               *         *          *          *          *          *
```

FIG. 8E

```
TTCTGAAAGG AGACATTGCT CTATGTCTGC CTTCGACCAC AGCAAGCCAT CATCCTCCAT
AAGACTTTCC TCTGTAACGA GATACAGACG GAAGCTGGTG TCGTTCGGTA GTAGGAGGTA 3125 3130  3135 3140  3145 3150  3155 3160  3165 3170  3175 3180
         *          *          *          *          *          *
TGCTCCCGGG GACTCAAGAG GAATCTGTTT CTCTGCTGTC AACTTCCCAT CTGGCTCAGC
ACGAGGGCCC CTGAGTTCTC CTTAGACAAA GAGACGACAG TTGAAGGGTA GACCGAGTCG 3185 3190  3195 3200  3205 3210  3215 3220  3225 3230  3235 3240
         *          *          *          *          *          *
ATAGGGTCAC TTTGCCATTA TGCAAATGGA GATAAAAGCA ATTCTGGCTG TCCAGGAGCT
TATCCCAGTG AAACGGTAAT ACGTTTACCT CTATTTTCGT TAAGACCGAC AGGTCCTCGA 3245 3250  3255 3260  3265 3270  3275 3280  3285 3290  3295 3300
         *          *          *          *          *          *
AATCTGACCG TTCTATTGTG TGGATGACCA CATAAGAAGG CAATTTTAGT GTATTAATCA
TTAGACTGGC AAGATAACAC ACCTACTGGT GTATTCTTCC GTTAAAATCA CATAATTAGT 3305 3310  3315 3320  3325 3330  3335 3340  3345 3350  3355 3360
         *          *          *          *          *          *
TAGATTATTA TAAACTATAA ACTTAAGGGC AAGGAGTTTA TTACAATGTA TCTTTATTAA
ATCTAATAAT ATTTGATATT TGAATTCCCG TTCCTCAAAT AATGTTACAT AGAAATAATT 3365 3370  3375 3380  3385 3390  3395 3400  3405 3410  3415 3420
         *          *          *          *          *          *
AACAAAAGGG TGTATAGTGT TCACAAACTG TGAAAATAGT GTAAGAACTG TACATTGTGA
TTGTTTTCCC ACATATCACA AGTGTTTGAC ACTTTTATCA CATTCTTGAC ATGTAACACT 3425 3430  3435 3440  3445 3450  3455 3460  3465 3470  3475 3480
         *          *          *          *          *          *
GCTCTGGTTA TTTTTCTCTT GTACCATAGA AAAATGTATA AAAATTATCA AAAAGCTAAT
CGAGACCAAT AAAAAGAGAA CATGGTATCT TTTTACATAT TTTTAATAGT TTTTCGATTA 3485 3490  3495 3500  3505 3510  3515 3520  3525 3530  3535 3540
         *          *          *          *          *          *
GTGCAGGGAT ATTGCCTTAT TTGTCTGTAA AAAATGGAGC TCAGTAACAT AACTGCTTCT
CACGTCCCTA TAACGGAATA AACAGACATT TTTTACCTCG AGTCATTGTA TTGACGAAGA 3545 3550  3555 3560  3565 3570  3575
         *          *          *
TGGAGCTTTG GAATATTTTA TCCTGTATTC TTGTTT    (SEQ ID NO:9)
ACCTCGAAAC CTTATAAAAT AGGACATAAG AACAAA
```

FIG. 8F

CYTOKINE-STRESS- AND ONCOPROTEIN-ACTIVATED HUMAN PROTEIN KINASE KINASES

CROSS-REFERENCE TO RELATED APPLICATION

This application is a continuation of U.S. application Ser. No. 09/057,009, filed Apr. 7, 1998; which is a CIP of Ser. No. 08/530,950, filed Sep. 19, 1995 (issued) now U.S. Pat. No. 5,736,381, which is a CIP of U.S. Ser. No. 08/446,083, filed May 19, 1995 now U.S. Pat. No. 5,804,427 (issued), which application is incorporated herein by reference and to which application we claim priority under 35 USC §120.

STATEMENT AS TO FEDERALLY SPONSORED RESEARCH

This invention was made in part with National Cancer Institute research grant CA 58396. The Federal government has certain rights in the invention.

BACKGROUND OF THE INVENTION

This invention relates to protein kinases.

Mitogen-activated protein (MAP) kinases are important mediators of signal transduction from the cell surface to the nucleus. Multiple MAP kinases have been described in yeast including SMK1, HOG1, NPK1, FUS3, and KSS1. In mammals, the MAP kinases identified are extracellular signal-regulated MAP kinase (ERK), c-Jun amino-terminal kinase (JNK), and p38 kinase (Davis (1994) Trends Biochem. Sci. 19:470). These MAP kinase isoforms are activated by dual phosphorylation on threonine and tyrosine.

Activating Transcription Factor-2 (ATF2), ATFa, and cAMP Response Element Binding Protein (CRE-BPa) are related transcription factors that bind to similar sequences located in the promoters of many genes (Ziff (1990) Trends in Genet. 6:69). The binding of these transcription factors leads to increased transcriptional activity. ATF2 binds to several viral proteins, including the oncoprotein E1a (Liu and Green (1994) Nature 368:520), the hepatitis B virus X protein (Maguire et al. (1991) Science 252:842), and the human T cell leukemia virus 1 tax protein (Wagner and Green (1993) Science 262:395). ATF2 also interacts with the tumor suppressor gene product Rb (Kim et al. (1992) Nature 358:331), the high mobility group protein HMG(I)Y (Du et al. (1993) Cell 74:887), and the transcription factors nuclear NF-κB (Du et al. (1993) Cell 74:887) and c-Jun (Benbrook and Jones (1990) Oncogene 5:295).

SUMMARY OF THE INVENTION

We have identified and isolated a new group of human mitogen-activated protein kinase kinases (MKKs). The MKK isoforms described herein, MKK3 (including MKK6) and MKK4 (including MKK4-α, -β, and -γ) have serine, threonine, and tyrosine kinase activity, and specifically phosphorylate the human MAP kinase p38 at Thr-$^{180}$ and Tyr$^{182}$. The MKK4 isoforms also phosphorylate the human MAP kinases JNK (including JNK1 and JNK2) at Thr$^{183}$ and Tyr$^{185}$.

Accordingly, the invention features a substantially pure human MKK polypeptide having serine, threonine, and tyrosine kinase activity that specifically phosphorylates human p38 MAP kinase. MKK3 has the amino acid sequence of SEQ ID NO:2. The invention further includes MKK6 having the amino acid sequence of SEQ ID NO:4 and having serine, threonine, and tyrosine kinase activity that specifically phosphorylates human p38 MAP kinase.

The invention further features a substantially pure human MKK polypeptide having serine, threonine, and tyrosine kinase activity that specifically phosphorylates human p38 MAP kinase and JNK. MKK4 isoform MKK4-α has the amino acid sequence of SEQ ID NO:6. MKK4 isoform MKK4-β has the amino acid sequence of SEQ ID NO:8. MKK4 isoform MKK4-γ has the amino acid sequence of SEQ ID NO:10.

As used herein, the term "mitogen-activating protein kinase kinase" or "MKK" means a protein kinase which possesses the characteristic activity of phosphorylating and activating a human mitogen-activating protein kinase. Examples of MKKs include MKK3 and MKK6, which specifically phosphorylate and activate p38 MAP kinase at Thr$^{180}$ and Tyr$^{182}$, and MKK4 isoforms which specifically phosphorylate and activate p38 MAP kinase at Thr$^{180}$ and Tyr$^{182}$, and JNK at Thr$^{183}$ and Tyr$^{185}$.

The invention includes the specific p38 MKKs disclosed, as well as closely related MKKs which are identified and isolated by the use of probes or antibodies prepared from the polynucleotide and amino acid sequences disclosed for the MKKs of the invention. This can be done using standard techniques, e.g., by screening a genomic, cDNA, or combinatorial chemical library with a probe having all or a part of the nucleic acid sequences of the disclosed MKKs. The invention further includes synthetic polynucleotides having all or part of the amino acid sequence of the MKKs herein described.

The term "polypeptide" means any chain of amino acids, regardless of length or post-translational modification (e.g., glycosylation or phosphorylation), and includes natural proteins as well as synthetic or recombinant polypeptides and peptides.

The term "substantially pure," when referring to a polypeptide, means a polypeptide that is at least 60%, by weight, free from the proteins and naturally-occurring organic molecules with which it is naturally associated. A substantially pure human MKK polypeptide is at least 75%, more preferably at least 90%, and most preferably at least 99%, by weight, human MKK polypeptide. A substantially pure human MKK can be obtained, for example, by extraction from a natural source; by expression of a recombinant nucleic acid encoding a human MKK polypeptide, or by chemically synthesizing the protein. Purity can be measured by any appropriate method, e.g., column chromatography, polyacrylamide gel electrophoresis, or HPLC analysis.

In one aspect, the invention features isolated and purified polynucleotides which encode the MKKs of the invention. In one embodiment, the polynucleotide is the nucleotide sequence of SEQ ID NO:1. In other embodiments, the polynucleotide is the nucleotide sequence of SEQ ID NO:3, SEQ ID NO:5, SEQ ID NO:7, or SEQ ID NO:9, respectively.

As used herein, "polynucleotide" refers to a nucleic acid sequence of deoxyribonucleotides or ribonucleotides in the form of a separate fragment or a component of a larger construct. DNA encoding portions or all of the polypeptides of the invention can be assembled from cDNA fragments or from oligonucleotides that provide a synthetic gene which can be expressed in a recombinant transcriptional unit. Polynucleotide sequences of the invention include DNA, RNA, and cDNA sequences, and can be derived from natural sources or synthetic sequences synthesized by methods known to the art.

As used herein, an "isolated" polynucleotide is a polynucleotide that is not immediately contiguous (i.e., covalently linked) with either of the coding sequences with which it is immediately contiguous (i.e., one at the 5' end and one at the 3' end) in the naturally-occurring genome of the organism from which the polynucleotide is derived. The term therefore includes, for example, a recombinant polynucleotide which is incorporated into a vector, into an autonomously replicating plasmid or virus, or into the genomic DNA of a prokaryote or eukaryote, or which exists as a separate molecule independent of other sequences. It also includes a recombinant DNA which is part of a hybrid gene encoding additional polypeptide sequences.

The isolated and purified polynucleotide sequences of the invention also include polynucleotide sequences that hybridize under stringent conditions to the polynucleotide sequences specified herein. The term "stringent conditions" means hybridization conditions that guarantee specificity between hybridizing polynucleotide sequences, such as those described herein, or more stringent conditions. One skilled in the art can select posthybridization washing conditions, including temperature and salt concentrations, which reduce the number of nonspecific hybridizations such that only highly complementary sequences are identified (Sambrook et al. (1989) in *Molecular Cloning*, 2d ed.; Cold Spring Harbor Laboratory Press, Cold Spring Harbor, N.Y., hereby specifically incorporated by reference).

The isolated and purified polynucleotide sequences of the invention also include sequences complementary to the polynucleotide encoding MKK (antisense sequences). Antisense nucleic acids are DNA or RNA molecules that are complementary to at least a portion of a specific MRNA molecule (Weintraub (1990) Scientific American 262:40). The invention includes all antisense polynucleotides capable of inhibiting production of MKK polypeptides. In the cell, the antisense nucleic acids hybridize to the corresponding mRNA, forming a double-stranded molecule. Antisense oligomers of about 15 nucleotides are preferred, since they are easily synthesized and introduced into a target MKK-producing cell. The use of antisense methods to inhibit the translation of genes is known in the art, and is described, e.g., in Marcus-sakura Anal. Biochem., 172:289 (1988).

In addition, ribozyme nucleotide sequences for MKK are included in the invention. Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech (1988) J. Amer. Med. Assn. 260:3030). A major advantage of this approach is that, because they are sequence-specific, only mRNAs with particular sequences are inactivated.

There are two basic types of ribozymes namely, is tetrahymena-type (Hasselhoff (1988) Nature 334:585) and "hammerhead"-type. Tetrahymena-type ribozymes recognize sequences which are four bases in length, while "hammerhead"-type ribozymes recognize base sequences 11–18 bases in length. The longer the sequence, the greater the likelihood that the sequence will occur exclusively in the target mRNA species. Consequently, hammerhead-type ribozymes are preferable to tetrahymena-type ribozymes for inactivating a specific MRNA species, and 18-base recognition sequences are preferable to shorter recognition sequences.

The MKK polypeptides can also be used to produce antibodies that are immunoreactive or bind epitopes of the MKK polypeptides. Accordingly, one aspect of the invention features antibodies to the MKK polypeptides of the invention. The antibodies of the invention include polyclonal antibodies which consist of pooled monoclonal antibodies with different epitopic specificities, as well as distinct monoclonal antibody preparations. Monoclonal antibodies are made from antigen-containing fragments of the MKK polypeptide by methods known in the art (See, for example, Kohler et al. (1975) Nature 256:495).

The term "antibody" as used herein includes intact molecules as well as fragments thereof, such as Fa, $F(ab')_2$, and Fv, which are capable of binding the epitopic determinant. Antibodies that bind MKK polypeptides can be prepared using intact polypeptides or fragments containing small peptides of interest as the immunizing antigen. The polypeptide or peptide used to immunize an animal can be derived from translated cDNA or chemically synthesized, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The invention also features methods of identifying subjects at risk for MKK-mediated disorders by measuring activation of the MKK signal transduction pathway. Activation of the MKK signal transduction pathway can be determined by measuring MKK synthesis; activation of MKK isoforms; activation of MKK substrates p38 or JNK isoforms; or activation of p38 and JNK substrates such as ATF2, ATFa, CRE-BPa, and c-Jun. The term "JNK" or "JNK isoforms" includes both JNK1 and JNK2. The term "MKK substrate" as used herein include MKK substrates, as well as MKK substrate substrates, e.g., p38, JNK, ATF2, and c-Jun.

In one embodiment, activation of the MKK signal transduction pathway is determined by measuring activation of the MKK signal transduction pathway substrates p38, JNK isoforms, ATF2, or c-Jun. MKK activity is measured by the rate of substrate phosphorylation as determined by quantitation of the rate of $[^{32}P]$ incorporation. The specificity of MKK substrate phosphorylation can be tested by measuring p38 and JNK activation, or by employing mutated p38 and JNK molecules that lack the sites of MKK phosphorylations. Altered phosphorylation of the substrate relative to control values indicates alteration of the MKK signal transduction pathway, and increased risk in a subject of an MKK-mediated disorder. MKK activation of p38 and JNK can be detected in a coupled assay with the MKK signal transduction substrate ATF2, or related compounds such as ATFa and CRE-BPa. Activation can also be detected with the substrate c-Jun. When ATF2 is included in the assay, it is present as an intact protein or as a fragment of the intact protein, e.g., the activation domain (residues 1–109, or a portion thereof). ATF2 is incubated with a test sample in which MKK activity is to be measured and $[\gamma^{-32}P]ATP$, under conditions sufficient to allow the phosphorylation of ATF2. ATF2 is then isolated and the amount of phosphorylation quantitated. In a specific embodiment, ATF2 is isolated by immunoprecipitation, resolved by SDS-PAGE, and detected by autoradiography.

It another embodiment, activation of the MKK signal transduction pathway is determined by measuring the level of MKK expression in a test sample. In a specific embodiment, the level of MKK expression is measured by Western blot analysis. The proteins present in a sample are fractionated by gel electrophoresis, transferred to a membrane, and probed with labeled antibodies to MKK. In another specific embodiment, the level of MKK expression is measured by Northern blot analysis. Polyadenylated [poly (A)⁺] mRNA is isolated from a test sample. The mRNA is fractionated by electrophoresis and transferred to a membrane. The membrane is probed with labeled MKK cDNA. In another embodiment, MKK expression is measured by quantitative PCR applied to expressed mRNA.

The MKKs of the invention are useful to screen reagents that modulate MKK activity. MKKs are activated by phosphorylation. Accordingly, in one aspect, the invention features methods for identifying a reagent which modulates MKK activity, by incubating MKK with the test reagent and measuring the effect of the test reagent on MKK synthesis, phosphorylation, function, or activity. In one embodiment, the test reagent is incubated with MKK and [$^{32}$P]-ATP, and the rate of MKK phosphorylation determined, as described above. In another embodiment, the test reagent is incubated with a cell transfected with an MKK polynucleotide expression vector, and the effect of the test reagent on MKK transcription is measured by Northern blot analysis, as described above. In a further embodiment, the effect of the test reagent on MKK synthesis is measured by Western blot analysis using an antibody to MKK. In still another embodiment, the effect of a reagent on MKK activity is measured by incubating MKK with the test reagent, [$^{32}$P]-ATP, and a substrate in the MKK signal transduction pathway, including one or more of p38, JNK, and ATF2. The rate of substrate phosphorylation is determined as described above.

The term "modulation of MKK activity" includes inhibitory or stimulatory effects. The invention is particularly useful for screening reagents that inhibit MKK activity. Such reagents are useful for the treatment or prevention of MKK-mediated disorders, for example, inflammation and oxidative damage.

The invention further features a method of treating a MKK-mediated disorder by administering to a subject in need thereof an effective dose of a therapeutic reagent that inhibits the activity of MKK.

By the term "MKK-mediated disorder" is meant a pathological condition resulting, at least in part, from excessive activation of an MKK signal transduction pathway.

The MKK signal transduction pathways are activated by several factors, including inflammation and stress. MKK-mediated disorders include, for example, ischemic heart disease, burns due to heat or radiation (V, X-ray, i, g, etc.), kidney failure, liver damage due to oxidative stress or alcohol, respiratory distress syndrome, septic shock, rheumatoid arthritis, autoimmune disorders, and other types of inflammatory diseases.

As used herein, the term "therapeutic reagent" means any compound or molecule that achieves the desired effect on an MKK-mediated disorder when administered to a subject in need thereof.

MKK-mediated disorders further include proliferative disorders, particularly disorders that are stress-related. Examples of stress-related MKK-mediated proliferative disorders are psoriasis, acquired immune deficiency syndrome, malignancies of various tissues of the body, including malignancies of-the skin, bone marrow, lung, liver, breast, gastrointestinal system, and genito-urinary tract. Preferably, therapeutic reagents inhibit the activity or expression of MKK inhibit cell growth or cause apoptosis.

A therapeutic reagent that "inhibits MKK activity" interferes with a MKK-mediated signal transduction pathway. For example, a therapeutic reagent can alter the protein kinase activity of MKK, decrease the level of MKK transcription or translation, e.g., an antisense polynucleotide able to bind MKK mRNA, or suppress MKK phosphorylation of p38, JNK, or ATF2, thus disrupting the MKK-mediated signal transduction pathway. Examples of such reagents include antibodies that bind specifically to MKK polypeptides, and fragments of MKK polypeptides that competitively inhibit MKK polypeptide activity.

A therapeutic reagent that "enhances MKK activity" supplements a MKK-mediated signal transduction pathway. Examples of such reagents include the MKK polypeptides themselves, which can be administered in instances where the MKK-mediated disorder is caused by underexpression of the MKK polypeptide. In addition, portions of DNA encoding an MKK polypeptide can be introduced into cells that underexpress an MKK polypeptide.

A "therapeutically effective amount" is an amount of a reagent sufficient to decrease or prevent the symptoms associated with the MKK-mediated disorder.

Therapeutic reagents for treatment of MKK-mediated disorders identified by the method of the invention are administered to a subject in a number of ways known to the art, including parenterally by injection, infusion, sustained-release injection or implant, intravenously, intraperitoneally, intramuscularly, subcutaneously, or transdermally. Epidermal disorders and disorders of the epithelial tissues are treated by topical application of the reagent. The reagent is mixed with other compounds to improve stability and efficiency of delivery (e.g., liposomes, preservatives, or dimethyl sulfoxide (DMSO)). Polynucleotide sequences, including antisense sequences, can be therapeutically administered by techniques known to the art resulting in introduction into the cells of a subject suffering from the MKK-mediated disorder. These methods include the use of viral vectors (e.g., retrovirus, adenovirus, vaccinia virus, or herpes virus), colloid dispersions, and liposomes.

The materials of the invention are ideally suited for the preparation of a kit for the detection of the level or activity of MKK. Accordingly, the invention features a kit comprising an antibody that binds MKK, or a nucleic acid probe that hybridizes to a MKK polynucleotide, and suitable buffers. The probe or monoclonal antibody can be labeled to detect binding to a MKK polynucleotide or protein. In a preferred embodiment, the kit features a labeled antibody to MKK.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

The drawings will first be described.

Drawings

FIG. 1 is a comparison of the amino acid sequences of MKK3 (SEQ ID NO:2), MKK4-α (SEQ ID NO:6), the human MAP kinase kinases MEK1 (SEQ ID NO:11) and MEK2 (SEQ ID NO:12), and the yeast HOG1 MAP kinase kinase PBS2 (SEQ ID NO:13). MKK3 and MKK4 sequences were compared with the PILE-UP program (version 7.2; Wisconsin Genetics Computer Group). The protein sequences are presented in single letter code [A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp, and Y, Tyr]. The PBS2 sequence is truncated at both the $NH_2$— (<) and COOH— (>) termini. Gaps introduced into the sequences to optimize the alignment are illustrated by a dash. Identical residues are indicated by a period. The sites of activating phosphorylation in MEK are indicated by asterisks.

FIG. 2 is a dendrogram showing the relation between members of the human and yeast MAP kinase kinases. The dendrogram was created by the unweighted pair-group method with the use of arithmetic averages (PILE-UP program). The human (hu) MAP kinase kinases MEK1, MEK2, MKK3, and MKK4; the *Saccharomyces cerevisiae* (sc) MAP kinase kinases PBS2, MKK1, and STE7; and the *Saccharomyces pombe* (sp) MAP kinase kinases WIS1 and BYR1 are presented.

FIG. 3 is a schematic representation of the ERK, p38, and JNK signal transduction pathways. MEK1 and MEK2 are activators of the ERK subgroup of MAP kinase. MKK3 and MKK4 are activators of the p38 MAP kinase. MKK4 is identified as an activator of both the p38 and N subgroups of MAP kinase.

FIG. 4 is a representation of the nucleic acid (SEQ ID NO:1) and amino acid sequences (SEQ ID NO:2) for MKK3.

FIG. 5 is a representation of the nucleic acid (SEQ ID NO:3) and amino acid sequences (SEQ ID NO:4) for MKK6.

FIG. 6 is a representation of the nucleic acid (SEQ ID NO:5) and amino acid sequences (SEQ ID NO:6) for MKK4α.

FIG. 7 is a representation of the nucleic acid (SEQ ID NO:7) and amino acid sequences (SEQ ID NO:8) for MKK4β.

FIG. 8 is a representation of the nucleic acid (SEQ ID NO:9) and amino acid sequences (SEQ ID NO:10) for MKK4γ.

HUMAN MITOGEN-ACTIVATED PROTEIN KINASE KINASES

Figure 2:
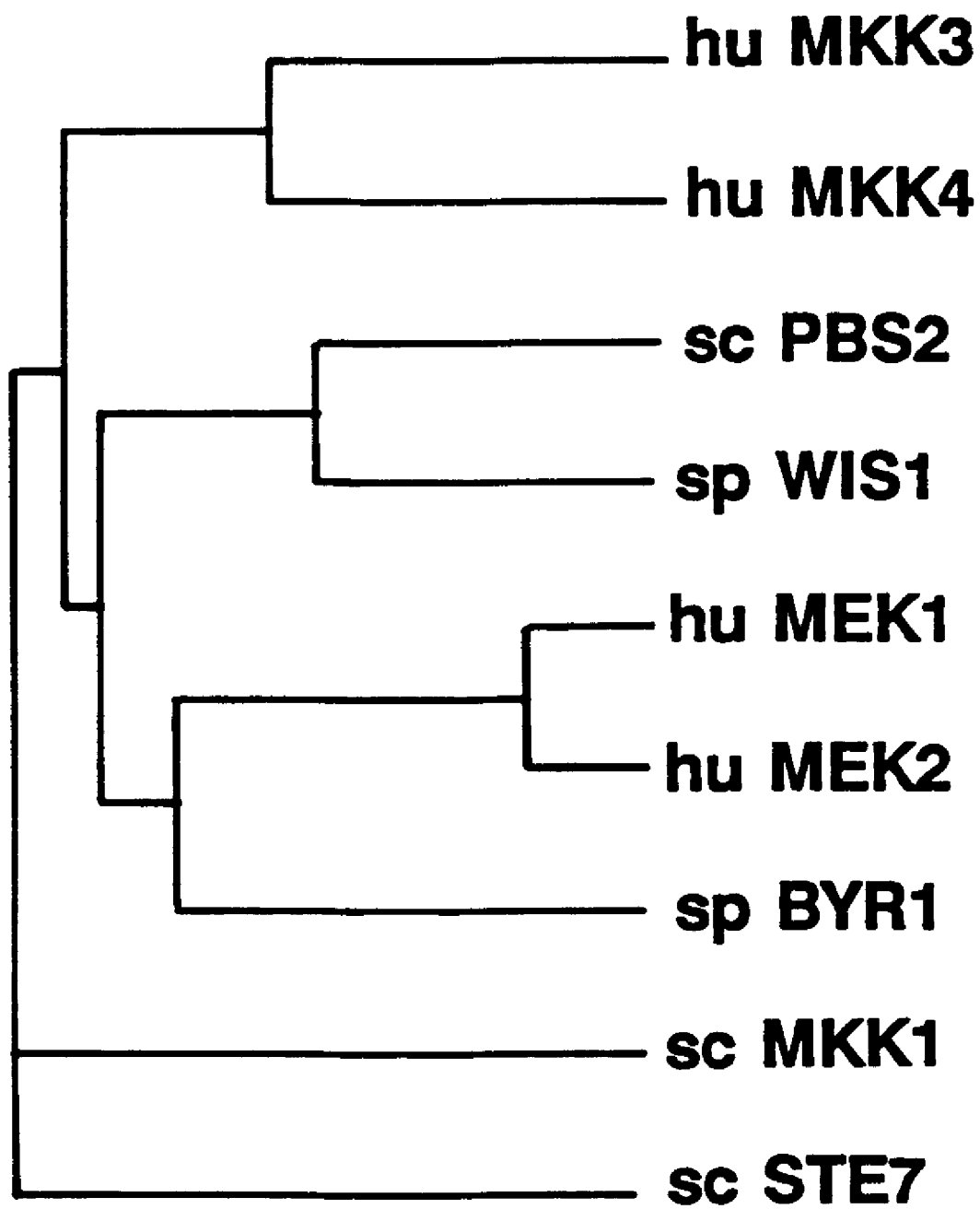

The human MAP kinase kinases MKK3 and MKK4 (MKK3/4) described herein mediate the transduction of specific signals from the cell surface to the nucleus along specific pathways. These signal transduction pathways are initiated by factors such as cytokines, UV radiation, osmotic shock, and oxidative stress. Activation of MKK3/4 results in activation of the MAP kinases p38 (MKK3/4) and JNK (MKK4). p38 and JNK in turn activate a group of related transcription factors such as ATF2, ATFa, and CRE-BPa. These transcription factors in turn activate expression of specific genes. For example, ATF2 in known to activate expression of human T cell leukemia virus 1 (Wagner and Green (1993) Science 262:395), transforming growth factor-b2 (Kim et al. (1992) supra), interferon-β (Du et al. (1993) Cell 74:887), and E-selectin (DeLuca et al. (1994) J. Biol. Chem. 269:19193). In addition, ATF2 is implicated in the function of a T cell-specific enhancer (Georgopoulos et al. (1992) Mol. Cell. Biol. 12:747).

The isolation of human MKKs is described in Example 1 and in Dérijard et al. (1995) Science 267:682–685, hereby specifically incorporated by reference. Distinctive regions of the yeast PBS2.sequence were used to design polymerase chain reaction (PCR) primers. Amplification of human brain mRNA with these primers resulted in the formation of specific products which were cloned into a plasmid vector and sequenced. Two different complementary DNAs (cDNAs) that encoded human protein kinases were identified: one encoding a 36 kD protein (MKK3), and one encoding a 44 kD protein (MKK4). MKK4 includes 3 isoforms that vary slightly at the $NH_2$-terminal, identified as α, β, and γ. The amino acid sequences of MKK3 (SEQ ID NO:2), MKK4-α (SEQ ID NO:6), MKK4-β (SEQ ID NO:8), and MKK4-γ (SEQ ID NO:10) are shown in FIG. 1. The nucleic acid and amino acid sequences of MKK3 (FIG. 5), MKK6 (FIG. 6), MKK4α (FIG. 7), MKK4β (FIG. 8), and MKK4γ (FIG. 9) are also provided. MKK6 was isolated from a human skeletal muscle library by cross-hybridization with MKK3. Except for differences at the N-terminus, MKK6 is highly homologous to MKK3. Other human MKK3 and MKK4 isoforms that exist can be identified by the method described in Example 1.

The expression of these human MKK isoforms was examined by Northern (RNA) blot analysis of mRNA isolated from eight adult human tissues (Example 2). Both protein kinases were found to be widely expressed in human tissues, with the highest expression seen in skeletal muscle tissue.

The substrate specificity of MKK3 was investigated in an in vitro phosphorylation assay with recombinant epitope-tagged MAP kinases (JNK1, p38, and ERK2) as substrates (Example 3). MKK3 phosphorylated p38, but did not phosphorylate JNK1 or ERK2. Phosphoaminoacid analysis of p38 demonstrated the presence of a phosphothreonine and phosphotyrosine. Mutational analysis of p38 demonstrated that replacement of phosphorylation sites $Thr^{180}$ and Tyr182 with Ala and Phe, respectively, blocked p38 phosphorylation. These results establish that MKK3 functions in vitro as a p38 MAP kinase kinase.

Studies of the in vitro substrate specificity of MKK4 are described in Example 4. MKK4 incubated with $[\gamma-^{32}P]ATP$, and JNK1, p38, or ERK2 was found to phosphorylate both p38 and JNK1. MKK4 activation of JNK and p38 was also studied by incubating MKK4 with wild-type or mutated JNK1 or p38. The p38 substrate ATF2 was included in each assay. MKK4 was found to exhibit less autophosphorylation than MKK3. MKK4 was also found to be a substrate for activated MAP kinase. Unlike MKK3, MKK4 was also found to activate JNK1. MKK4 incubated with wild-type JNK1, but not mutated JNK1, resulted in increased phosphorylation of ATF2. These results establish that MKK4 is a p38 MAP kinase kinase that also phosphorylates the JNK subgroup of MAP kinases.

In vivo activation of p38 by UV-stimulated MKK3 is described in Example 5. Cells expressing MKK3 were exposed in the presence or absence of UV radiation. MKK3 was isolated by immunoprecipitation and used for protein kinase assays with the substrates p38 or JNK. ATF2 was included in some assays as a substrate for p38 and JNK. MKK3 from non-activated cultured COS cells caused a small amount of phosphorylation of p38 MAP kinase, resulting from basal activity of MKK3. MKK3 from UV-irradiated cells caused increased phosphorylation of p38 MAP kinase, but not of JNK1. An increase in p38 activity was also detected in assays in which ATF2 was included as a substrate. These results establish that MKK3 is activated by UV radiation.

The effect of expression of MKK3 and MKK4 on p38 activity was examined in COS-1 cells (Example 6). Cells were transfected with a vector encoding p38 and a MEK1, MKK3, or MKK4. Some of the cells were also exposed to EGF or UV radiation. p38 was isolated by immunoprecipitation and assayed for activity with [$\gamma$-$^{32}$P]ATP and ATF2. The expression of the ERK activator MEK1 did not alter p38 phosphorylation of ATF2. In contrast, expression of MKK3 or MKK4 caused increased activity of p38 MAP kinase. The activation of p38 caused by MKK3 and MKK4 was similar to that observed in UV-irradiated cells, and was much greater than that detected in EGF-treated cells. These in vitro results provide evidence that MKK3 and MKK4 activate p38 in vivo.

A series of experiments was conducted to examine the potential regulation of ATF2 by JNK1. These experiments are described in Gupta et al. (1995) Science 267:389–393, hereby specifically incorporated by reference. The effect of UV radiation on ATF2 phosphorylation was investigated in COS-1 cells transfected with and without epitope-tagged JNK1 (Example 7). Cells were exposed to UV radiation, and JNK1 and JNK2 visualized by in-gel protein kinase assay with the substrate ATF2. JNK1 and JNK2 were detected in transfected and non-transfected cells exposed to UV radiation; however, JNK1 levels were higher in the transfected cells. These results demonstrate that ATF2 is a substrate for the JNK1 and JNK2 protein kinases, and that these protein kinases are activated in cells exposed to UV light.

The site of JNK1 phosphorylation of ATF2 was examined by deletion analysis (Example 8). Progressive NH2-terminal domain deletion GST-ATF2 fusion proteins were generated, and phosphorylation by JNK1 isolated from UV-irradiated cells was examined. The results showed that JNK1 requires the presence of ATF2 residues 1–60 for phosphorylation of the NH$_2$-terminal domain of ATF2.

The ATF2 residues required for binding of JNK1 were similarly examined. JNK1 was incubated with immobilized ATF2, unbound JNK1 was removed by extensive washing, and bound JNK1 was detected by incubation with [$\gamma$-$^{32}$P] ATP. Results indicate that residues 20 to 60 of ATF2 are required for binding and phosphorylation by JNK1. A similar binding interaction between ATF2 and the 55 kD JNK2 protein kinase has also been observed.

Phosphorylation by JNK1 was shown to reduce the electrophoretic mobility of ATF2 (Example 91. Phosphoamino acid analysis of the full-length ATF2 molecule (residues 1–505) demonstrated that JNK phosphorylated both Thr and Ser residues. The major sites of Thr and Ser phosphorylation were located in the NH$_2$ and COOH terminal domains, respectively. The NH$_2$-terminal sites of phosphorylation were identified as Thr$^{69}$ and Thr$^{71}$ by phosphopeptide mapping and mutational analysis. These sites of Thr phosphorylation are located in a region of ATF2 that is distinct from the sub-domain required for JNK binding (residues 20 to 60).

The reduced electrophoretic mobility seen with phosphorylation of ATF2 was investigated further (Example 10). JNK1 was activated in CHO cells expressing JNK1 by treatment with UV radiation, pro-inflammatory cytokine interleukin-1 (IL-1), or serum. A decreased electrophoretic mobility of JNK1-activated ATF2 was observed in cells treated with UV radiation and IL-1. Smaller effects were seen after treatment of cells with serum. These results indicate that ATF2 is an in vivo substrate for JNK1.

The effect of UV radiation on the properties of wild-type (Thr$^{69,71}$) and phosphorylation-defective (Ala$^{69,71}$) ATF2 molecules was investigated (Example 11). Exposure to UV caused a decrease in the electrophoretic mobility of both endogenous and over-expressed wild-type ATF2. This change in electrophoretic mobility was associated with increased ATF2 phosphorylation. Both the electrophoretic mobility shift and increased phosphorylation were blocked by the replacement of Thr69 and Thr$^{71}$ with Ala in ATF2. This mutation also blocked the phosphorylation of ATF2 on Thr residues in vivo.

Transcriptional activities of fusion proteins consisting of the GAL4 DNA binding domain and wild-type or mutant ATF2 were examined (Example 12). Point mutations at Thr$^{69}$ and/or Thr$^{71}$ of ATF2 significantly decreased the transcriptional activity of ATF2 relative to the wild-type molecule, indicating the physiological relevance of phosphorylation at these sites for activity.

The binding of JNK1 to the NH$_2$-terminal activation domain of ATF2 (described in Example 8) suggested that a catalytically inactive JNK1 molecule could function as a dominant inhibitor of the wild-type JNK1 molecule. This hypothesis was investigated by examining the effect of a catalytically inactive JNK1 molecule on ATF2 function (Example 13). A catalytically-inactive JNK1 mutant was constructed by replacing the sites of activating Thr$^{183}$ and Tyr$^{185}$ phosphorylation with Ala and Phe, respectively (Ala$^{183}$,Phe$^{185}$, termed "dominant-negative"). Expression of wild-type JNK1 caused a small increase in serum-stimulated ATF2 transcriptional activity. In contrast, dominant-negative JNK1 inhibited both control and serum-stimulated ATF2 activity. This inhibitory effect results from the non-productive binding of the JNK1 mutant to the ATF2 activation domain, effectively blocking ATF2 phosphorylation.

The tumor suppressor gene product Rb binds to ATF2 and increases ATF2-stimulated gene expression (Kim et al. (1992) Nature 358:331). Similarly, the adenovirus oncoprotein E1A associates with the DNA binding domain of ATF2 and increases ATF2-stimulated gene expression by a mechanism that requires the NH$_2$-terminal activation domain of ATF2 (Liu and Green (1994) Nature 368:520). ATF2 transcriptional activity was investigated with the luciferase reporter gene system in control, Rb-treated, and E1A-treated cells expressing wild-type or mutant ATF2 molecules (Example 14). Rb and E1A were found to increase ATF2-stimulated gene expression of both wild-type and mutant ATF2. However, mutant ATF2 caused a lower level of reporter gene expression than did wild-type ATF2. Together, these results indicate a requirement for ATF2 phosphorylation (on Thr$^{69}$ and Thr$^{71}$) plus either Rb or E1A for maximal transcriptional activity. Thus, Rb and E1A act in concert with ATF2 phosphorylation to control transcriptional activity.

A series of experiments were conducted to examine the action of p38 activation and to establish the relationship of the p38 MAP kinase pathway to the ERK and JNK signal transduction pathways (Raingeaud et al. (1995) J. Biol. Chem. 270:7420, hereby specifically incorporated by reference). Initially, the substrate specificity of p38 was investigated by incubating p38 with proteins that have been demonstrated to be substrates for the ERK and/or JNK groups of MAP kinases (Example 15). We examined the phosphorylation of MEP (Erickson et al. (1990) J. Biol. Chem. 265:19728), EGF-R (Northwood et al. (1991) J. Biol. Chem. 266:15266), cytoplasmic phospholipase A2 (cPLA$_2$) (Lin et al. (1993) Cell 72:269), c-Myc (Alvarez et al. (1991) J. Biol. Chem. 266:15277), IKE, c-Jun, and wild-type (Thr$^{69,71}$) or mutated (Ala$^{69,71}$) ATF2. p38 phosphorylated MBP and EGF-R, and to a lesser extent IKB, but not the other ERK substrates, demonstrating that the substrate specificity of p38 differs from both the ERK and JNK groups of MAP kinases. Wild-type ATF2, but not mutated ATF2 (Ala$^{69,71}$l), was found to be an excellent p38 substrate.

The phosphorylation of ATF2 by p38 was associated with an electrophoretic mobility shift of ATF2 during polyacrylamide gel electrophoresis. We tested the hypothesis that p38 phosphorylates ATF2 at the same sites as JNK1 by replacing Thr$^{69}$ and Thr$^{71}$ with Ala (Ala$^{69,71}$). It was found that p38 did not phosphorylate mutated ATF2, which demonstrates that p38 phosphorylates ATF2 within the NH$_2$-terminal activation domain on Thr69 and Thr$^{71}$.

A comparison of the binding of JNK and p38 to ATF2 was conducted by incubating extracts of cells expressing JNK1 or p38 with epitope alone (GST) or GST-ATF2 (residues 1–109 containing the activation domain) (Example 16). Bound protein kinases were detected by Western blot analysis. The results demonstrate that both p38 and JNK bind to the ATF2 activation domain.

EGF and phorbol ester are potent activators of the ERK signal transduction pathway (Egan and Weinberg (1993) Nature 365:781), causing maximal activation of the ERK sub-group of MAP kinases. These treatments, however, cause only a small increase in JNK protein kinase activity (Dérijard et al. (1994) supra; Hibi et al. (1993) supra). The effects of EGF or phorbol esters, as well UV radiation, osmotic shock, interleukin-1, tumor necrosis factor, and LPS, on p38 activity were all tested (Example 17). Significantly, EGF and phorbol ester caused only a modest increase in p38 protein kinase activity, whereas environmental stress (UV radiation and osmotic shock) caused a marked increase in the activity of both p38 and JNK. Both p38 and JNK were activated in cells treated with pro-inflammatory cytokines (TNF and IL-1) or endotoxic LPS. Together, these results indicate that p38, like JNK, is activated by a stress-induced signal transduction pathway.

ERKs and JNKs are activated by dual phosphorylation within the motifs Thr-Glu-Tyr and Thr-Pro-Tyr, respectively. In contrast, p38 contains the related sequence Thr-Gly-Tyr. To test whether this motif is relevant to the activation of p38, the effect of the replacement of Thr-Gly-Tyr with Ala-Gly-Phe was examined (Example 18). The effect of UV radiation on cells expressing wild-type (Thr$^{180}$,Tyr$^{182}$) or mutant p38 (Ala$^{180}$,Phe$^{182}$) was studied. Western blot analysis using an anti-phosphotyrosine antibody demonstrated that exposure to UV radiation caused an increase in the Tyr phosphorylation of p38. The increased Tyr phosphorylation was confirmed by phosphoaminoacid analysis of p38 isolated from [$\gamma$-$^{32}$P] phosphate-labeled cells. This analysis also demonstrated that UV radiation caused increased Thr phosphorylation of p38. Significantly, the increased phosphorylation on Thr$^{180}$ and Tyr$^{182}$ was blocked by the Ala$^{180}$/Phe$^{182}$ mutation. This result demonstrates that UV radiation causes increased activation of p38 by dual phosphorylation.

It has recently been demonstrated that ERK activity is regulated by the mitogen-induced dual specificity phosphatases MKP1 and PAC1 (Ward et al. (1994) Nature 367:651). The activation of p38 by dual phosphorylation (Example 18) raises the possibility that p38 may also be regulated by dual specificity phosphatases. We examined the effect of MKP1 and PAC1 on p38 MAP kinase activation (Example 19). Cells expressing human MKP1 and PAC1 were treated with and without UV radiation, and p38 activity measured. The expression of PAC1 or MKP1 was found to inhibit p38 activity. The inhibitory effect of MKP1 was greater than PAC1. In contrast, cells transfected with a catalytically inactive mutant phosphatase (mutant PAC1 Cys$^{257}$/Ser) did not inhibit p38 MAP kinase. These results demonstrate that p38 can be regulated by dual specificity phosphatases PAC1 and MKP1.

The sub-cellular distribution of p38 MAP kinase was examined by indirect immunofluorescence microscopy (Example 20). Epitope-tagged p38 MAP kinase was detected using the M2 monoclonal antibody. Specific staining of cells transfected with epitope-tagged p38 MAP kinase was observed at the cell surface, in the cytoplasm, and in the nucleus. Marked changes in cell surface and nuclear p38 MAP kinase were not observed following UV irradiation, but an increase in the localization of cytoplasmic p38 MAP kinase to the perinuclear region was detected.

A series of experiments were conducted to study the activation of JNK by hyper-osmotic media (Example 21). These experiments were reported by Galcheva-Gargova et al. (1994) Science 265:806, hereby specifically incorporated by reference. CHO cells expressing epitope-tagged JNK1 were incubated with 0–1000 mM sorbitol, and JNK1 activity measured in an immune complex kinase assay with the substrate c-Jun. Increased JNK1 activity was observed in cells incubated 1 hour with 100 mM sorbitol. Increased JNK1 activity was observed within 5 minutes of exposure to 300 mM sorbitol. Maximal activity was observed 15 to 30 minutes after osmotic shock with a progressive decline in JNK1 activity at later times. The activation of JNK by osmotic shock was studied in cells expressing wild-type (Thr$^{183}$, Tyr$^{185}$) or mutated (Ala$^{183}$, Phe$^{185}$) JNK1. JNK1 activity was measured after incubation for 15 minutes with or without 300 mM sorbitol. Cells expressing wild-type JNK1 showed increased JNK1 activity, while cells expressing mutated JNK1 did not. These results demonstrate that the JNK signal transduction pathway is activated in cultured mammalian cells exposed to hyper-osmotic media.

Figure 3:
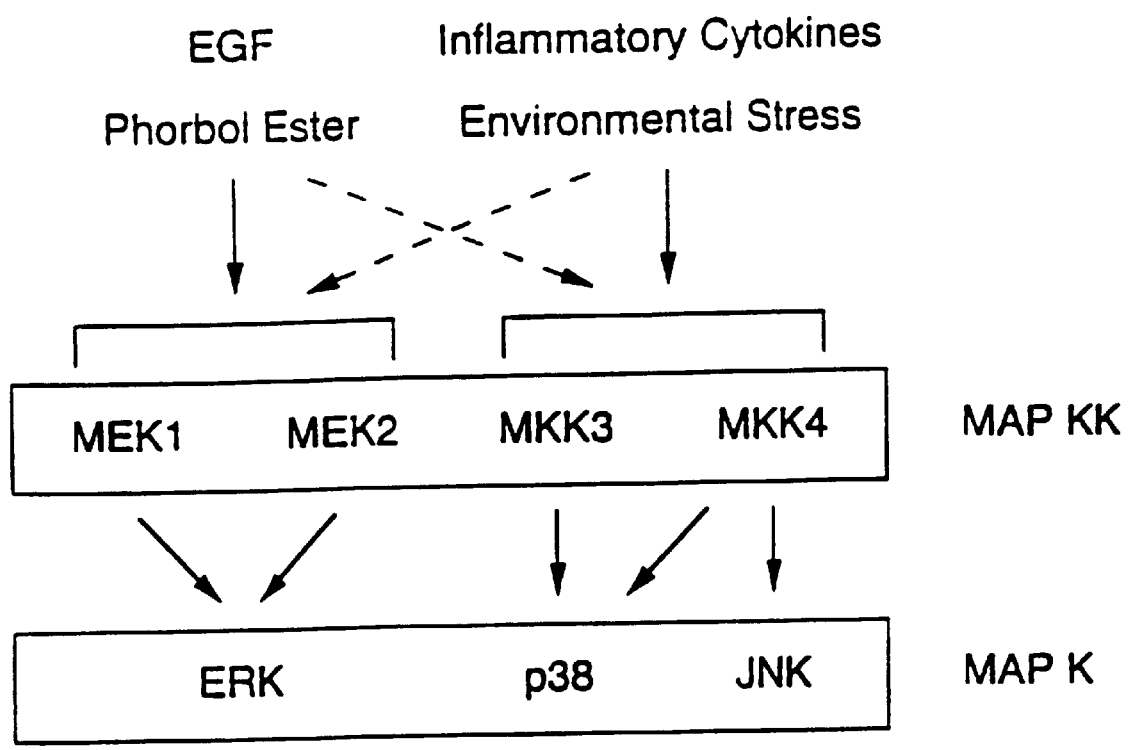

The results of the above-described experiments are illustrated in FIG. 3, which diagrams the ERK, p38, and JNK MAP kinase signal transduction pathways. ERKs are potently activated by treatment of cells with EGF or phorbol esters. In contrast, p38 is only slightly activated under these conditions (Example 15). However, UV radiation, osmotic stress, and inflammatory cytokines cause a marked increase in p38 activity. This difference in the pattern of activation of ERK and p38 suggests that these MAP kinases are regulated by different signal transduction pathways. The molecular basis for the separate identity of these signal transduction pathways is established by the demonstration that the MAP kinase kinases that activate ERK (MEK1 and MEK2) and p38 (MKK3 and MKK4) are distinct.

MKK isoforms are useful for screening reagents which modulate MKK activity. Described in the Use section following the examples are methods for identifying reagents capable of inhibiting or activating MKK activity.

The discovery of human MKK isoforms and MKK-mediated signal transduction pathways is clinically significant for the treatment of MKK-mediated disorders. One use of the MKK isoforms is in a method for screening reagents able to inhibit or prevent the activation of the MKK-MAP kinase-ATF2 pathways.

The following examples are meant to illustrate, not limit, the invention.

EXAMPLE 1

MKK Protein Kinases

The primary sequences of MKK3 and MKK4 were deduced from the sequence of cDNA clones isolated from a human fetal brain library.

The primers TTYTAYGGNGCNTTYTTYATHGA (SEQ ID NO:14) and ATBCTYTCNGGNGCCATKTA (SEQ ID NO:15) were designed based on the sequence of PBS2 (Brewster et al. (1993) Science 259:1760; Maeda et al. (1994) Nature 369:242). The primers were used in a PCR reaction with human brain mRNA as template. Two sequences that encoded fragments of PBS2-related protein kinases were identified. Full-length human cDNA clones were isolated by screening of a human fetal brain library (Dérijard et al. (1994) supra). The cDNA clones were examined by sequencing with an Applied Biosystems model 373A machine. The largest clones obtained for MKK3 (2030 base pairs (bp)) and MKK4 (3576 bp) contained the entire coding region of these protein kinases.

The primary structures of MKK3 (SEQ ID NO:2) and MKK4α (SEQ ID NO:6) are shown in FIG. 1. An in-frame termination codon is located in the 5' untranslated region of the MKK3 CDNA, but not in the 5' region of the MKK4 cDNA. The MKK4 protein sequence presented starts at the second in-frame initiation codon.

These sequences were compared to those of the human MAP kinase kinases MEK1 (SEQ ID NO:11) and MEK2 (SEQ ID NO:12) (Zheng and Guan (1993) J. Biol. Chem 268:11435) and of the yeast MAP kinase kinase PBS2 (SEQ ID NO:13) (Boguslawaski and Polazzi (1987) Proc. Natl. Acad. Sci. USA 84:5848) (FIG. 1). The identity and similarity of the kinases with human MKK3 (between subdomains I and XI) were calculated with the BESTFIT program (version 7.2; Wisconsin Genetics Computer Group) (percent of identity to percent of similarity): MEK1, 41%/63%; MEK2, 41%/62%; MKK4α, 52%/73%; and PBS2, 40%/59%. The identity and similarity of the kinases with human MKK4a were calculated to be as follows (percent of identity to percent of similarity): MEK1, 44%/63%; MEK2, 45%/61%; MKK3, 52%/73%; and PBS2, 44%/58%.

The cDNA sequences of MKK3 and MKK4γ have been deposited in GenBank with accession numbers L36719 and L36870, respectively. The MKK4γ cDNA sequence contains both the cDNA sequences of MKK4α and MKK4β, which are generated in vivo from alternate splicing sites. One of ordinary skill in the art can readily determine the amino acid sequences of MKK3 and MKK4 isoforms from the deposited cDNA sequences.

EXAMPLE 2

Expression of MKK3 and MKK4 mRNA in Adult Human Tissue

Northern blot analysis was performed with polyadenylated, [poly(A)$^+$] mRNA (2 μg) isolated from human heart, brain, placenta, lung, liver, muscle, kidney, and pancreas tissues. The MRNA was fractionated by denaturing agarose gel electrophoresis and was transferred to a nylon membrane. The blot was probed with the MKK3 and MKK4 cDNA labeled by random priming with [α-$^{32}$P]ATP (deoxyadenosine triphosphate) (Amersham International PLC). MKK3 and MKK4 were expressed in all tissues examined; the highest expression of MKK3 and MKK4 was found in skeletal muscle tissue.

The relation between members of the human and yeast MAP kinase kinase group is presented as a dendrogram (FIG. 2). MKK3/4 form a unique subgroup of human MAP kinase kinases.

EXAMPLE 3

In Vitro Phosphorylation of p38 MAP kinase by MKK3

GST-JNK1, and GST-ERK2 have been described (Dérijard et al. (1994) supra; Gupta et al. (1995) Science 267:389; Wartmann and Davis (1994) J. Biol. Chem. 269:6695, each herein specifically incorporated by reference). GST-p38 MAP kinase was prepared from the expression vector pGSTag (Dressier et al. (1992) Biotechniques 13:866) and a PCR fragment containing the coding region of the p38 MAP kinase cDNA. GST-MKK3 and MKK4 were prepared with pGEX3X (Pharmacia-LKB Biotechnology) and PCR fragments containing the coding region of the MKK3 and MKK4 cDNAs. The GST fusion proteins were purified by affinity chromatography with the use of GSH-agarose (Smith and Johnson (1988) Gene 67:31). The expression vectors pCMV-Flag-JNK1 and pCMV-MEK1 have been described (Dérijard et al. (1994) supra; Wartmann and Davis (1994) supra). The plasmid pCMV-Flag-p38 MAP kinase was prepared-with the expression vector pCMV5 (Andersson et al. (1989) J. Biol. Chem. 264:8222) and the p38 MAP kinase cDNA. The expression vectors for MKK3 and MKK4 were prepared by subcloning of the cDNAs into the polylinker of pCDNA3 (Invitrogen). The Flag epitope (Asp-Tyr-Lys-Asp-Asp-Asp-Asp-Lys (SEQ ID NO:16); Immunex, Seattle, Wash.) was inserted between codons 1 and 2 of the kinases by insertional overlapping PCR (Ho et al. (1989) Gene 77:51).

Protein kinase assays were performed in kinase buffer (25 mM 4-(2-hydroxyethyl)-1-piperazineethansulfonic acid, pH 7.4, 25 mM β-glycerophosphate, 25 mM MgCl$_2$, 2 mM dithiothreitol, and 0.1 mM orthovanadate). Recombinant GST-MKK3 was incubated with [γ-$^{32}$P]ATP and buffer, GST-JNK1, GST-p38 MAP kinase, or GST-ERK2. The assays were initiated by the addition of 1 μg of substrate proteins and 50 μM [γ-$^{32}$P]ATP (10 Ci/mmol) in a final volume of 25 μl. The reactions were terminated after 30 minutes at 25° C. by addition-of Laemmli sample buffer. The phosphorylation of the substrate proteins was examined after SDS-polyacrylamide gel electrophoresis (SDS-PAGE) by autoradiography. Phosphoaminoacid analysis was performed by partial acid hydrolysis and thin-layer chromatography (Dérijard et al. (1994) supra; Alvarez et al. (1991) J. Biol. Chem. 266:15277). Autophosphorylation of MKK3 was observed in all groups. MKK3 phosphorylated p38 MAP kinase, but not JNK1 or ERK2.

A similar insertional overlapping PCR procedure was used to replace Thr$^{180}$ and Tyr$^{182}$ of p38, with Ala and Phe, respectively. The sequence of all plasmids was confirmed by automated sequencing on an Applied Biosystems model 373A machine. GST-MKK3 was incubated with [γ-$^{32}$P]ATP and buffer, wild-type GST-p38 MAP kinase (TGY), or mutated GST-p38 MAP kinase (AGF). The phosphorylated proteins were resolved by SDS-PAGE and detected by autoradiography. Only phosphorylation of wild-type p38 was observed.

EXAMPLE 4

In Vitro Phosphorylation and Activation of JNK and p38 MAP Kinase by MKK4

Protein kinase assays were conducted as described in Example 3. Recombinant GST-MKK4 was incubated with [γ-$^{32}$P]ATP and buffer, GST-JNK1, GST-p38 MAP kinase, or GST-ERK2. JNK1 and p38 were phosphorylated, as was MKK4 incubated with JNK1 and p38.

GST-MKK4 was incubated with [γ-$^{32}$P]ATP and buffer, wild-type JNK1 (Thr$^{183}$, Tyr$^{185}$), or mutated GST-JNK1 (Ala$^{183}$, Phe$^{185}$). The JNK1 substrate ATF2 (Gupta et al. (1995) supra) was included in each incubation. ATF2 was phosphorylated in the presence of MKK4 and wild-type JNK1. The results establish that MKK4 phosphorylates and activates both p38 and JNK1.

EXAMPLE 5

Phosphorylation and Activation of p38 MAP Kinase by UV-stimulated MKK3

Epitope-tagged MKK3 was expressed in COS-1 cells maintained in Dulbecco's modified Eagle's medium supplemented with fetal bovine serum (5%) (Gibco-BRL). The cells were transfected with the lipofectamine reagent according to the manufacturer's recommendations (Gibco-BRL) and treated with UV radiation or EGF as described (Dérijard et al. (1994) supra).

The cells were exposed in the absence and presence of UV-C (40 J/m$^2$). The cells were solubilized with lysis buffer (20 mM tris, pH 7.4, 1% TRITON X-100, 10% glycerol, 137 mM NaCl, 2 mM EDTA, 25 mM β-glycerophosphate, 1 mM Na orthovanadate, 1 mM phenylmethylsulfonyl fluoride, and leupeptin (10 μg/ml)) and centrifuged at 100,000×g for 15 minutes at 4° C. MKK3 was isolated by immunoprecipitation. The epitope-tagged protein kinases were incubated for 1 hour at 4° C. with the M2 antibody to the Flag epitope (IBI-Kodak) bound to protein G-Sepharose (Pharmacia-LKB Biotechnology). The immunoprecipitates were washed twice with lysis buffer and twice with kinase buffer.

Protein kinase assays were conducted with the substrate GST-p38 MAP kinase or JNK1. ATF2 was included in some assays. Basal levels of MKK3 phosphorylation of p38 MAP kinase were observed. UV-irradiation resulted in increased phosphorylation of p38 MAP kinase, but not of JNK1. The increased p38 MAP kinase activity resulted in increased phosphorylation of ATF2.

EXAMPLE 6

Activation of p38 MAP Kinase in Cells Expressing MKK3 and MKK4

COS-1 cells were transfected with epitope-tagged p38 MAP kinase, together with an empty expression vector or an expression vector encoding MEK1, MKK3, or MKK4α. Some of the cultures were exposed to UV radiation (40 J/m$^2$) or treated with 10 nM EGF. p38 MAP kinase was isolated by immunoprecipitation with M2 monoclonal antibody, and the protein kinase activity was measured in the immunecomplex with [γ-$^{32}$P]ATP and ATF2 as substrates. The product of the phosphorylation reaction was visualized after SDS-PAGE by autoradiography. ATF2 was not phosphorylated in the control MEK1, or EGF-treated groups, but was phosphorylated in the MKK3, MKK4, and UV-irradiated groups. MKK3 and MKK4 phosphorylation of ATF2 was similar to that seen with p38 MAP kinase isolated from UV-irradiated cells.

EXAMPLE 7

Phosphorylation of ATF2 by JNK1 and JNK2

COS-1 cells were maintained in Dulbecco's modified Eagle's medium supplemented with bovine serum albumin (5%) (Gibco-BRL). Metabolic labeling with [$^{32}$P]P was performed by incubation of cells for 3 hours in phosphate-free modified Eagle's medium (Flow Laboratories Inc.) supplemented with [$^{32}$P]orthophosphate (2 mCi/ml) (Dupont-NEN). COS-1 cells were transfected without (Mock) and with epitope-tagged JNK1 (JNK1). Plasmid expression vectors encoding the JNK1 cDNA have previously been described (Dérijard et al. (1994) Cell 76:1025, herein specifically incorporated by reference). Plasmid DNA was transfected into COS-1 cells by the lipofectamine method (Gibco-ERL). After 48 hours of incubation, some cultures were exposed to 40 J/m$^2$ UV radiation and incubated for 1 hour at 37° C.

Cells were lysed in 20 mM Tris, pH 7.5, 25 mM β-glycerophosphate, 10% glycerol, 1% TRITON X-100, 0.5% (w/v) deoxycholate, 0.1% (w/v) SDS, 0.137 M NaCl, 2 mM pyrophosphate, 1 mM orthovanadate, 2 mM EDTA, 10 μg/ml leupeptin, 1 mM PMSF. Soluble extracts were prepared by centrifugation in a microfuge for 20 minutes at 4° C. JNK1 immunoprecipitates were also prepared by reaction with a rabbit antiserum prepared with recombinant JNK1 as an antigen.

In-gel protein kinase assays were performed with cell lysates and JNK1 immunoprecipitates after SDS-PAGE by renaturation of protein kinases, polymerization of the substrate (GST-ATF2, residues 1–505) in the gel, and incubation with [γ-$^{32}$P] ATP (Dérijard et al. (1994) supra). The incorporation of [$^{32}$P] phosphate was visualized by autoradiography and quantitated with a Phosphorimager and ImageQuant soft-ware (Molecular Dynamics Inc., Sunnyvale, Calif.). The cell lysates demonstrate the presence of 46 kD and 55 kD protein kinases that phosphorylate ATF2 in extracts prepared from UV-irradiated cells. The 46 kD and 55 kD protein kinases were identified as JNK1 and JNK2, respectively.

EXAMPLE 8

Binding of JNK1 to ATF2 and Phosphorylation of the NH$_2$-Terminal Activation Domain The site of JNK1 phosphorylation of ATF2 was investigated by generation of progressive NH$_2$-terminal domain deletions of ATF2. Plasmid expression vectors encoding ATF2 (pECE-ATF2) (Liu and Green (1994) and (1990)), have been described. Bacterial expression vectors for GST-ATF2 fusion proteins were constructed by sub-cloning ATF2 cDNA fragments from a polymerase chain reaction (PCR) into pGEX-3X (Pharmacia-LKB Biotechnology Inc.). The sequence of all constructed plasmids was confirmed by automated sequencing with an Applied Biosystems model 373A machine.

The GST-ATF2 proteins were purified as described (Smith and Johnson (1988) Gene 67:31), resolved by SDS-PAGE and stained with Coomassie blue. GST-ATF2 fusion proteins contained residues 1–505, 1–349, 350–505, 1–109, 20–109, 40–109, and 60–109.

The phosphorylation of GST-ATF2 fusion proteins by JNK1 isolated from UV-irradiated cells was examined in an immunocomplex kinase assay. Immunecomplex kinase assays were performed with Flag epitope-tagged JNK1 and the monoclonal antibody M2 (IBI-Kodak) as described by Dérijard et al. (1994) supra). Immunecomplex protein kinase assays were also performed with a rabbit antiserum prepared with recombinant JNK1 as an antigen. The cells were solubilized with 20 mM Tris, pH 7.5, 10% glycerol, 1% TRITON X-100, 0.137 M NaCl, 25 mM β-glycerophosphate, 2 mM EDTA, 1 mM orthovanadate, 2 mM pyrophosphate, 10 μg/ml leupeptin, and 1 mM PMSF. JNK1 was immunoprecipitated with protein G-Sepharose bound to a rabbit polyclonal antibody to JNK or the M2 monoclonal antibody to the Flag epitope. The beads were washed three times with lysis buffer and once with kinase buffer (20 mM Hepes, pH 7.6, 20 mM MgCl$_2$, 25 mM glycerophosphate, 100 μM Na orthovanadate, 2 mM dithiothreitol). The kinase assays were performed at 25° C. for 10 minutes with 1 μg of substrate, 20 μM adenosine triphosphate and 10 μCi of [γ-$^{32}$P]ATP in 30 μl of kinase buffer. The reactions were terminated with Laemmli sample buffer and the products were resolved by SDS-PAGE (10% gel). JNK1 phosphorylates GST-ATF2 fusion proteins containing residues 1–505, 1–349, 1–109, 20–109, and 40–109, but not 60–109. These results indicate that the presence of ATF2 residues 1–60 are required for phosphorylation by JNK.

The binding of immobilized GST-ATF2 fusion proteins was examined in a solid-phase kinase assay as described by Hibi et al. (1993) Genes Dev. 7:2135, herein specifically incorporated by reference. JNK1 from UV-irradiated cells was incubated with GST-ATF2 fusion proteins bound to GSH-agarose. The agarose beads were washed extensively to remove the unbound JNK1. Phosphorylation of the GST-ATF2 fusion proteins by the bound JNK1 protein kinase was examined by addition of $[\gamma^{-32}P]ATP$. JNK1 bound GST-ATF2 fusion proteins containing residues 1–505, 1–349, 1–109, 20–109, and 40–109, indicating that the presence of residues 20–60 were required for binding of JNK1 to ATF2.

EXAMPLE 9

Phosphorylation of the $NH_2$-terminal Activation Domain of ATF2 on $Thr^{69}$ and $Thr^{71}$ by JNK1

The effect of UV radiation on the properties of wild-type ($Thr^{69,71}$) and phosphorylation-defective ($Ala^{69,71}$) ATF2 molecules was examined. Mock-transfected and JNK1-transfected COS cells were treated without and with 40 $J/m^2$ UV radiation. The epitope-tagged JNK1 was isolated by immunoprecipitation with the M2 monoclonal antibody. The phosphorylation of GST-ATF2 (residues 1 to 109) was examined in an immunocomplex kinase assay as described above. The GST-ATF2 was resolved from other proteins by SDS-PAGE and stained with Coomassie blue. The phosphorylation of GST-ATF2 was detected by autoradiography. JNK1-transfected cells, but not mock-transfected cells, phosphorylated ATF2. JNK1 phosphorylation of ATF2 was greater in cells exposed to UV radiation. Phosphorylation of ATF2 by JNK1 was associated with a decreased electrophoretic mobility.

In a separate experiment, GST fusion proteins containing full-length ATF2 (residues 1 to 505), an $NH_2$-terminal fragment (residues 1 to 109), and a COOH-terminal fragment (residues 95 to 505) were phosphorylated with JNK1 and the sites of phosphorylation analyzed by phosphoamino acid analysis. The methods used for phosphopeptide mapping and phosphoamino acid analysis have been described (Alvarez et al. (1991) J. Biol. Chem. 266:15277). The horizontal dimension of the peptide maps was electrophoresis and the vertical dimension was chromatography. The $NH_2$-terminal sites of phosphorylation were identified as $Thr^{69}$ and $Thr^{71}$ by phosphopeptide mapping and mutational analysis. Site-directed mutagenesis was performed as described above, replacing $Thr^{69}$ and $Thr^{71}$ with Ala. Phosphorylation of mutated ATF2 was not observed.

EXAMPLE 10

Reduced Electrophoretic Mobility of JNK-Activated ATF2

CHO cells were maintained in Ham's F12 medium supplemented with 5% bovine serum albumin (Gibco-BRL). Cells were labeled and transfected with JNK1 as described above. CHO cells were treated with UV-C (40 $J/m^2$), IL-1α (10 ng/ml) (Genzyme), or fetal bovine serum (20%) (Gibco-BRL). The cells were incubated for 30 minutes at 37° C. prior to harvesting. The electrophoretic mobility of ATF2 after SDS-PAGE was examined by protein immuno-blot analysis. A shift in ATF2 electrophoretic mobility was observed in cells treated with UV, IL-1, and serum. These results indicate that JNK1 activation is associated with an electrophoretic mobility shift of ATF2, further suggesting that ATF2 is an in vivo substrate for JNK1.

EXAMPLE 11

Increased ATF2 Phosphorylation After Activation of JNK

COS-1 cells were transfected without (control) and with an ATF2 expression vector (ATF2), as described above (Hai et al. (1989) supra). The effect of exposure of the cells to 40 $J/m^2$ UV-C was examined. After irradiation, the cells were incubated for 0 or 30 minutes (control) or 0, 15, 30, and 45 minutes (ATF2) at 37° C. and then collected. The electrophoretic mobility of ATF2 during SDS-PAGE was examined by protein immuno-blot analysis as described above. The two electrophoretic mobility forms of ATF2 were observed in ATF2-transfected cells, but not in control cells.

The phosphorylation state of wild-type ($Thr^{69,71}$) ATF2 and mutated ($Ala^{69,71}$) ATF2 was examined in cells labeled with $[^{32}P]$, treated without and with 40 $J/m^2$ UV-C, and then incubated at 37° C. for 30 minutes (Hai et al. (1989) supra). The ATF2 proteins were isolated by immunoprecipitation and analyzed by SDS-PAGE and autoradiography. The phosphorylated ATF2 proteins were examined by phospho-amino acid analysis as described above. Both forms of ATF2 contained phosphoserine, but only wild-type ATF2 contained phosphothreonine.

Tryptic phosphopeptide mapping was used to compare ATF2 phosphorylated in vitro by JNK1 with ATF2 phosphorylated in COS-1 cells. A map was also prepared with a sample composed of equal amounts of in vivo and in vitro phosphorylated ATF2 (Mix). Mutation of ATF2 at $Thr^{69}$ and $Thr^{71}$ resulted in the loss of two tryptic phosphopeptides in maps of ATF2 isolated from UV-irradiated cells. These phosphopeptides correspond to mono- and bis-phosphorylated peptides containing $Thr^{69}$ and $Thr^{71}$. Both of these phosphopeptides were found in maps of ATF2 phosphorylated by JNK1 in vitro.

EXAMPLE 12

Inhibition of ATF2-Stimulated Gene Expression by Mutation of the Phosphorylation Sites $Thr^{69}$ and $Thr^{71}$ A fusion protein consisting of ATF2 and the GAL4 DNA binding domain was expressed in CHO cells as described above. The activity of the GAL4-ATF2 fusion protein was measured in co-transfection assays with the reporter plasmid pG5E1bLuc (Seth et al. (1992) J. Biol. Chem. 267:24796, hereby specifically incorporated by reference). The reporter plasmid contains five GAL4 sites cloned upstream of a minimal promoter element and the firefly luciferase gene. Transfection efficiency was monitored with a control plasmid that expresses β-galactosidase (pCH110; Pharmacia-LKB Biotechnology). The luciferase and β-galactosidase activity detected in cell extracts was measured as the mean activity ratio of three experiments (Gupta et al. (1993) Proc. Natl. Acad. Sci. USA 90:3216, hereby specifically incorporated by reference). The results shown in Table 1, demonstrate the importance of phosphorylation at $Thr^{69}$ and $Thr^{71}$ for transcriptional activity.

TABLE 1

INHIBITION OF ATF-2 STIMULATED GENE EXPRESSION BY MUTATION OF THE PHOSPHORYLATION SITES $THR^{69, 71}$

| PROTEIN | LUCIFERASE ACTIVITY (Light Units/OD) |
|---|---|
| GAL4 | 45 |
| GAL4-ATF2 (wild type) | 320,000 |
| GAL4-ATF2 ($Ala^{69}$) | 24,000 |
| GAL4-ATF2 ($Ala^{71}$) | 22,000 |
| GAL4-ATF2 ($Ala^{69, 71}$) | 29,000 |
| GAL4-ATF2 ($Glu^{69}$) | 27,000 |

EXAMPLE 13

Effect of Dominant-Negative JNK1 Mutant on ATF2 Function

The luciferase reporter plasmid system was used to determine the effect of point mutations at the ATF2 phosphorylation sites $Thr^{69}$ and $Thr^{71}$ in serum-treated CHO cells transfected with wild-type ($Thr^{183}$, $Tyr^{185}$) or mutant ($Ala^{183}$, $Phe^{185}$) JNK1. Control experiments were done with mock-transfected cells. The CHO cells were serum-starved for 18 hours and then incubated without or with serum for 4 hours. Expression of wild-type ATF2 caused a small increase in serum-stimulated ATF2 transcriptional activity. In contrast, mutant JNK1 inhibited both control and serum-stimulated ATF2 activity.

EXAMPLE 14

Effect of Tumor Suppressor Gene Product Rb and Adenovirus Oncoprotein E1A on ATF2-Stimulated Gene Expression The effect of expression of the Rb tumor suppressor gene product and adenovirus oncoprotein E1A on ATF2 transcriptional activity were investigated with a luciferase reporter plasmid and GAL4-ATF2 (residues 1–505), as described above. Cells were transfected with wild-type ($Thr^{69,71}$) or mutated (Ala69,71) ATF2. No effect of Rb or E1A on luciferase activity was detected in the absence of GAL4-ATF2. Rb and E1A were found to increase ATF2-stimulated gene expression of both wild-type and mutated ATF2. However, mutated ATF2 caused a lower level of reporter gene expression than did wild-type ATF2. These results indicate a requirement for ATF2 phosphorylation (on $Thr^{69}$ and $Thr^{71}$) plus either Rb or E1A for maximal transcriptional activity.

EXAMPLE 15

Substrate Specificity of D38 MAP Kinase

Substrate phosphorylation by p38 MAP kinase was examined by incubation of bacterially-expressed p38 MAP kinase with IKB, cMyc, EGF-R, cytoplasmic phospholipase $A_2$ ($cPLA_2$), c-Jun, and mutated ATF2 ($Thr^{69,71}$) and ATP[$\gamma$-$^{32}$P] (Raingeaud et al. (1995) J. Biol. Chem 270:7420, herein specifically incorporated by reference). GST-IκB was provided by Dr D. Baltimore (Massachusetts Institute of Technology). GST-cMyc (Alvarez et al. (1991) J. Biol. Chem. 266:15277), GST-EGF-R (residues 647–688) (Koland et al. (1990) Biochem. Biophys. Res. Commun. 166:90), and GST-c-Jun (Dérijard et al. (1994) supra) have been described. The phosphorylation reaction was terminated after 30 minutes by addition of Laemmli sample buffer. The phosphorylated proteins were resolved by SDS-PAGE and detected by autoradiography. The rate phosphorylation of the substrate proteins was quantitated by PhosphorImager (Molecular Dynamics Inc.) analysis. The relative phosphorylation of ATF2, MBP, EGF-R, and IκB was 1.0, 0.23, 0.04, and 0.001, respectively.

EXAMPLE 16

Binding of p38 MAP Kinase to ATF2

Cell extracts expressing epitope-tagged JNK1 and p38 MAP kinase were incubated with a GST fusion protein containing the activation domain of ATF2 (residues 1–109) immobilized on GSH agarose. The supernatant was removed and the agarose was washed extensively. Western blot analysis of the supernatant and agarose-bound fractions was conducted as follows: proteins were fractionated by SDS-PAGE, electrophoretically transferred to an Immobilon-P membrane, and probed with monoclonal antibodies to phosphotyrosine (PY20) and the Flag epitope (M2). Immunocomplexes were detected using enhanced chemiluminescence (Amersham International PLC). Control experiments were performed using immobilized GST.

EXAMPLE 17 p38 MAP Kinase and JNK1 Activation by Pro-Inflammatory Cytokines and Environmental Stress The effect of phorbol ester, EGF, UV radiation, osmotic stress, IL-1, tumor necrosis factor (TNF), and LPS on p38 MAP kinase and JNK1 activity were measured in immunecomplex protein kinase assays using ATP[$\gamma$-$^{32}$]P and ATF2 as substrates. TNF$\alpha$ and IL-1$\alpha$ were from Genzyme Corp. Lipolysaccharide (LPS) was isolated from lyophilized *Salmonella minesota* Re595 bacteria as described (Mathison et a. (1988) J. Clin. Invest. 81:1925). Phorbol myristate acetate was from Sigma. EGF was purified from mouse salivary glands (Davis (1988) J. Biol. Chem. 263:9462). Kinase assays were performed using immunoprecipitates of p38 and JNK. The immunocomplexes were washed twice with kinase buffer (described above),-and the assays initiated by the addition of 1 $\mu$g of ATF2 and 50 $\mu$M [$\gamma^{32}$P]ATP (10 Ci/mmol) in a final volume of 25 $\mu$l. The reactions were terminated after 30 minutes at 30° C. by addition of Laemmli sample buffer. The phosphorylation of ATF2 was examined after SDS-PAGE by autoradiography, and the rate of ATF2 phosphorylation quantitated by PhosphorImager analysis.

The results are shown in Table 2. Exposure of HeLa cells to 10 nM phorbol myristate acetate very weakly activated p38 and JNK1. Similarly, treatment with 10 nM EGF only weakly activated p38 and JNK1. By contrast, treatment with 40 J/$m^2$ UV-C, 300 mM sorbitol, 10 ng/ml interleukin-1, and 10 ng/ml TNFA strongly activated p38 and JNK1 activity. The effect of LPS on the activity of p38 was examined using CHO cells that express human CD14. Exposure of CHO cells to 10 ng/ml LPS only slightly activated p38 and JNK1 activity.

TABLE 2 p38 AND JNK1 ACTIVATION BY PRO-INFLAMMATORY CYTOKINES AND ENVIRONMENTAL STRESS.

| | Relative Protein Kinase Activity | |
|---|---|---|
| | JNK | p38 |
| Control | 1.0 | 1.0 |
| Epidermal Growth Factor (10 nM) | 1.9 | 2.1 |
| Phorbol Ester (10 nM) | 2.3 | 2.9 |
| Lipopolysaccharide (10 ng/ml) | 3.6 | 3.7 |
| Osmotic Shock (300 mM sorbitol) | 18.1 | 4.2 |
| Tumor Necrosis Factor (10 ng/ml) | 19.3 | 10.3 |
| Interleukin-1 (10 ng/ml) | 8.9 | 6.2 |
| UV (40 J/$m^2$) | 7.4 | 17.1 |

EXAMPLE 18 p38 MAP Kinase Activation by Dual Phosphorylation on Tyr and Thr

COS-1 cells expressing wild-type ($Thr^{180}$, $Tyr^{182}$) or mutated ($Ala^{180}$; $Phe^{182}$) p38 MAP kinase were treated without and with UV-C (40 J/$m^2$). The cells were harvested 30 minutes following exposure with or without UV radiation. Control experiments were performed using mock-transfected cells. The level of expression of epitope-tagged p38 MAP kinase and the state of Tyr phosphorylation of p38

MAP kinase was examined by Western blot analysis using the M2 monoclonal antibody and the phosphotyrosine monoclonal antibody PY20. Immune complexes were detected by enhanced chemiluminescence.

Wild-type and mutant p38 were expressed at similar levels. Western blot analysis showed that UV radiation caused an increase in the Tyr phosphorylation of p38. The increased Tyr phosphorylation was confirmed by phospho-amino acid analysis of p38 isolated from [$^{32}$P]phosphate-labeled cells. The results also showed that UV radiation increased Thr phosphorylation of p38. The increased phosphorylation on Tyr and Thr was blocked by mutated p38. Wild-type and mutated p38 were isolated from the COS-1 cells by immunoprecipitation. Protein kinase activity was measured in the immune complex using [$\gamma$-$^{32}$P]ATP and GST-ATF2 as substrates. The phosphorylated GST-ATF2 was detected after SDS-PAGE by autoradiography. UV radiation resulted in a marked increase in the activity of wild-type p38, while the mutant p38 was found to be catalytically inactive. These results show that p38 is activated by dual phosphorylation within the Thr-Gly-Tyr motif.

EXAMPLE 19

MAP Kinase Phosphatase Inhibits p38 MAP kinase Activation

The cells were treated without and with 40 J/m$^2$ UV-C. Control experiments were performed using mock-transfected cells (control) and cells transfected with the catalytically inactive mutated phosphatase mPAC1 (Cys$^{257}$/Ser) and human MKP1. The activity of p38 MAP kinase was measured with an immunecomplex protein kinase assay employing [$\gamma$-$^{32}$P]ATP and GST-ATF2 as substrates. The expression of PAC1 or MKP1 was found to inhibit p38 phosphorylation, demonstrating that p38 can be regulated by the dual specificity phosphatases PAC1 and MKP1.

EXAMPLE 20

Subcellular Distribution of p38 MAP Kinase

Epitope-tagged p38 MAP kinase was expressed in COS cells. The cells were treated without or with 40 J/m$^2$ UV radiation and then incubated for 60 minutes at 37° C. The p38 MAP kinase was detected by indirect immunofluorescence using the M2 monoclonal antibody. The images were acquired by digital imaging microscopy and processed for image restoration.

Immunocytochemistry. Coverslips (22mm×22mm No. 1; Gold Seal Cover Glass; Becton-Dickinson) were pre-treated by boiling in 0.1 N HCl for 10 minutes, rinsed in distilled water, autoclaved and coated with 0.01% poly-L-lysine (Sigma; St. Louis, Mo.). The coverslips were placed at the bottom of 35 mm multiwell tissue culture plates (Becton Dickinson, UK). Transfected COS-1 cells were plated directly on the coverslips and allowed to adhere overnight in Dulbecco's modified Eagle's medium supplemented with 5% fetal calf serum (Gibco-BRL). 24 hours post-transfection, the cells were rinsed once and incubated at 37° C. for 30 minutes in 25 mM Hepes, pH 7.4, 137 mM NaCl, 6 mM KCl, 1 mM MgCl$_2$, 1 mM CaCa$_2$, 10 mM glucose. The cells were rinsed once with phosphate-buffered saline and the coverslips removed from the tissue culture wells. Cells were fixed in fresh 4% paraformaldehyde in phosphate-buffered saline for 15 minutes at 22° C. The cells were permeabilized with 0.25% TRITON X-100 in phosphate-buffered saline for 5 minutes and washed three times in DWB solution (150 mM NaCl, 15 mM Na citrate, pH 7.0, 2% horse serum, 1% (w/v) bovine serum albumin, 0.05% TRITON X-100) for 5 minutes. The primary antibody (M2 anti-FLAG monoclonal antibody, Eastman-Kodak Co., New Haven, Ct.) was diluted 1:250 in DWB and applied to the cells in a humidified environment at 22° C. for 1 hour. The cells were again washed three times as above and fluorescein isothiocyanate-conjugated goat anti-mouse Ig secondary antibody (Kirkegaard & Perry Laboratories Inc. Gaithersburg, Md.) was applied at a 1:250 dilution for 1 hour at 22° C. in a humidified environment. The cells were then washed three times in DWE and then mounted onto slides with Gel-Mount (Biomeda Corp. Foster City, Calif.) for immunofluorescence analysis. Control experiments were performed to assess the specificity of the observed immunofluorescence. No fluorescence was detected when the transfected cells were stained in the absence of the primary M2 monoclonal antibody, or mock-transfected cells.

Digital Imaging Microscopy and Image Restoration

Digital images of the fluorescence distribution in single cells were obtained using a Nikon 60× Planapo objective (numerical aperture=1.4) on a Zeiss IM-35 microscope equipped for epifluorescence as previously described (Carrington et al. (1990) in: Non-invasive Techniques in Cell Biology (Fosbett & Grinstein, eds.), Wiley-Liss, NY; pp. 53–72; Fay et al. (1989) J. Microsci. 153:133–149). Images of various focal planes were obtained with a computer controlled focus mechanism and a thermoelectrically cooled charged-coupled device camera (model 220; Photometrics Ltd., Tucson, Ariz.). The exposure of the sample to the excitation source was determined by a computer-controlled shutter and wavelength selector system (MVI, Avon, Mass.). The charge-coupled device camera and microscope functions were controlled by a microcomputer, and the data acquired from the camera were transferred to a Silicon Graphics model 4D/GTX workstation (Mountainview, Calif.) for image processing. Images were corrected for non-uniformities in sensitivity and for the dark current of the charge coupled device detector. The calibration of the microscopy blurring was determined by measuring the instrument's point spread function as a series of optical sections at 0.125 $\mu$m intervals of a 0.3 $\mu$m diameter fluorescently labeled latex bead (Molecular Probes Inc.). The image restoration algorithm used is based upon the theory of ill-posed problems and obtains quantitative dye density values within the cell that are substantially more accurate than those in an un-processed image (Carrington et al. (1990) supra; Fay et al. (1989) supra). After image processing, individual optical sections of cells were inspected and analyzed using computer graphics software on a Silicon Graphics workstation. p38 MAP kinase was observed at the cell surface, in the cytoplasm, and in the nucleus. After irradiation, an increased localization of cytoplasmic p38 to the perinuclear region was detected.

EXAMPLE 21

Activation of the MKK Signal Transduction Pathway by Osmotic Shock

CHO cells were co-transfected with the plasmid pCMV-Flag-Jnk1 and pRSV-Neo (Dérijard et al. (1994) supra). A stable cell line expressing epitope-tagged Jnk1 (Flag; Immunex Corp.) was isolated by selection with Geneticin (Gibco-BRL). The cells were incubated with 0, 100, 150, 300, 600, or 1000 mM sorbitol for 1 hour at 37° C. The cells were collected in lysis buffer (20 mM Tris, pH 7.4, 1% TRITON X-100, 2 mM EDTA, 137 mM NaCl, 25 mM $\beta$-glycerophosphate, 1 mM orthovanadate, 2 mM pyrophosphate, 10% glycerol, 1 mM phenylmethylsulfonyl fluoride, 10 $\mu$g/ml leupeptin) and a soluble extract was obtained by centrifugation at 100,000 g for 30 minutes at 4°

C. The epitope-tagged JNK1 was isolated by immunoprecipitation with the monoclonal antibody M2 (Immunex Corp.). The immunoprecipitates were washed extensively with lysis buffer. Immunecomplex kinase assays were done in 25 µl of 25 mM Hepes, pH 7.4, 25 mM MgCl$_2$, 25 mM β-glycerophosphate, 2 mM dithiothreitol, 100 µM orthovanadate, and 50 µM ATP [γ-$^{32}$P] (10 Ci/mmole) with 2.5 µg of bacterially expressed c-Jun (residues 1–79) fused to glutathione-S-transferase (GST) as a substrate. The phosphorylation of c-Jun was examined after SDS-PAGE by autoradiography and PhosphorImager (Molecular Dynamics Inc.) analysis. JNK1 activation was observed-at all concentrations of sorbitol exposure.

The time course of JNK1 protein kinase activation was measured in cells incubated in medium supplemented with 300 mM sorbitol as described above. Increased JNK1 activity 25 was observed within 5 minutes of exposure to sorbitol, with maximum activity occurring after 15–30 minutes.

Mutation of JNK1 at the phosphorylation sites Thr$^{183}$ and Tyr$^{185}$ blocked the activation of JNK1 protein kinase activity by osmotic shock. CHO cells were transfected with vector, wild-type JNK1 (Thr$^{183}$, Tyr$^{185}$), and mutated JNK1 (Ala$^{183}$, Phe$^{185}$). The cells were incubated in medium supplemented without or with 300 mM sorbitol for 15 minutes before measurement of JNK1 protein kinase activity as described above. JNK1 activation was seen in the wild-type but not mutated JNK1.

Use

The MKK polypeptides and polynucleotides of the invention are useful for identifying reagents which modulate the MKK signal transduction pathways. Reagents that modulate an MKK signal transduction pathway can be identified by their effect on MKK synthesis, MKK phosphorylation, or MKK activity. For example, the effect of a reagent on MKK activity can be measured by the in vitro kinase assays described above. MKK is incubated without (control) and with a test reagent under conditions sufficient to allow the components to react, then the effect of the test reagent on kinase activity is subsequently measured. Reagents that inhibit an MKK signal transduction pathway can be used in the treatment of MKK-mediated disorders. Reagents that stimulate an MKK signal transduction pathway can be used in a number of ways, including induction of programmed cell death (apoptosis) in tissues. For example, the elimination of UV damaged cells can be used to prevent cancer.

Generally, for identification of a reagent that inhibits the MKK signal transduction pathway, the kinase assay is tested with a range of reagent concentrations, e.g., 1.0 nM to 100 mM, a MKK substrate, and a radioactive marker such as [γ-$^{32}$P]ATP. Appropriate substrate molecules include p38, JNK1, JNK2, or ATF2. The incorporation of [$^{32}$]P into the substrate is determined, and the results obtained with the test reagent compared to control values. Of particular interest are reagents that result in inhibition of [$^{32}$]P of about 80% or more.

Assays that test the effect of a reagent on MKK synthesis can also be used to identify compounds that inhibit MKK signal transduction pathways. The effect of the test reagent on MKK expression is measured by, for example, Western blot analysis with an antibody specific for MKK. Antibody binding is visualized by autoradiography or chemiluminescence, and is quantitated. The effect of the test reagent on MKK mRNA expression can be examined, for example, by Northern blot analysis using a polynucleotide probe or by polymerase chain reaction.

Reagents found to inhibit MKK signal transduction pathways can be used as therapeutic agents for the treatment of MKK-mediated disorders. Such reagents are also useful in drug design for elucidation of the specific molecular features needed to inhibit MKK signal transduction pathways.

In addition, the invention provides a method for the treatment of MKK-mediated stress-related and inflammatory disorders. The method includes administration of an effective amount of a therapeutic reagent that inhibits MKK function. Suitable reagents inhibit either MKK activity or expression. The concentration of the reagent to be administered is determined based on a number of factors, including the appropriate dosage, the route of administration, and the specific condition being treated. The appropriate dose of a reagent is determined by methods known to those skilled in the art including routine experimentation to optimize the dosage as necessary for the individual patient and specific MKK-mediated disorder being treated. Specific therapeutically effective amounts appropriate for administration are readily determined by one of ordinary skill in the art (see, for example, *Remington's Pharmaceutical Sciences.* 18th ed., Gennaro, ed., Mack publishing Company, Easton, Pa., 1990).

The invention provides methods for both acute and prophylactic treatment of-stress-related and inflammatory disorders. For example, it is envisioned that ischemic heart disease will be treated during episodes of ischemia and oxidative stress following reperfusion. In addition, a patient at risk for ischemia can be treated prior to ischemic episodes.

In another example, a therapeutic agent which inhibits MKK function or activity is administered to control inflammatory responses by inhibiting the secretion of inflammatory cytokines, including TNF and IL-1.

Stress-related proliferative disorders can also be treated by the method of the invention by administering a therapeutic reagent that inhibits MKK function or activity. Such therapeutic reagents can be used alone or in combination with other therapeutic reagents, for example, with chemotherapeutic agents in the treatment of malignancies. Indeed, the control of stress-activated MKK by the therapeutic reagents provided by this invention can modulate symptoms caused by other therapeutic strategies that induce stress.

The therapeutic reagents employed are compounds which inhibit MKK function or activity, including polynucleotides, polypeptides, and other molecules such as antisense oligonucleotides and ribozymes, which can be made according to the invention and techniques known to the art. Polyclonal or monoclonal antibodies (including fragments or derivatives thereof) that bind epitopes of MKK also can be employed as therapeutic reagents. Dominant-negative forms of MKK which effectively displace or compete with MKK for substrate binding and/or phosphorylation can be used to decrease protein kinase activity. Dominant-negative forms can be created by mutations within the catalytic domain of the protein kinases, as described above.

In some cases, augmentation of MKK activity is desirable, e.g., induction of apoptosis. The methods of the invention can be used to identify reagents capable of increasing MKK function or activity. Alternatively, increased activity is achieved by over-expression of MKK. When a MKK-mediated disorder is associated with under-expression of MKK, or expression of a mutant MKK polypeptide, a sense polynucleotide sequence (the DNA coding strand) or MKK polypeptide can be introduced into the cell.

The antibodies of the invention can be administered parenterally by injection or by gradual infusion over time. The monoclonal antibodies of the invention can be administered intravenously, intraperitoneally, intramuscularly, subcutaneously, intracavity, or transdermally.

Preparations for parenteral administration of a polypeptide or an antibody of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and the like. Preservatives and other additives can also be present, such as, for example, antimicrobials, antioxidants, chelating agents, and inert gases, and the like.

Polynucleotide sequences, including antisense sequences, can be therapeutically administered by various techniques known to those skilled in the art. Such therapy would achieve its therapeutic effect by introduction of the MKK polynucleotide into cells of mammals having a MKK-mediated disorder. Delivery of MKK polynucleotides can be achieved using free polynucleotide or a recombinant expression vector such as a chimeric virus or a colloidal dispersion system. Especially preferred for therapeutic delivery of nucleotide sequences is the use of targeted liposomes.

Targeting of the therapeutic reagent to specific tissues is desirable to increase the efficiency of delivery. The targeting can be achieved by passive mechanisms via the route of administration. Active targeting to specific tissues can also be employed. The use of liposomes, colloidal suspensions, and viral vectors allows targeting to specific tissues by changing the composition of the formulation containing the therapeutic reagent, for example, by including molecules that act as receptors for components of the target tissues. Examples include sugars, glycoplipids, polynucleotides, or proteins. These molecules can be included with the therapeutic reagent. Alternatively, these molecules can be included by indirect methods, for example, by inclusion of a polynucleotide that encodes the molecule, or by use of packaging systems that provide targeting molecules. Those skilled in the art will know, or will ascertain with the use of the teaching provided herein, which molecules and procedures will be useful for delivery of the therapeutic reagent to specific tissues.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method for identifying a reagent that modulates mitogen-activating protein kinase kinase (MKK) activity, the method comprising:
   a) obtaining a test sample containing an MKK polypeptide and a reagent;
   b) incubating the test sample with an MKK substrate for an MKK polypeptide having serine, threonine, and tyrosine kinase activity, and phosphorylating human mitogen activated protein (MAP) kinase p38; and with labeled phosphate under conditions sufficient to allow phosphorylation of the substrate;
   c) determining the rate of incorporation of labeled phosphate into the substrate, wherein the rate of incorporation is a measure of MKK activity; and
   d) comparing the effect of the reagent on MKK activity relative to a control, wherein a change in MKK activity indicates the presence of a reagent able to modulate MKK activity.

2. A method of claim 1 wherein said MKK substrate is one or more of p38, JNK, ATF2, ATFa, CRE-BPa, and c-Jun.

3. A method of claim 1 wherein said modulation is inhibition of MKK activity.

4. The method of claim 1, wherein the reagent is selected from the group consisting of a polynucleotide, a polypeptide, and an antibody.

5. The method of claim 1, wherein the reagent is selected from the group consisting of an antisense oligonucleotide and a ribozyme.

6. The method of claim 1, wherein the reagent is selected from the group consisting of a cytokine, UV irradiation, and osmotic shock.

7. The method of claim 1, wherein the reagent is selected from the group consisting of a tumor necrosis factor and an interleukin-1.

8. The method of claim 1, wherein the MKK is selected from the group consisting of an MKK3, MKK4α, MKK4β, MKK4γ, and MKK6.

9. The method of claim 1, wherein the MKK is a human MKK.

10. A method for identifying a reagent that modulates MKK synthesis, the method comprising:
   a) providing a test sample containing an MKK polypeptide;
   b) incubating the test sample in the presence of a reagent;
   c) fractionating proteins present in the sample by gel electrophoresis;
   d) transferring the proteins onto a membrane;
   e) probing the proteins with a labeled antibody specific to an MKK polypeptide having serine, threonine, and tyrosine kinase activity, and phosphorylating human mitogen activated protein (MAP) kinase p38, wherein the level of MKK synthesis is determined by the amount of antibody detected; and
   f) comparing the effect of the reagent on MKK synthesis relative to a control, wherein a change in MKK synthesis indicates the presence of a reagent able to modulate MKK synthesis.

11. A method of claim 10 wherein said MKK substrate is one or more of p38, JNK, ATF2, ATFa, CRE-BPa, and c-Jun.

12. A method of claim 10, wherein said modulation is inhibition of MKK synthesis.

13. The method of claim 10, wherein the reagent is selected from the group consisting of a polynucleotide, a polypeptide, and an antibody.

14. The method of claim 10, wherein the reagent is selected from the group consisting of an anti sense oligonucleotide and a ribozyme.

15. The method of claim 10, wherein the reagent is selected from the group consisting of a cytokine, UV irradiation, and osmotic shock.

16. The method of claim 10, wherein the reagent is selected from the group consisting of a tumor necrosis factor and an interleukin-1.

17. The method of claim 10, wherein the MKK is selected from the group consisting of an MKK3, MKK4α, MKK4β, MKK4γ, and MKK6.

18. The method of claim 10, wherein the MKK is a human MKK.

19. A method for identifying a reagent that modulates mitogen-activating protein kinase kinase (MKK) expression, the method comprising:
   a) providing a test sample in which an MKK polynucleotide is expressed;
   b) incubating the test sample in the presence of a reagent;
   c) isolating polyadenylated RNA from the test sample;
   d) incubating the polyadenylated RNA with a polynucleotide probe specific for an MKK polypeptide having serine, threonine, and tyrosine kinase activity, and phosphorylating human mitogen activated protein (MAP) kinase p38;
   e) determining the amount of the probe hybridized to the polyadenylated RNA, wherein the level of expression of MKK is directly related to the amount of MKK probe hybridized to the RNA; and
   f) comparing the effect of the reagent on MKK expression relative to a control, wherein a change in MKK expression indicates the presence of a reagent able to modulate MKK expression.

20. The method of claim 19, wherein the reagent is selected from the group consisting of a polynucleotide, a polypeptide, and an antibody.

21. The method of claim 19, wherein the reagent is selected from the group consisting of an antisense oligonucleotide and a ribozyme.

22. The method of claim 19, wherein the reagent is selected from the group consisting of a cytokine, UV irradiation, and osmotic shock.

23. The method of claim 19, wherein the reagent is selected from the group consisting of a tumor necrosis factor and an interleukin-1.

24. The method of claim 19, wherein the MKK is selected from the group consisting of an MKK3, MKK4α, MKK4β, MKK4γ, and MKK6.

25. The method of claim 19, wherein the MKK is a human MKK.

26. A kit useful for the detection of mitogen-activating protein kinase kinase (MKK), said kit comprising a buffer and an antibody which specifically binds to a MKK polypeptide having serine, threonine, and tyrosine kinase activity, and phosphorylating human mitogen activated protein (MAP) kinase p38, wherein the sample to be tested is mixed with the buffer and the antibody, and wherein the antibody is labeled.

27. The kit of claim 24, wherein the MKK is selected from the group consisting of an MKK3, MKK4α, MKK4β, MKK4γ, and MKK6.

28. The kit of claim 24, wherein the MKK is a human MKK.

29. A kit useful for the detection of mitogen-activating protein kinase kinase (MKK) nucleic acid, said kit comprising a buffer and nucleic acid molecule comprising at least about 20 nucleotides and hybridizing to a nucleic acid sequence selected from the group consisting of MKK3, MKK4α, MKK4β, MKK4γ, MKK6, or a complement thereof under stringent hybridization conditions.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 2030 base pairs
      (B) TYPE: nucleic acid
      (C) STRANDEDNESS: single
      (D) TOPOLOGY: linear (xi) SEQUENCE DESCRIPTION: SEQ ID NO:1:

```
TGGCTGGCAA TGGCCTTGCT GACCTCGAGC CGGGCCCACG TGGGGACCTT TGGAGCACAG      60

CCTACGATCC TGGTGCAAGG CCGGTGGATG CAGAGGCCAG TCCATATACC ACCCAGGCCT     120

GCGAGGAGCG TGGTCCCCAC CCATCCAGCC CATATGTGCA AGTGCCCTTG ACAGAGAGGC     180

TGGTCATATC CATGGTGACC ATTTATGGGC CACAACAGGT CCCCATCTGC GCAGTGAACC     240

CTGTGCTGAG CACCTTGCAG ACGTGATCTT GCTTCGTCCT GCAGCACTGT GCGGGGCAGG     300

AAAATCCAAG AGGAAGAAGG ATCTACGGAT ATCCTGCATG TCCAAGCCAC CCGCACCCAA     360

CCCCACACCC CCCCGGAACC TGGACTCCCG GACCTTCATC ACCATTGGAG ACAGAAACTT     420

TGAGGTGGAG GCTGATGACT TGGTGACCAT CTCAGAACTG GGCCGTGGAG CCTATGGGGT     480

GGTAGAGAAG GTGCGGCACG CCCAGAGCGG CACCATCATG GCCGTGAAGC GGATCCGGGC     540

CACCGTGAAC TCACAGGAGC AGAAGCGGCT GCTCATGGAC CTGGACATCA ACATGCGCAC     600

GGTCGACTGT TTCTACACTG TCACCTTCTA CGGGGCACTA TTCAGAGAGG GAGACGTGTG     660

GATCTGCATG GAGCTCATGG ACACATCCTT GGACAAGTTC TACCGGAAGG TGCTGGATAA     720

AAACATGACA ATTCCAGAGG ACATCCTTGG GGAGATTGCT GTGTCTATCG TGCGGGCCCT     780

GGAGCATCTG CACAGCAAGC TGTCGGTGAT CCACAGAGAT GTGAAGCCCT CCAATGTCCT     840
```

-continued

```
TATCAACAAG GAGGGCCATG TGAAGATGTG TGACTTTGGC ATCAGTGGCT ACTTGGTGGA      900

CTCTGTGGCC AAGACGATGG ATGCCGGCTG CAAGCCCTAC ATGGCCCCTG AGAGGATCAA      960

CCCAGAGCTG AACCAGAAGG GCTACAATGT CAAGTCCGAC GTCTGGAGCC TGGGCATCAC     1020

CATGATTGAG ATGGCCATCC TGCGGTTCCC TTACGAGTCC TGGGGGACCC CGTTCCAGCA     1080

GCTGAAGCAG GTGGTGGAGG AGCCGTCCCC CCAGCTCCCA GCCGACCGTT TCTCCCCCGA     1140

GTTTGTGGAC TTCACTGCTC AGTGCCTGAG GAAGAACCCC GCAGAGCGTA TGAGCTACCT     1200

GGAGCTGATG GAGCACCCCT TCTTCACCTT GCACAAAACC AAGAAGACGG ACATTGCTGC     1260

CTTCGTGAAG AAGATCCTGG GAGAAGACTC ATAGGGGCTG GGCCTCGGAC CCCACTCCGG     1320

CCCTCCAGAG CCCCACAGCC CCATCTGCGG GGGCAGTGCT CACCCACACC ATAAGCTACT     1380

GCCATCCTGG CCCAGGGCAT CTGGGAGGAA CCGAGGGGGC TGCTCCCACC TGGCTCTGTG     1440

GCGAGCCATT TGTCCCAAGT GCCAAAGAAG CAGACCATTG GGGCTCCCAG CCAGGCCCTT     1500

GTCGGCCCCA CCAGTGCCTC TCCCTGCTGC TCCTAGGACC CGTCTCCAGC TGCTGAGATC     1560

CTGGACTGAG GGGGCCTGGA TGCCCCCTGT GGATGCTGCT GCCCCTGCAC AGCAGGCTGC     1620

CAGTGCCTGG GTGGATGGGC ACCGCCTTG CCCAGCCTGG ATGCCATCCA AGTTGTATAT      1680

TTTTTTAATC TCTCGACTGA ATGGACTTTG CACACTTTGG CCCAGGGTGG CCACACCTCT     1740

ATCCCGGCTT TGGTGCGGGG TACACAAGAG GGGATGAGTT GTGTGAATAC CCCAAGACTC     1800

CCATGAGGGA GATGCCATGA GCCGCCCAAG GCCTTCCCCT GGCACTGGCA AACAGGGCCT     1860

CTGCGGAGCA CACTGGCTCA CCCAGTCCTG CCCGCCACCG TTATCGGTGT CATTCACCTT     1920

TCGTGTTTTT TTTAATTTAT CCTCTGTTGA TTTTTTCTTT TGCTTTATGG GTTTGGCTTG     1980

TTTTTCTTGC ATGGTTTGGA GCTGATCGCT TCTCCCCCAC CCCCTAGGGG                2030
```

(2) INFORMATION FOR SEQ ID NO:2:

(i) SEQUENCE CHARACTERISTICS:
        (A) LENGTH: 318 amino acids
        (B) TYPE: amino acid
        (C) STRANDEDNESS: Not Relevant
        (D) TOPOLOGY: linear (xi) SEQUENCE DESCRIPTION: SEQ ID NO:2:

```
Met Ser Lys Pro Pro Ala Pro Asn Pro Thr Pro Pro Arg Asn Leu Asp
1               5                   10                  15

Ser Arg Thr Phe Ile Thr Ile Gly Asp Arg Met Phe Glu Val Glu Ala
            20                  25                  30

Asp Asp Leu Val Thr Ile Ser Glu Leu Gly Arg Gly Ala Tyr Gly Val
        35                  40                  45

Val Glu Lys Val Arg His Ala Gln Ser Gly Thr Ile Met Ala Val Lys
    50                  55                  60

Arg Ile Arg Ala Thr Val Asn Ser Gln Glu Gln Lys Arg Leu Leu Met
65                  70                  75                  80

Asp Leu Asp Ile Asn Met Arg Thr Val Asp Cys Phe Tyr Thr Val Thr
            85                  90                  95

Phe Tyr Gly Ala Leu Phe Arg Glu Gly Asp Val Trp Ile Cys Met Glu
            100                 105                 110

Leu Met Asp Thr Ser Leu Asp Lys Phe Tyr Arg Lys Val Leu Asp Lys
        115                 120                 125

Asn Met Thr Ile Pro Glu Asp Ile Leu Gly Glu Ile Ala Val Ser Ile
    130                 135                 140
```

Val Arg Ala Leu Glu His Leu His Ser Lys Leu Ser Val Ile His Arg
145                 150                 155                 160

Asp Val Lys Pro Ser Asn Val Leu Ile Asn Lys Glu Gly His Val Lys
                165                 170                 175

Met Cys Asp Phe Gly Ile Ser Gly Tyr Leu Val Asp Ser Val Ala Lys
            180                 185                 190

Thr Met Asp Ala Gly Cys Lys Pro Tyr Met Ala Pro Glu Arg Ile Asn
        195                 200                 205

Pro Glu Leu Asn Gln Lys Gly Tyr Asn Val Lys Ser Asp Val Trp Ser
    210                 215                 220

Leu Gly Ile Thr Met Ile Glu Met Ala Ile Leu Arg Phe Pro Tyr Glu
225                 230                 235                 240

Ser Trp Gly Thr Pro Phe Gln Gln Leu Lys Gln Val Val Glu Glu Pro
                245                 250                 255

Ser Pro Gln Leu Pro Ala Asp Arg Phe Ser Pro Glu Phe Val Asp Phe
            260                 265                 270

Thr Ala Gln Cys Leu Arg Lys Asn Pro Ala Glu Arg Met Ser Tyr Leu
        275                 280                 285

Glu Leu Met Glu His Pro Phe Phe Thr Leu His Lys Thr Lys Lys Thr
    290                 295                 300

Asp Ile Ala Ala Phe Val Lys Lys Ile Leu Gly Glu Asp Ser
305                 310                 315

(2) INFORMATION FOR SEQ ID NO:3:

(i) SEQUENCE CHARACTERISTICS:
        (A) LENGTH: 1602 base pairs
        (B) TYPE: nucleic acid
        (C) STRANDEDNESS: single
        (D) TOPOLOGY: linear (xi) SEQUENCE DESCRIPTION: SEQ ID NO:3:

```
TAGCTGCAGC ACAGCCTTCC CTAACGTTGC AACTGGGGGA AAAATCACTT TCCAGTCTGT      60

TTTGCAAGGT GTGCATTTCC ATCTTGATTC CCTGAAAGTC CATCTGCTGC ATCGGTCAAG     120

AGAAACTCCA CTTGCATGAA GATTGCACGC CTGCAGCTTG CATCTTTGTT GCAAAACTAG     180

CTACAGAAGA GAAGCAAGGC AAAGTCTTTT GTGCTCCCCT CCCCCATCAA AGGAAAGGGG     240

AAAATGTCTC AGTCGAAAGG CAAGAAGCGA AACCCTGGCC TTAAAATTCC AAAAGAAGCA     300

TTTGAACAAC CTCAGACCAG TTCCACACCA CCTAGAGATT TAGACTCCAA GGCTTGCATT     360

TCTATTGGAA ATCAGAACTT TGAGGTGAAG GCAGATGACC TGGAGCCTAT AATGGAACTG     420

GGACGAGGTG CGTACGGGGT GGTGGAGAAG ATGCGGCACG TGCCCAGCGG GCAGATCATG     480

GCAGTGAAGC GGATCCGAGC CACAGTAAAT AGCCAGGAAC AGAAACGGCT ACTGATGGAT     540

TTGGATATTT CCATGAGGAC GGTGGACTGT CCATTCACTG TCACCTTTTA TGGCGCACTG     600

TTTCGGGAGG GTGATGTGTG GATCTGCATG GAGCTCATGG ATACATCACT AGATAAATTC     660

TACAAACAAG TTATTGATAA AGGCCAGACA ATTCCAGAGG ACATCTTAGG GAAAATAGCA     720

GTTTCTATTG TAAAAGCATT AGAACATTTA CATAGTAAGC TGTCTGTCAT TCACAGAGAC     780

GTCAAGCCTT CTAATGTACT CATCAATGCT CTCGGTCAAG TGAAGATGTG CGATTTTGGA     840

ATCAGTGGCT ACTTGGTGGA CTCTGTTGCT AAAACAATTG ATGCAGGTTG CAAACCATAC     900

ATGGCCCCTG AAAGAATAAA CCCAGAGCTC AACCAGAAGG GATACAGTGT GAAGTCTGAC     960

ATTTGGAGTC TGGGCATCAC GATGATTGAG TTGGCCATCC TTCGATTTCC CTATGATTCA    1020

TGGGGAACTC CATTTCAGCA GCTCAAACAG GTGGTAGAGG AGCCATCGCC ACAACTCCCA    1080
```

-continued

```
GCAGACAAGT TCTCTGCAGA GTTTGTTGAC TTTACCTCAC AGTGCTTAAA GAAGAATTCC    1140

AAAGAACGGC CTACATACCC AGAGCTAATG CAACATCCAT TTTTCACCCT ACATGAATCC    1200

AAAGGAACAG ATGTGGCATC TTTTGTAAAA CTGATTCTTG GAGACTAAAA AGCAGTGGAC    1260

TTAATCGGTT GACCCTACTG TGGATTGGTG GGTTTCGGGG TGAAGCAAGT TCACTACAGC    1320

ATCAATAGAA AGTCATCTTT GAGATAATTT AACCCTGCCT CTCAGAGGGT TTTCTCTCCC    1380

AATTTTCTTT TTACTCCCCC TCTTAAGGGG GCCTTGGAAT CTATAGTATA GAATGAACTG    1440

TCTAGATGGA TGAATTATGA TAAAGGCTTA GGACTTCAAA AGGTGATTAA ATATTTAATG    1500

ATGTGTCATA TGAGTCCTCA AAAAAAAAAA AAAAAAAAAA AAAAAAAAAA AAAAAAAAAA    1560

AAAAAAAAAA AAAAAAAAAA AAAAAAAAAA AAAAAAAAAA AA                      1602
```

(2) INFORMATION FOR SEQ ID NO:4:

(i) SEQUENCE CHARACTERISTICS:
        (A) LENGTH: 334 amino acids
        (B) TYPE: amino acid
        (C) STRANDEDNESS: Not Relevant
        (D) TOPOLOGY: linear (xi) SEQUENCE DESCRIPTION: SEQ ID NO:4:

```
Met Ser Gln Ser Lys Gly Lys Lys Arg Asn Pro Gly Leu Lys Ile Pro
1               5                   10                  15

Lys Glu Ala Phe Glu Gln Pro Gln Thr Ser Ser Thr Pro Pro Arg Asp
            20                  25                  30

Leu Asp Ser Lys Ala Cys Ile Ser Ile Gly Asn Gln Asn Phe Glu Val
        35                  40                  45

Lys Ala Asp Asp Leu Glu Pro Ile Met Glu Leu Gly Arg Gly Ala Tyr
    50                  55                  60

Gly Val Val Glu Lys Met Arg His Val Pro Ser Gly Gln Ile Met Ala
65                  70                  75                  80

Val Lys Arg Ile Arg Ala Thr Val Asn Ser Gln Glu Gln Lys Arg Leu
                85                  90                  95

Leu Met Asp Leu Asp Ile Ser Met Arg Thr Val Asp Cys Pro Phe Thr
            100                 105                 110

Val Thr Phe Tyr Gly Ala Leu Phe Arg Glu Gly Asp Val Trp Ile Cys
        115                 120                 125

Met Glu Leu Met Asp Thr Ser Leu Asp Lys Phe Tyr Lys Gln Val Ile
    130                 135                 140

Asp Lys Gly Gln Thr Ile Pro Glu Asp Ile Leu Gly Lys Ile Ala Val
145                 150                 155                 160

Ser Ile Val Lys Ala Leu Glu His Leu His Ser Lys Leu Ser Val Ile
                165                 170                 175

His Arg Asp Val Lys Pro Ser Asn Val Leu Ile Asn Ala Leu Gly Gln
            180                 185                 190

Val Lys Met Cys Asp Phe Gly Ile Ser Gly Tyr Leu Val Asp Ser Val
        195                 200                 205

Ala Lys Thr Ile Asp Ala Gly Cys Lys Pro Tyr Met Ala Pro Glu Arg
    210                 215                 220

Ile Asn Pro Glu Leu Asn Gln Lys Gly Tyr Ser Val Lys Ser Asp Ile
225                 230                 235                 240

Trp Ser Leu Gly Ile Thr Met Ile Glu Leu Ala Ile Leu Arg Phe Pro
                245                 250                 255

Tyr Asp Ser Trp Gly Thr Pro Phe Gln Gln Leu Lys Gln Val Val Glu
```

```
                260                265                270
Glu Pro Ser Pro Gln Leu Pro Ala Asp Lys Phe Ser Ala Glu Phe Val
            275                280                285

Asp Phe Thr Ser Gln Cys Leu Lys Lys Asn Ser Lys Glu Arg Pro Thr
        290                295                300

Tyr Pro Glu Leu Met Gln His Pro Phe Phe Thr Leu His Glu Ser Lys
305                310                315                320

Gly Thr Asp Val Ala Ser Phe Val Lys Leu Ile Leu Gly Asp
                325                330
```

(2) INFORMATION FOR SEQ ID NO:5:

(i) SEQUENCE CHARACTERISTICS:
        (A) LENGTH: 3497 base pairs
        (B) TYPE: nucleic acid
        (C) STRANDEDNESS: single
        (D) TOPOLOGY: linear (xi) SEQUENCE DESCRIPTION: SEQ ID NO:5:

```
CTAGGGTCCC CGGCGCCAGG CCACCCGGCC GTCAGCAGCA TGCAGGGTAA ACGCAAAGCA    60

CTGAAGTTGA ATTTTGCAAA TCCACCTTTC AAATCTACAG CAAGGTTTAC TCTGAATCCC   120

AATCCTACAG GAGTTCAAAA CCCACACATA GAGAGACTGA GAACACACAG CATTGAGTCA   180

TCAGGAAAAC TGAAGATCTC CCCTGAACAA CACTGGGATT TCACTGCAGA GGACTTGAAA   240

GACCTTGGAG AAATTGGACG AGGAGCTTAT GGTTCTGTCA ACAAAATGGT CCACAAACCA   300

AGTGGGCAAA TAATGGCAGT TAAAAGAATT CGGTCAACAG TGGATGAAAA AGAACAAAAA   360

CAACTTCTTA TGGATTTGGA TGTAGTAATG CGGAGTAGTG ATTGCCCATA CATTGTTCAG   420

TTTTATGGTG CACTCTTCAG AGAGGGTGAC TGTTGGATCT GTATGGAACT CATGTCTACC   480

TCGTTTGATA AGTTTTACAA ATATGTATAT AGTGTATTAG ATGATGTTAT TCCAGAAGAA   540

ATTTTAGGCA AAATCACTTT AGCAACTGTG AAAGCACTAA ACCACTTAAA AGAAAACTTG   600

AAAATTATTC ACAGAGATAT CAAACCTTCC AATATTCTTC TGGACAGAAG TGGAAATATT   660

AAGCTCTGTG ACTTCGGCAT CAGTGGACAG CTTGTGGACT CTATTGCCAA GACAAGAGAT   720

GCTGGCTGTA GGCCATACAT GGCACCTGAA AGAATAGACC CAAGCGCATC ACGACAAGGA   780

TATGATGTCC GCTCTGATGT CTGGAGTTTG GGGATCACAT TGTATGAGTT GGCCACAGGC   840

CGATTTCCTT ATCCAAAGTG GAATAGTGTA TTTGATCAAC TAACACAAGT CGTGAAAGGA   900

GATCCTCCGC AGCTGAGTAA TTCTGAGGAA AGGGAATTCT CCCCGAGTTT CATCAACTTT   960

GTCAACTTGT GCCTTACGAA GGATGAATCC AAAAGGCCAA AGTATAAAGA GCTTCTGAAA  1020

CATCCCTTTA TTTTGATGTA TGAAGAACGT GCCGTTGAGG TCGCATGCTA TGTTTGTAAA  1080

ATCCTGGATC AAATGCCAGC TACTCCCAGC TCTCCCATGT ATGTCGATTG ATATCGTGCT  1140

ACATCAGACT CTAGAAAAAA GGGCTGAGAG GAAGCAAGAC GTAAAGAATT TTCATCCCGT  1200

ATCACAGTGT TTTTATTGCT CGCCCAGACA CCATGTGCAA TAAGATTGGT GTTCGTTTCC  1260

ATCATGTCTG TATACTCCTG TCACCTAGAA CGTGCATCCT TGTAATACCT GATTGATCAC  1320

ACAGTGTTAG TGCTGGTCAG AGAGACCTCA TCCTGCTCTT TTGTGATGAA CATATTCATG  1380

AAATGTGGAA GTCAGTACGA TCAAGTTGTT GACTGTGATT AGATCACATC TTAAATTCAT  1440

TTCTAGACTC AAAACCTGGA GATGCAGCTA CTGGAATGGT GTTTTGTCAG ACTTCCAAAT  1500

CCTGGAAGGA CACAGTGATG AATGTACTAT ATCTGAACAT AGAAACTCGG GCTTGAGTGA  1560

GAAGAGCTTG CACAGCCAAC GAGACACATT GCCTTCTGGA GCTGGGAGAC AAAGGAGGAA  1620
```

-continued

```
TTTACTTTCT TCACCAAGTG CAATAGATTA CTGATGTGAT ATTCTGTTGC TTTACAGTTA    1680

CAGTTGATGT TTGGGGATCG ATGTGCTCAG CCAAATTTCC TGTTTGAAAT ATCATGTTAA    1740

ATTAGAATGA ATTTATCTTT ACCAAAAACC ATGTTGCGTT CAAAGAGGTG AACATTAAAA    1800

TATAGAGACA GGACAGAATG TGTTCTTTTC TCCTCTACCA GTCCTATTTT TCAATGGGAA    1860

GACTCAGGAG TCTGCCACTT GTCAAAGAAG GTGCTGATCC TAAGAATTTT TCATTCTCAG    1920

AATTCGGTGT GCTGCCAACT TGATGTTCCA CCTGCCACAA ACCACCAGGA CTGAAAGAAG    1980

AAAACAGTAC AGAAGGCAAA GTTTACAGAT GTTTTTAATT CTAGTATTTT ATCTGGAACA    2040

ACTTGTAGCA GCTATATATT TCCCCTTGGT CCCAAGCCTG ATACTTTAGC CATCATAACT    2100

CACTAACAGG GAGAAGTAGC TAGTAGCAAT GTGCCTTGAT TGATTAGATA AAGATTTCTA    2160

GTAGGCAGCA AAAGACCAAA TCTCAGTTGT TTGCTTCTTG CCATCACTGG TCCAGGTCTT    2220

CAGTTTCCGA ATCTCTTTCC CTTCCCCTGT GGTCTATTGT CGCTATGTGA CTTGCGCTTA    2280

ATCCAATATT TTGCCTTTTT TCTATATCAA AAAACCTTTA CAGTTAGCAG GGATGTTCCT    2340

TACCGAGGAT TTTTAACCCC CAATCTCTCA TAATCGCTAG TGTTTAAAAG GCTAAGAATA    2400

GTGGGGCCCA ACCGATGTGG TAGGTGATAA AGAGGCATCT TTTCTAGAGA CACATTGGAC    2460

CAGATGAGGA TCCGAAACGG CAGCCTTTAC GTTCATCACC TGCTAGAACC TCTCGTAGTC    2520

CATCACCATT TCTTGGCATT GGAATTCTAC TGGAAAAAAA TACAAAAGC AAAACAAAAC    2580

CCTCAGCACT GTTACAAGAG GCCATTTAAG TATCTTGTGC TTCTTCACTT ACCCATTAGC    2640

CAGGTTCTCA TTAGGTTTTG CTTGGGCCTC CCTGGCACTG AACCTTAGGC TTTGTATGAC    2700

AGTGAAGCAG CACTGTGAGT GGTTCAAGCA CACTGGAATA TAAAACAGTC ATGGCCTGAG    2760

ATGCAGGTGA TGCCATTACA GAACCAAATC GTGGCACGTA TTGCTGTGTC TCCTCTCAGA    2820

GTGACAGTCA TAAATACTGT CAAACAATAA AGGGAGAATG GTGCTGTTTA AAGTCACATC    2880

CCTGTAAATT GCAGAATTCA AAAGTGATTA TCTCTTTGAT CTACTTGCCT CATTTCCCTA    2940

TCTTCTCCCC CACGGTATCC TAAACTTTAG ACTTCCCACT GTTCTGAAAG GAGACATTGC    3000

TCTATGTCTG CCTTCGACCA CAGCAAGCCA TCATCCTCCA TTGCTCCCGG GGACTCAAGA    3060

GGAATCTGTT TCTCTGCTGT CAACTTCCCA TCTGGCTCAG CATAGGGTCA CTTTGCCATT    3120

ATGCAAATGG AGATAAAAGC AATTCTGGCT GTCCAGGAGC TAATCTGACC GTTCTATTGT    3180

GTGGATGACC ACATAAGAAG GCAATTTTAG TGTATTAATC ATAGATTATT ATAAACTATA    3240

AACTTAAGGG CAAGGAGTTT ATTACAATGT ATCTTTATTA AAACAAAAGG GTGTATAGTG    3300

TTCACAAACT GTGAAAATAG TGTAAGAACT GTACATTGTG AGCTCTGGTT ATTTTTCTCT    3360

TGTACCATAG AAAAATGTAT AAAAATTATC AAAAAGCTAA TGTGCAGGGA TATTGCCTTA    3420

TTTGTCTGTA AAAAATGGAG CTCAGTAACA TAACTGCTTC TTGGAGCTTT GGAATATTTT    3480

ATCCTGTATT CTTGTTT                                                    3497
```

(2) INFORMATION FOR SEQ ID NO:6:

(i) SEQUENCE CHARACTERISTICS:
        (A) LENGTH: 363 amino acids
        (B) TYPE: amino acid
        (C) STRANDEDNESS: Not Relevant
        (D) TOPOLOGY: linear (xi) SEQUENCE DESCRIPTION: SEQ ID NO:6:

```
Met Gln Gly Lys Arg Lys Ala Leu Lys Leu Asn Phe Ala Asn Pro Pro
1               5                   10                  15

Phe Lys Ser Thr Ala Arg Phe Thr Leu Asn Pro Asn Pro Thr Gly Val
```

|  | | 20 | | | | 25 | | | | 30 | | |
|---|---|---|---|---|---|---|---|---|---|---|---|---|

Gln Asn Pro His Ile Glu Arg Leu Arg Thr His Ser Ile Glu Ser Ser
          35                      40                  45

Gly Lys Leu Lys Ile Ser Pro Glu Gln His Trp Asp Phe Thr Ala Glu
 50                      55                  60

Asp Leu Lys Asp Leu Gly Glu Ile Gly Arg Gly Ala Tyr Gly Ser Val
 65                  70                  75                  80

Asn Lys Met Val His Lys Pro Ser Gly Gln Ile Met Ala Val Lys Arg
              85                  90                  95

Ile Arg Ser Thr Val Asp Glu Lys Glu Gln Lys Gln Leu Leu Met Asp
          100                     105                 110

Leu Asp Val Val Met Arg Ser Ser Asp Cys Pro Tyr Ile Val Gln Phe
      115                     120                 125

Tyr Gly Ala Leu Phe Arg Glu Gly Asp Cys Trp Ile Cys Met Glu Leu
 130                     135                 140

Met Ser Thr Ser Phe Asp Lys Phe Tyr Lys Tyr Val Tyr Ser Val Leu
145                     150                 155                 160

Asp Asp Val Ile Pro Glu Glu Ile Leu Gly Lys Ile Thr Leu Ala Thr
              165                 170                 175

Val Lys Ala Leu Asn His Leu Lys Glu Asn Leu Lys Ile Ile His Arg
          180                 185                 190

Asp Ile Lys Pro Ser Asn Ile Leu Leu Asp Arg Ser Gly Asn Ile Lys
          195                 200                 205

Leu Cys Asp Phe Gly Ile Ser Gly Gln Leu Val Asp Ser Ile Ala Lys
      210                 215                 220

Thr Arg Asp Ala Gly Cys Arg Pro Tyr Met Ala Pro Glu Arg Ile Asp
225                 230                 235                 240

Pro Ser Ala Ser Arg Gln Gly Tyr Asp Val Arg Ser Asp Val Trp Ser
              245                 250                 255

Leu Gly Ile Thr Leu Tyr Glu Leu Ala Thr Gly Arg Phe Pro Tyr Pro
          260                 265                 270

Lys Trp Asn Ser Val Phe Asp Gln Leu Thr Gln Val Val Lys Gly Asp
      275                 280                 285

Pro Pro Gln Leu Ser Asn Ser Glu Glu Arg Glu Phe Ser Pro Ser Phe
 290                 295                 300

Ile Asn Phe Val Asn Leu Cys Leu Thr Lys Asp Glu Ser Lys Arg Pro
305                 310                 315                 320

Lys Tyr Lys Glu Leu Leu Lys His Pro Phe Ile Leu Met Tyr Glu Glu
              325                 330                 335

Arg Ala Val Glu Val Ala Cys Tyr Val Cys Lys Ile Leu Asp Gln Met
          340                 345                 350

Pro Ala Thr Pro Ser Ser Pro Met Tyr Val Asp
      355                 360

(2) INFORMATION FOR SEQ ID NO:7:

(i) SEQUENCE CHARACTERISTICS:
        (A) LENGTH: 3553 base pairs
        (B) TYPE: nucleic acid
        (C) STRANDEDNESS: single
        (D) TOPOLOGY: linear (xi) SEQUENCE DESCRIPTION: SEQ ID NO:7:

CAACAATGGC GGCTCCGAGC CCGAGCGGTG GCGGCGGCAG CGGCACCCCC GGCCCCGTAG    60

GGTCCCCGGC GCCAGGCCAC CCGGCCGTCA GCAGCATGCA GGGTAAACGC AAAGCACTGA   120

-continued

```
AGTTGAATTT TGCAAATCCA CCTTTCAAAT CTACAGCAAG GTTTACTCTG AATCCCAATC      180

CTACAGGAGT TCAAAACCCA CACATAGAGA GACTGAGAAC ACACAGCATT GAGTCATCAG      240

GAAAACTGAA GATCTCCCCT GAACAACACT GGGATTTCAC TGCAGAGGAC TTGAAAGACC     300

TTGGAGAAAT TGGACGAGGA GCTTATGGTT CTGTCAACAA AATGGTCCAC AAACCAAGTG     360

GGCAAATAAT GGCAGTTAAA AGAATTCGGT CAACAGTGGA TGAAAAGAA CAAAAACAAC      420

TTCTTATGGA TTTGGATGTA GTAATGCGGA GTAGTGATTG CCCATACATT GTTCAGTTTT     480

ATGGTGCACT CTTCAGAGAG GGTGACTGTT GGATCTGTAT GGAACTCATG TCTACCTCGT     540

TTGATAAGTT TTACAAATAT GTATATAGTG TATTAGATGA TGTTATTCCA GAAGAAATTT     600

TAGGCAAAAT CACTTTAGCA ACTGTGAAAG CACTAAACCA CTTAAAAGAA AACTTGAAAA     660

TTATTCACAG AGATATCAAA CCTTCCAATA TTCTTCTGGA CAGAAGTGGA ATATATTAAGC    720

TCTGTGACTT CGGCATCAGT GGACAGCTTG TGGACTCTAT TGCCAAGACA AGAGATGCTG    780

GCTGTAGGCC ATACATGGCA CCTGAAAGAA TAGACCCAAG CGCATCACGA CAAGGATATG    840

ATGTCCGCTC TGATGTCTGG AGTTTGGGGA TCACATTGTA TGAGTTGGCC ACAGGCCGAT    900

TTCCTTATCC AAAGTGGAAT AGTGTATTTG ATCAACTAAC ACAAGTCGTG AAAGGAGATC    960

CTCCGCAGCT GAGTAATTCT GAGGAAAGGG AATTCTCCCC GAGTTTCATC AACTTTGTCA   1020

ACTTGTGCCT TACGAAGGAT GAATCCAAAA GGCCAAAGTA TAAAGAGCTT CTGAAACATC   1080

CCTTTATTTT GATGTATGAA GAACGTGCCG TTGAGGTCGC ATGCTATGTT TGTAAAATCC   1140

TGGATCAAAT GCCAGCTACT CCCAGCTCTC CCATGTATGT CGATTGATAT CGTGCTACAT   1200

CAGACTCTAG AAAAAAGGGC TGAGAGGAAG CAAGACGTAA AGAATTTTCA TCCCGTATCA   1260

CAGTGTTTTT ATTGCTCGCC CAGACACCAT GTGCAATAAG ATTGGTGTTC GTTTCCATCA   1320

TGTCTGTATA CTCCTGTCAC CTAGAACGTG CATCCTTGTA ATACCTGATT GATCACACAG   1380

TGTTAGTGCT GGTCAGAGAG ACCTCATCCT GCTCTTTTGT GATGAACATA TTCATGAAAT   1440

GTGGAAGTCA GTACGATCAA GTTGTTGACT GTGATTAGAT CACATCTTAA ATTCATTTCT   1500

AGACTCAAAA CCTGGAGATG CAGCTACTGG AATGGTGTTT TGTCAGACTT CCAAATCCTG   1560

GAAGGACACA GTGATGAATG TACTATATCT GAACATAGAA ACTCGGGCTT GAGTGAGAAG   1620

AGCTTGCACA GCCAACGAGA CACATTGCCT TCTGGAGCTG GGAGACAAAG GAGGAATTTA   1680

CTTTCTTCAC CAAGTGCAAT AGATTACTGA TGTGATATTC TGTTGCTTTA CAGTTACAGT   1740

TGATGTTTGG GGATCGATGT GCTCAGCCAA ATTTCCTGTT TGAAATATCA TGTTAAATTA   1800

GAATGAATTT ATCTTTACCA AAAACCATGT TGCGTTCAAA GAGGTGAACA TTAAAATATA   1860

GAGACAGGAC AGAATGTGTT CTTTTCTCCT CTACCAGTCC TATTTTTCAA TGGGAAGACT   1920

CAGGAGTCTG CCACTTGTCA AGAAGGTGC TGATCCTAAG AATTTTTCAT TCTCAGAATT    1980

CGGTGTGCTG CCAACTTGAT GTTCCACCTG CCACAAACCA CCAGGACTGA AGAAGAAAA    2040

CAGTACAGAA GGCAAAGTTT ACAGATGTTT TTAATTCTAG TATTTTATCT GGAACAACTT   2100

GTAGCAGCTA TATATTTCCC CTTGGTCCCA AGCCTGATAC TTTAGCCATC ATAACTCACT   2160

AACAGGGAGA AGTAGCTAGT AGCAATGTGC CTTGATTGAT TAGATAAAGA TTTCTAGTAG   2220

GCAGCAAAAG ACCAAATCTC AGTTGTTTGC TTCTTGCCAT CACTGGTCCA GGTCTTCAGT   2280

TTCCGAATCT CTTTCCCTTC CCCTGTGGTC TATTGTCGCT ATGTGACTTG CGCTTAATCC   2340

AATATTTTGC CTTTTTTCTA TATCAAAAAA CCTTTACAGT TAGCAGGGAT GTTCCTTACC   2400

GAGGATTTTT AACCCCCAAT CTCTCATAAT CGCTAGTGTT TAAAAGGCTA AGAATAGTGG   2460
```

```
GGCCCAACCG ATGTGGTAGG TGATAAAGAG GCATCTTTTC TAGAGACACA TTGGACCAGA      2520

TGAGGATCCG AAACGGCAGC CTTTACGTTC ATCACCTGCT AGAACCTCTC GTAGTCCATC      2580

ACCATTTCTT GGCATTGGAA TTCTACTGGA AAAAAATACA AAAAGCAAAA CAAAACCCTC      2640

AGCACTGTTA CAAGAGGCCA TTTAAGTATC TTGTGCTTCT TCACTTACCC ATTAGCCAGG      2700

TTCTCATTAG GTTTTGCTTG GGCCTCCCTG GCACTGAACC TTAGGCTTTG TATGACAGTG      2760

AAGCAGCACT GTGAGTGGTT CAAGCACACT GGAATATAAA ACAGTCATGG CCTGAGATGC      2820

AGGTGATGCC ATTACAGAAC CAAATCGTGG CACGTATTGC TGTGTCTCCT CTCAGAGTGA      2880

CAGTCATAAA TACTGTCAAA CAATAAAGGG AGAATGGTGC TGTTTAAAGT CACATCCCTG      2940

TAAATTGCAG AATTCAAAAG TGATTATCTC TTTGATCTAC TTGCCTCATT TCCCTATCTT      3000

CTCCCCCACG GTATCCTAAA CTTTAGACTT CCCACTGTTC TGAAAGGAGA CATTGCTCTA      3060

TGTCTGCCTT CGACCACAGC AAGCCATCAT CCTCCATTGC TCCCGGGGAC TCAAGAGGAA      3120

TCTGTTTCTC TGCTGTCAAC TTCCCATCTG GCTCAGCATA GGGTCACTTT GCCATTATGC      3180

AAATGGAGAT AAAAGCAATT CTGGCTGTCC AGGAGCTAAT CTGACCGTTC TATTGTGTGG      3240

ATGACCACAT AAGAAGGCAA TTTTAGTGTA TTAATCATAG ATTATTATAA ACTATAAACT      3300

TAAGGGCAAG GAGTTTATTA CAATGTATCT TTATTAAAAC AAAAGGGTGT ATAGTGTTCA      3360

CAAACTGTGA AAATAGTGTA AGAACTGTAC ATTGTGAGCT CTGGTTATTT TTCTCTTGTA      3420

CCATAGAAAA ATGTATAAAA ATTATCAAAA AGCTAATGTG CAGGGATATT GCCTTATTTG      3480

TCTGTAAAAA ATGGAGCTCA GTAACATAAC TGCTTCTTGG AGCTTTGGAA TATTTTATCC      3540

TGTATTCTTG TTT                                                         3553
```

(2) INFORMATION FOR SEQ ID NO:8:

(i) SEQUENCE CHARACTERISTICS:
        (A) LENGTH: 393 amino acids
        (B) TYPE: amino acid
        (C) STRANDEDNESS: Not Relevant
        (D) TOPOLOGY: linear (xi) SEQUENCE DESCRIPTION: SEQ ID NO:8:

```
Met Ala Ala Pro Ser Pro Ser Gly Gly Gly Gly Ser Gly Thr Pro Gly
 1               5                  10                  15

Pro Val Gly Ser Pro Ala Pro Gly His Pro Ala Val Ser Ser Met Gln
             20                  25                  30

Gly Lys Arg Lys Ala Leu Lys Leu Asn Phe Ala Asn Pro Pro Phe Lys
         35                  40                  45

Ser Thr Ala Arg Phe Thr Leu Asn Pro Asn Pro Thr Gly Val Gln Asn
     50                  55                  60

Pro His Ile Glu Arg Leu Arg Thr His Ser Ile Glu Ser Ser Gly Lys
65                  70                  75                  80

Leu Lys Ile Ser Pro Glu Gln His Trp Asp Phe Thr Ala Glu Asp Leu
                 85                  90                  95

Lys Asp Leu Gly Glu Ile Gly Arg Gly Ala Tyr Gly Ser Val Asn Lys
            100                 105                 110

Met Val His Lys Pro Ser Gly Gln Ile Met Ala Val Lys Arg Ile Arg
        115                 120                 125

Ser Thr Val Asp Glu Lys Glu Gln Lys Gln Leu Leu Met Asp Leu Asp
    130                 135                 140

Val Val Met Arg Ser Ser Asp Cys Pro Tyr Ile Val Gln Phe Tyr Gly
145                 150                 155                 160
```

```
Ala Leu Phe Arg Glu Gly Asp Cys Trp Ile Cys Met Glu Leu Met Ser
            165                 170                 175

Thr Ser Phe Asp Lys Phe Tyr Lys Tyr Val Tyr Ser Val Leu Asp Asp
            180                 185                 190

Val Ile Pro Glu Glu Ile Leu Gly Lys Ile Thr Leu Ala Thr Val Lys
            195                 200                 205

Ala Leu Met His Leu Lys Glu Asn Leu Lys Ile Ile His Arg Asp Ile
            210                 215                 220

Lys Pro Ser Asn Ile Leu Leu Asp Arg Ser Gly Met Ile Lys Leu Cys
225                 230                 235                 240

Asp Phe Gly Ile Ser Gly Gln Leu Val Asp Ser Ile Ala Lys Thr Arg
            245                 250                 255

Asp Ala Gly Cys Arg Pro Tyr Met Ala Pro Glu Arg Ile Asp Phe Ser
            260                 265                 270

Ala Ser Arg Gln Gly Tyr Asp Val Arg Ser Asp Val Trp Ser Leu Gly
            275                 280                 285

Ile Thr Leu Tyr Glu Leu Ala Thr Gly Arg Phe Pro Tyr Pro Lys Trp
            290                 295                 300

Asn Ser Val Phe Asp Gln Leu Thr Gln Val Val Lys Gly Asp Pro Pro
305                 310                 315                 320

Gln Leu Ser Asn Ser Glu Glu Arg Glu Phe Ser Pro Ser Phe Ile Asn
            325                 330                 335

Phe Val Asn Leu Cys Leu Thr Lys Asp Glu Ser Lys Arg Pro Lys Tyr
            340                 345                 350

Lys Glu Leu Leu Lys His Pro Phe Ile Leu Met Tyr Glu Glu Arg Ala
            355                 360                 365

Val Glu Val Ala Cys Tyr Val Cys Lys Ile Leu Asp Gln Met Pro Ala
            370                 375                 380

Thr Pro Ser Ser Pro Met Tyr Val Asp
385                 390
```

(2) INFORMATION FOR SEQ ID NO:9:

(i) SEQUENCE CHARACTERISTICS:
        (A) LENGTH: 3576 base pairs
        (B) TYPE: nucleic acid
        (C) STRANDEDNESS: single
        (D) TOPOLOGY: linear (xi) SEQUENCE DESCRIPTION: SEQ ID NO:9:

```
CTCCCAACAA TGGCGGCTCC GAGCCCGAGC GGCGGCGGCG GCTCCGGGGG CGGCAGCGGC      60

AGCGGCACCC CCGGCCCCGT AGGGTCCCCG GCGCCAGGCC ACCCGGCCGT CAGCAGCATG     120

CAGGGTAAAC GCAAAGCACT GAAGTTGAAT TTTGCAAATC CACCTTTCAA ATCTACAGCA     180

AGGTTTACTC TGAATCCCAA TCCTACAGGA GTTCAAAACC CACACATAGA GAGACTGAGA     240

ACACACAGCA TTGAGTCATC AGGAAAACTG AAGATCTCCC CTGAACAACA CTGGGATTTC     300

ACTGCAGAGG ACTTGAAAGA CCTTGGAGAA ATTGGACGAG GAGCTTATGG TTCTGTCAAC     360

AAAATGGTCC ACAAACCAAG TGGGCAAATA ATGGCAGTTA AAAGAATTCG GTCAACAGTG     420

GATGAAAAAG AACAAAAACA ACTTCTTATG GATTTGGATG TAGTAATGCG GAGTAGTGAT     480

TGCCCATACA TTGTTCAGTT TTATGGTGCA CTCTTCAGAG AGGGTGACTG TTGGATCTGT     540

ATGGAACTCA TGTCTACCTC GTTTGATAAG TTTTACAAAT ATGTATATAG TGTATTAGAT     600

GATGTTATTC CAGAAGAAAT TTTAGGCAAA ATCACTTTAG CAACTGTGAA AGCACTAAAC     660

CACTTAAAAG AAAACTTGAA AATTATTCAC AGAGATATCA AACCTTCCAA TATTCTTCTG     720
```

```
GACAGAAGTG GAAATATTAA GCTCTGTGAC TTCGGCATCA GTGGACAGCT TGTGGACTCT      780
ATTGCCAAGA CAAGAGATGC TGGCTGTAGG CCATACATGG CACCTGAAAG AATAGACCCA      840
AGCGCATCAC GACAAGGATA TGATGTCCGC TCTGATGTCT GGAGTTTGGG GATCACATTG      900
TATGAGTTGG CCACAGGCCG ATTTCCTTAT CCAAAGTGGA ATAGTGTATT TGATCAACTA      960
ACACAAGTCG TGAAAGGAGA TCCTCCGCAG CTGAGTAATT CTGAGGAAAG GGAATTCTCC     1020
CCGAGTTTCA TCAACTTTGT CAACTTGTGC CTTACGAAGG ATGAATCCAA AAGGCCAAAG     1080
TATAAAGAGC TTCTGAAACA TCCCTTTATT TTGATGTATG AAGAACGTGC CGTTGAGGTC     1140
GCATGCTATG TTTGTAAAAT CCTGGATCAA ATGCCAGCTA CTCCCAGCTC TCCCATGTAT     1200
GTCGATTGAT ATCGCTGCTA CATCAGACTC TAGAAAAAAG GGCTGAGAGG AAGCAAGACG     1260
TAAAGAATTT TCATCCCGTA TCACAGTGTT TTTATTGCTC GCCCAGACAC CATGTGCAAT     1320
AAGATTGGTG TTCGTTTCCA TCATGTCTGT ATACTCCTGT CACCTAGAAC GTGCATCCTT     1380
GTAATACCTG ATTGATCACA CAGTGTTAGT GCTGGTCAGA GAGACCTCAT CCTGCTCTTT     1440
TGTGATGAAC ATATTCATGA AATGTGGAAG TCAGTACGAT CAAGTTGTTG ACTGTGATTA     1500
GATCACATCT TAAATTCATT TCTAGACTCA AAACCTGGAG ATGCAGCTAC TGGAATGGTG     1560
TTTTGTCAGA CTTCCAAATC CTGGAAGGAC ACAGTGATGA ATGTACTATA TCTGAACATA     1620
GAAACTCGGG CTTGAGTGAG AAGAGCTTGC ACAGCCAACG AGACACATTG CCTTCTGGAG     1680
CTGGGAGACA AAGGAGGAAT TTACTTTCTT CACCAAGTGC AATAGATTAC TGATGTGATA     1740
TTCTGTTGCT TTACAGTTAC AGTTGATGTT TGGGGATCGA TGTGCTCAGC CAAATTTCCT     1800
GTTTGAAATA TCATGTTAAA TTAGAATGAA TTTATCTTTA CCAAAAACCA TGTTGCGTTC     1860
AAAGAGGTGA ACATTAAAAT ATAGAGACAG GACAGAATGT GTTCTTTTCT CCTCTACCAG     1920
TCCTATTTTT CAATGGGAAG ACTCAGGAGT CTGCCACTTG TCAAAGAAGG TGCTGATCCT     1980
AAGAATTTTT CATTCTCAGA ATTCGGTGTG CTGCCAACTT GATGTTCCAC CTGCCACAAA     2040
CCACCAGGAC TGAAAGAAGA AAACAGTACA GAAGGCAAAG TTTACAGATG TTTTTAATTC     2100
TAGTATTTTA TCTGGAACAA CTTGTAGCAG CTATATATTT CCCCTTGGTC CCAAGCCTGA     2160
TACTTTAGCC ATCATAACTC ACTAACAGGG AGAAGTAGCT AGTAGCAATG TGCCTTGATT     2220
GATTAGATAA AGATTTCTAG TAGGCAGCAA AAGACCAAAT CTCAGTTGTT TGCTTCTTGC     2280
CATCACTGGT CCAGGTCTTC AGTTTCCGAA TCTCTTTCCC TTCCCCTGTG GTCTATTGTC     2340
GCTATGTGAC TTGCGCTTAA TCCAATATTT TGCCTTTTTT CTATATCAAA AAACCTTTAC     2400
AGTTAGCAGG GATGTTCCTT ACCGAGGATT TTTAACCCCC AATCTCTCAT AATCGCTAGT     2460
GTTTAAAAGG CTAAGAATAG TGGGGCCCAA CCGATGTGGT AGGTGATAAA GAGGCATCTT     2520
TTCTAGAGAC ACATTGGACC AGATGAGGAT CCGAAACGGC AGCCTTTACG TTCATCACCT     2580
GCTAGAACCT CTCGTAGTCC ATCACCATTT CTTGGCATTG GAATTCTACT GGAAAAAAAT     2640
ACAAAAGCA AAACAAAACC CTCAGCACTG TTACAAGAGG CCATTTAAGT ATCTTGTGCT      2700
TCTTCACTTA CCCATTAGCC AGGTTCTCAT TAGGTTTTGC TTGGGCCTCC CTGGCACTGA     2760
ACCTTAGGCT TTGTATGACA GTGAAGCAGC ACTGTGAGTG GTTCAAGCAC ACTGGAATAT     2820
AAAACAGTCA TGGCCTGAGA TGCAGGTGAT GCCATTACAG AACCAAATCG TGGCACGTAT     2880
TGCTGTGTCT CCTCTCAGAG TGACAGTCAT AAATACTGTC AAACAATAAA GGGAGAATGG     2940
TGCTGTTTAA AGTCACATCC CTGTAAATTG CAGAATTCAA AAGTGATTAT CTCTTTGATC     3000
TACTTGCCTC ATTTCCCTAT CTTCTCCCCC ACGGTATCCT AAACTTTAGA CTTCCCACTG     3060
```

```
TTCTGAAAGG AGACATTGCT CTATGTCTGC CTTCGACCAC AGCAAGCCAT CATCCTCCAT    3120

TGCTCCCGGG GACTCAAGAG GAATCTGTTT CTCTGCTGTC AACTTCCCAT CTGGCTCAGC    3180

ATAGGGTCAC TTTGCCATTA TGCAAATGGA GATAAAAGCA ATTCTGGCTG TCCAGGAGCT    3240

AATCTGACCG TTCTATTGTG TGGATGACCA CATAAGAAGG CAATTTTAGT GTATTAATCA    3300

TAGATTATTA TAAACTATAA ACTTAAGGGC AAGGAGTTTA TTACAATGTA TCTTTATTAA    3360

AACAAAAGGG TGTATAGTGT TCACAAACTG TGAAAATAGT GTAAGAACTG TACATTGTGA    3420

GCTCTGGTTA TTTTTCTCTT GTACCATAGA AAAATGTATA AAAATTATCA AAAGCTAAT     3480

GTGCAGGGAT ATTGCCTTAT TTGTCTGTAA AAAATGGAGC TCAGTAACAT AACTGCTTCT    3540

TGGAGCTTTG GAATATTTTA TCCTGTATTC TTGTTT                              3576
```

(2) INFORMATION FOR SEQ ID NO:10:

(i) SEQUENCE CHARACTERISTICS:
        (A) LENGTH: 399 amino acids
        (B) TYPE: amino acid
        (C) STRANDEDNESS: Not Relevant
        (D) TOPOLOGY: linear (xi) SEQUENCE DESCRIPTION: SEQ ID NO:10:

```
Met Ala Ala Pro Ser Pro Ser Gly Gly Gly Gly Ser Gly Gly Gly Ser
1               5                   10                  15

Gly Ser Gly Thr Pro Gly Pro Val Gly Ser Pro Ala Pro Gly His Pro
            20                  25                  30

Ala Val Ser Ser Met Gln Gly Lys Arg Lys Ala Leu Lys Leu Asn Phe
        35                  40                  45

Ala Asn Pro Pro Phe Lys Ser Thr Ala Arg Phe Thr Leu Asn Pro Asn
    50                  55                  60

Pro Thr Gly Val Gln Asn Pro His Ile Glu Arg Leu Arg Thr His Ser
65                  70                  75                  80

Ile Glu Ser Ser Gly Lys Leu Lys Ile Ser Pro Glu Gln His Trp Asp
                85                  90                  95

Phe Thr Ala Glu Asp Leu Lys Asp Leu Gly Glu Ile Gly Arg Gly Ala
            100                 105                 110

Tyr Gly Ser Val Asn Lys Met Val His Lys Pro Ser Gly Gln Ile Met
        115                 120                 125

Ala Val Lys Arg Ile Arg Ser Thr Val Asp Glu Lys Glu Gln Lys Gln
    130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
            180                 185                 190

Tyr Ser Val Leu Asp Asp Val Ile Pro Glu Glu Ile Leu Gly Lys Ile
        195                 200                 205

Thr Leu Ala Thr Val Lys Ala Leu Asn His Leu Lys Glu Asn Leu Lys
    210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
            260                 265                 270
```

```
Glu Arg Ile Asp Pro Ser Ala Ser Arg Gln Gly Tyr Asp Val Arg Ser
            275                 280                 285

Asp Val Trp Ser Leu Gly Ile Thr Leu Tyr Glu Leu Ala Thr Gly Arg
        290                 295                 300

Phe Pro Tyr Pro Lys Trp Asn Ser Val Phe Asp Gln Leu Thr Gln Val
305                 310                 315                 320

Val Lys Gly Asp Pro Pro Gln Leu Ser Asn Ser Glu Arg Glu Phe
                325                 330                 335

Ser Pro Ser Phe Ile Asn Phe Val Asn Leu Cys Leu Thr Lys Asp Glu
            340                 345                 350

Ser Lys Arg Pro Lys Tyr Lys Glu Leu Leu Lys His Pro Phe Ile Leu
            355                 360                 365

Met Tyr Glu Glu Arg Ala Val Glu Val Ala Cys Tyr Val Cys Lys Ile
        370                 375                 380

Leu Asp Gln Met Pro Ala Thr Pro Ser Ser Pro Met Tyr Val Asp
385                 390                 395

(2) INFORMATION FOR SEQ ID NO:11:

(i) SEQUENCE CHARACTERISTICS:
        (A) LENGTH: 393 amino acids
        (B) TYPE: amino acid
        (C) STRANDEDNESS: Not Relevant
        (D) TOPOLOGY: linear (xi) SEQUENCE DESCRIPTION: SEQ ID NO:11:

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
```

```
                225                 230                 235                 240
Ser Val Gln Ser Asp Ile Trp Ser Met Gly Leu Ser Leu Val Glu Met
                    245                 250                 255

Ala Val Gly Arg Tyr Pro Ile Pro Pro Asp Ala Lys Glu Leu Glu
                260                 265                 270

Leu Met Phe Gly Cys Gln Val Glu Gly Asp Ala Ala Glu Thr Pro Pro
                275                 280                 285

Arg Pro Arg Thr Pro Gly Arg Pro Leu Ser Ser Tyr Gly Met Asp Ser
            290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                    325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
    370                 375                 380

Ser Thr Pro Thr His Ala Ala Gly Val
385                 390

(2) INFORMATION FOR SEQ ID NO:12:

(i) SEQUENCE CHARACTERISTICS:
        (A) LENGTH: 400 amino acids
        (B) TYPE: amino acid
        (C) STRANDEDNESS: Not Relevant
        (D) TOPOLOGY: linear (xi) SEQUENCE DESCRIPTION: SEQ ID NO:12:

Met Leu Ala Arg Arg Lys Pro Val Leu Pro Ala Leu Thr Ile Asn Pro
1               5                   10                  15

Thr Ile Ala Glu Gly Pro Ser Pro Thr Ser Glu Gly Ala Ser Glu Ala
                20                  25                  30

Asn Leu Val Asp Leu Gln Lys Lys Leu Glu Glu Leu Glu Leu Asp Glu
                35                  40                  45

Gln Gln Lys Lys Arg Leu Glu Ala Phe Leu Thr Gln Lys Ala Lys Val
    50                  55                  60

Ser Glu Leu Lys Asp Asp Asp Phe Glu Arg Ile Ser Glu Leu Gly Ala
65                  70                  75                  80

Gly Asn Gly Gly Val Val Thr Lys Val Gln His Arg Pro Ser Gly Leu
                85                  90                  95

Ile Met Ala Arg Lys Leu Ile His Leu Glu Ile Lys Pro Ala Ile Arg
                100                 105                 110

Asn Gln Ile Ile Arg Glu Leu Gln Val Leu His Glu Cys Asn Ser Pro
            115                 120                 125

Tyr Ile Val Gly Phe Tyr Gly Ala Phe Tyr Ser Asp Gly Glu Ile Ser
            130                 135                 140

Ile Cys Met Glu His Met Asp Gly Gly Ser Leu Asp Gln Val Leu Lys
145                 150                 155                 160

Glu Ala Lys Arg Ile Pro Glu Glu Ile Leu Gly Lys Val Ser Ile Ala
                165                 170                 175

Val Leu Arg Gly Leu Ala Tyr Leu Arg Glu Lys His Gln Ile Met His
                180                 185                 190
```

```
Arg Asp Val Lys Pro Ser Asn Ile Leu Val Asn Ser Arg Gly Glu Ile
            195                 200                 205

Lys Leu Cys Asp Phe Gly Val Ser Gly Gln Leu Ile Asp Ser Met Ala
        210                 215                 220

Asn Ser Phe Val Gly Thr Arg Ser Tyr Met Ala Pro Glu Arg Leu Gln
225                 230                 235                 240

Gly Thr His Tyr Ser Val Gln Ser Asp Ile Trp Ser Met Gly Leu Ser
                245                 250                 255

Leu Val Glu Leu Ala Val Gly Arg Tyr Pro Ile Pro Pro Asp Ala
            260                 265                 270

Lys Glu Leu Glu Ala Ile Phe Gly Arg Pro Val Val Asp Gly Glu Glu
        275                 280                 285

Gly Glu Pro His Ser Ile Ser Pro Arg Pro Arg Pro Gly Arg Pro
            290                 295                 300

Val Ser Gly His Gly Met Asp Ser Arg Pro Ala Met Ala Ile Phe Glu
305                 310                 315                 320

Leu Leu Asp Tyr Ile Val Asn Glu Pro Pro Pro Lys Leu Pro Asn Gly
                325                 330                 335

Val Phe Thr Pro Asp Phe Gln Glu Phe Val Asn Lys Cys Leu Ile Lys
            340                 345                 350

Asn Pro Ala Glu Arg Ala Asp Leu Lys Met Leu Thr Asn His Thr Phe
            355                 360                 365

Ile Lys Arg Ser Glu Val Glu Glu Val Asp Phe Ala Gly Trp Leu Cys
        370                 375                 380

Lys Thr Leu Arg Leu Asn Gln Pro Gly Thr Pro Thr Arg Thr Ala Val
385                 390                 395                 400

(2) INFORMATION FOR SEQ ID NO:13:

(i) SEQUENCE CHARACTERISTICS:
        (A) LENGTH: 668 amino acids
        (B) TYPE: amino acid
        (C) STRANDEDNESS: Not Relevant
        (D) TOPOLOGY: linear (xi) SEQUENCE DESCRIPTION: SEQ ID NO:13:

Met Glu Asp Lys Phe Ala Asn Leu Ser Leu His Glu Lys Thr Gly Lys
1               5                   10                  15

Ser Ser Ile Gln Leu Asn Glu Gln Thr Gly Ser Asp Asn Gly Ser Ala
            20                  25                  30

Val Lys Arg Thr Ser Ser Thr Ser Ser His Tyr Asn Asn Ile Asn Ala
        35                  40                  45

Asp Leu His Ala Arg Val Lys Ala Phe Gln Glu Gln Arg Ala Leu Lys
    50                  55                  60

Arg Ser Ala Ser Val Gly Ser Asn Gln Ser Glu Gln Asp Lys Gly Ser
65                  70                  75                  80

Ser Gln Ser Pro Lys His Ile Gln Gln Ile Val Asn Lys Pro Leu Pro
                85                  90                  95

Pro Leu Pro Val Ala Gly Ser Ser Lys Val Ser Gln Arg Met Ser Ser
            100                 105                 110

Gln Val Val Gln Ala Ser Ser Lys Ser Thr Leu Lys Asn Val Leu Asp
        115                 120                 125

Asn Gln Glu Thr Gln Asn Ile Thr Asp Val Asn Ile Asn Ile Asp Thr
    130                 135                 140

Thr Lys Ile Thr Ala Thr Thr Ile Gly Val Asn Ile Gly Leu Pro Ala
145                 150                 155                 160
```

-continued

```
Thr Asp Ile Thr Pro Ser Val Ser Asn Thr Ala Ser Ala Thr His Lys
            165                 170                 175
Ala Gln Leu Leu Asn Pro Asn Arg Arg Ala Pro Arg Arg Pro Leu Ser
        180                 185                 190
Thr Gln His Pro Thr Arg Pro Asn Val Ala Pro His Lys Ala Pro Ala
    195                 200                 205
Ile Ile Asn Thr Pro Lys Gln Ser Leu Ser Ala Arg Arg Gly Leu Lys
210                 215                 220
Leu Pro Pro Gly Gly Met Ser Leu Lys Met Pro Thr Lys Thr Ala Gln
225                 230                 235                 240
Gln Pro Gln Gln Phe Ala Pro Ser Pro Ser Asn Lys Lys His Ile Glu
                245                 250                 255
Thr Leu Ser Asn Ser Lys Val Val Glu Gly Lys Arg Ser Asn Pro Gly
            260                 265                 270
Ser Leu Ile Asn Gly Val Gln Ser Thr Ser Thr Ser Ser Thr Glu
        275                 280                 285
Gly Pro His Asp Thr Val Gly Thr Thr Pro Arg Thr Gly Asn Ser Asn
    290                 295                 300
Asn Ser Ser Asn Ser Gly Ser Ser Gly Gly Gly Leu Phe Ala Asn
305                 310                 315                 320
Phe Ser Lys Tyr Val Asp Ile Lys Ser Gly Ser Leu Asn Phe Ala Gly
                325                 330                 335
Lys Leu Ser Leu Ser Ser Lys Gly Ile Asp Phe Ser Asn Gly Ser Ser
            340                 345                 350
Ser Arg Ile Thr Leu Asp Glu Leu Glu Phe Leu Asp Glu Leu Gly His
        355                 360                 365
Gly Asn Tyr Gly Asn Val Ser Lys Val Leu His Lys Pro Thr Asn Val
    370                 375                 380
Ile Met Ala Thr Lys Glu Val Arg Leu Glu Leu Asp Glu Ala Lys Phe
385                 390                 395                 400
Arg Gln Ile Leu Met Glu Leu Glu Val Leu His Lys Cys Asn Ser Pro
                405                 410                 415
Tyr Ile Val Asp Phe Tyr Gly Ala Phe Phe Ile Glu Gly Ala Val Tyr
            420                 425                 430
Met Cys Met Glu Tyr Met Asp Gly Gly Ser Leu Asp Lys Ile Tyr Asp
        435                 440                 445
Glu Ser Ser Glu Ile Gly Gly Ile Asp Glu Pro Gln Leu Ala Phe Ile
    450                 455                 460
Ala Asn Ala Val Ile His Gly Leu Lys Glu Leu Lys Glu Gln His Asn
465                 470                 475                 480
Ile Ile His Arg Asp Val Lys Pro Thr Asn Ile Leu Cys Ser Ala Asn
                485                 490                 495
Gln Gly Thr Val Lys Leu Cys Asp Phe Gly Val Ser Gly Asn Leu Val
            500                 505                 510
Ala Ser Leu Ala Lys Thr Asn Ile Gly Cys Gln Ser Tyr Met Ala Pro
        515                 520                 525
Glu Arg Ile Lys Ser Leu Asn Pro Asp Arg Ala Thr Tyr Thr Val Gln
    530                 535                 540
Ser Asp Ile Trp Ser Leu Gly Leu Ser Ile Leu Glu Met Ala Leu Gly
545                 550                 555                 560
Arg Tyr Pro Tyr Pro Pro Glu Thr Tyr Asp Asn Ile Phe Ser Gln Leu
                565                 570                 575
```

```
-continued

Ser Ala Ile Val Asp Gly Pro Pro Pro Arg Leu Pro Ser Asp Lys Phe
            580                 585                 590

Ser Ser Asp Ala Gln Asp Phe Val Ser Leu Cys Leu Gln Lys Ile Pro
        595                 600                 605

Glu Arg Arg Pro Thr Tyr Ala Ala Leu Thr Glu His Pro Trp Leu Val
    610                 615                 620

Lys Tyr Arg Asn Gln Asp Val His Met Ser Glu Tyr Ile Thr Glu Arg
625                 630                 635                 640

Leu Glu Arg Arg Asn Lys Ile Leu Arg Glu Arg Gly Glu Asn Gly Leu
                645                 650                 655

Ser Lys Asn Val Pro Ala Leu His Met Gly Gly Leu
                660                 665

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

TTYTAYGGNG CNTTYTTYAT HGA                                       23

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

ATBCTYTCNG GNGCCATKTA                                           20

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:16:

ASTYRYSASA SASASYS                                              17
```